(12) United States Patent
Tahara et al.

(10) Patent No.: US 9,096,878 B2
(45) Date of Patent: *Aug. 4, 2015

(54) EXPRESSION VECTOR FOR PRODUCING PROTEIN DERIVED FROM FOREIGN GENE IN LARGE QUANTITY USING ANIMAL CELLS, AND USE THEREOF

(75) Inventors: Hiroshi Tahara, Osaka (JP); Yusuke Suzuki, Osaka (JP); Keiichi Yamamoto, Osaka (JP); Yuzuru Kitahara, Osaka (JP); Yasuhiko Suzuki, Sapporo (JP)

(73) Assignees: National University Corporation Hokkaido University, Hokkaido (JP); Fuso Pharmaceutical Industries, Ltd., Osaka (JP)

( * ) Notice: Subject to any disclaimer, the term of this patent is extended or adjusted under 35 U.S.C. 154(b) by 1013 days.

This patent is subject to a terminal disclaimer.

(21) Appl. No.: 13/140,905

(22) PCT Filed: Dec. 22, 2009

(86) PCT No.: PCT/JP2009/071326
§ 371 (c)(1),
(2), (4) Date: Jan. 24, 2012

(87) PCT Pub. No.: WO2010/074080
PCT Pub. Date: Jul. 1, 2010

(65) Prior Publication Data
US 2012/0122083 A1    May 17, 2012

(30) Foreign Application Priority Data
Dec. 22, 2008 (JP) .................. 2008-325690

(51) Int. Cl.
C12P 21/02       (2006.01)
C12N 15/85       (2006.01)

(52) U.S. Cl.
CPC ............ C12P 21/02 (2013.01); C12N 15/85 (2013.01); C12N 2830/00 (2013.01)

(58) Field of Classification Search
None
See application file for complete search history.

(56) References Cited

U.S. PATENT DOCUMENTS

| | | | |
|---|---|---|---|
| 5,627,033 | A | 5/1997 | Smith et al. |
| 5,760,185 | A | 6/1998 | Kimachi et al. |
| 8,653,249 | B2 * | 2/2014 | Suzuki et al. ............ 536/24.1 |
| 2011/0123993 | A1 | 5/2011 | Suzuki et al. |
| 2012/0059152 | A1 | 3/2012 | Suzuki et al. |

FOREIGN PATENT DOCUMENTS

| | | |
|---|---|---|
| CA | 2 507 664 | 9/2010 |
| CN | 1771324 | 4/2006 |
| EP | 0 117 058 | 8/1984 |
| EP | 0 117 059 | 8/1984 |
| EP | 1591523 | 11/2005 |
| JP | 59-183693 | 10/1984 |
| JP | 6-30788 | 2/1994 |
| JP | 6-165672 | 6/1994 |
| JP | 6-506356 | 7/1994 |
| JP | 6-217786 | 8/1994 |
| JP | 7-67648 | 3/1995 |
| JP | 7-265084 | 10/1995 |
| JP | 8-503138 | 4/1996 |
| JP | 10-179169 | 7/1998 |
| JP | 2002-45191 | 2/2002 |
| JP | 2003-513635 | 4/2003 |
| JP | 2006-500927 | 1/2006 |
| JP | 2006-507842 | 3/2006 |
| JP | 2008-518613 | 6/2008 |
| WO | 85/02610 | 6/1985 |
| WO | 92/17566 | 10/1992 |
| WO | 94/11523 | 5/1994 |
| WO | 01/32901 | 5/2001 |
| WO | 2004/024915 | 3/2004 |
| WO | 2006/048459 | 5/2006 |
| WO | 2006/106970 | 10/2006 |
| WO | 2007/096399 | 7/2007 |
| WO | 2009/107775 | 9/2009 |

OTHER PUBLICATIONS

International Search Report for PCT/JP2009/017326 completed on Jan. 21, 2010 and mailed on Feb. 2, 2010.

Asselbergs et al., "Use of the *Escherichia coli* chromosomal DHFR gene as selection marker in mammalian cells" Journal of Biotechnology, 43(2):133-138 (Dec. 1, 1995).

Bebbington et al., "High-Level Expression of a Recombinant Antibody From Myeloma Cells Using a Glutamine Synthetase Gene as an Amplifiable Selectable Marker" Nature Biotechnology, 10:169-175 (1992).

Gandor et al., "Amplification and expression of recombinant genes in serum-independent Chinese hamster ovary cells" FEBS Lett. 377(3):290-4 (Dec. 27, 1995).

Gillies et al., "High-level expression of chimeric antibodies using adapted cDNA variable region cassettes" J Immunol Methods. 125(1-2):191-202 (Dec. 20, 1989).

(Continued)

*Primary Examiner* — Jennifer Dunston
*Assistant Examiner* — Addison D Ault
(74) *Attorney, Agent, or Firm* — Karl Bozicevic; Bozicevic, Field & Francis LLP

(57) ABSTRACT

The present inventors conducted dedicated studies and successfully constructed expression vectors that enable high-level production of foreign gene-derived proteins in mammalian host cells, which comprise a translation-impaired dihydrofolate reductase gene cistron whose expression has been attenuated by altering the codons to the least frequently used codons in mammals; and a gene cassette which has a cloning site for incorporation of a foreign gene between a highly transcriptionally active promoter and a highly stable polyadenylation signal.

5 Claims, 28 Drawing Sheets

(56) References Cited

OTHER PUBLICATIONS

Goto et al., "Production of Recombinant Human Erythropoietin in Mammalian Cells: Host-Cell Dependency of the Biological Activity of the Cloned Glycoprotein" Nature Biotechnology, 6:67-71 (1988).

Grillari et al., "Analysis of alterations in gene expression after amplification of recombinant genes in CHO cells" Journal of Biotechnology, 87(1):59-65 (Apr. 27, 2001).

Miyaji et al., "Efficient expression of human beta-interferon in Namalwa KJM-1 cells adapted to serum-free medium by a dhfr gene coamplification method" Cytotechnology, 4(2):173-80 (Sep. 1990).

Newman et al., ""Primatization" of Recombinant Antibodies for Immunotherapy of Human Diseases: A Macaque/Human Chimeric Antibody Against Human CD4" Nature Biotechnology, 10:1455-1460 (1992).

Powell et al., "Human erythropoietin gene: High level expression in stably transfected mammalian cells and chromosome localization" Proc. Natl. Acad. Sci. USA, 83(17):6465-9 (Sep. 1986).

Scahill et al., "Expression and characterization of the product of a human immune interferon cDNA gene in Chinese hamster ovary cells" Proc. Natl. Acad. Sci. USA, 80(15):4654-8 (Aug. 1983).

Van Blokland et al., "A novel, high stringency selection system allows screening of few clones for high protein expression" Journal of Biotechnology, 128(2):237-45 (Feb. 1, 2007) (Epub. Oct. 10, 2006).

Yanagi et al., "High-Level Expression of Human Erythropoietin cDNA in Stably Transfected Namalwa Cells" Journal of Fermentation and Bioengineering, 68(4):257-263 (1989).

Kim et al., "Codon optimization for high level expression of human erythropoietin (EPO) in mammalian cells" Gene (Oct. 15, 1997) 199(1-2):293-301.

* cited by examiner

EXPRESSION VECTOR FOR PRODUCING PROTEIN DERIVED FROM FOREIGN GENE IN LARGE QUANTITY USING ANIMAL CELLS, AND USE THEREOF

TECHNICAL FIELD

The present invention relates to mammalian cell expression vectors that confer mammalian host cells with the ability of producing high levels of foreign gene-derived proteins. The expression vectors of the present invention are particularly suitable for production of mammalian proteins which require glycosylation and folding unique to mammals and hardly have sufficient activity when produced by genetic recombination using *E. coli* or yeast as host.

BACKGROUND ART

A large number of vectors for producing recombinant proteins have been developed, and the expression levels of proteins are high in expression systems that use bacteria such as *E. coli*, eukaryotic microorganisms such as yeast, and insect cells as host. However, when expressing proteins unique to mammals, they may not form a normal three-dimensional structure, and most of the time there is a problem with post-translational modifications such as glycosylation. Thus, it is necessary to establish expression systems that use mammalian cells as host, but in general, the expression level is low in most cases. Furthermore, expression systems that use recombinant virus vectors are also used in animal cells, which are higher than insect cells, but removing recombinant virus vectors from the expressed proteins is a very cumbersome process and the risk of virus vectors themselves cannot be denied.

Cases of recombinant protein production using a mammalian cell as host include tissue plasminogen activator (Patent Document 1), erythropoietin (Patent Document 2 and Non-patent Documents 1-3), IFN-γ (Non-patent Document 4), and IFN-β (Patent Document 3 and Non-patent Document 5). Furthermore, there are many reports about recombinant production of monoclonal antibodies (Patent Documents 4 to 6, and Non-patent Documents 6 to 8). In addition, an example of a high expression vector for mammalian cells is pNOW/CMV-AA (Patent Document 7). The production level of conglutinin using this vector was up to 11.8 μg/mL after four days of culture. However, the production level of recombinant protein is unlikely to be sufficient in these cases.

Prior art documents relating to the invention of this application are shown below.

PRIOR ART DOCUMENTS

Patent Documents

[Patent Document 1] Japanese Patent Application Kokai Publication No. (JP-A) S59-183693 (unexamined, published Japanese patent application)
[Patent Document 2] JP-A (Kokai) 2002-45191
[Patent Document 3] JP-A (Kokai) H07-265084
[Patent Document 4] JP-A (Kokai) H07-67648
[Patent Document 5] JP-A (Kokai) H06-30788
[Patent Document 6] JP-A (Kokai) H06-217786
[Patent Document 7] JP-A (Kokai) H10-179169

Non-patent Documents

[Non-patent Document 1] Fermentation Bioengineering, (1989) 4: p. 257
[Non-patent Document 2] Proc. Natl. Acad. Sci. USA, (1986) 83: p. 6465
[Non-patent Document 3] Biotechnology, (1988) 6: p. 67
[Non-patent Document 4] Proc. Natl. Acad. Sci. USA, (1983) 80: p. 4564
[Non-patent Document 5] Cytotechnology, (1990) 4: p. 173
[Non-patent Document 6] Biotechnology, (1992) 10: p. 169
[Non-patent Document 7] J. Immunol. Methods, (1989) 125: p. 191
[Non-patent Document 8] Biotechnology, (1992) 10: p. 1455

DISCLOSURE OF THE INVENTION

Problems to be Solved by the Invention

Use of mammalian cells, particularly Chinese hamster ovary cells (hereinafter, CHO cells) in production of pharmaceutical agents, has been confirmed safe and becomes a common technique now. In the production of recombinant proteins using mammalian cells, increasing the productivity is very important from the aspects of cost reduction, healthcare cost containment, and such. Therefore, development of expression vectors for producing transformants having a high-level production ability through efficient gene transfer is necessary.

Efficient gene transfer is necessary for easy production of high levels of recombinant protein in mammalian cells. Efficient gene transfer means that the probability of obtaining clones with high-level productivity is high regardless of whether clone selection is easy or not. Specifically, this means that the number of viable cell clones after drug selection to all transformed cells is relatively small, and therefore selection of clones with high-level productivity is easy. It also means that the probability of occurrence of clones with high-level productivity is high even if the number of cells producing the protein of interest is small. As the number of available cells becomes large, more time and effort are required for selection, and leads to inefficiency and high probability of overlooking clones that potentially have high-level production ability.

High-level production ability refers to high expression level of recombinant protein in the transformed cell clones obtained by gene transfer, and this is considered to be mainly due to the characteristics and performance of the expression vectors. It has been found that the level of gene expression is remarkably different depending on the chromosomal position (Annu. Rev. Cell Biol., 6, page 679, 1990), and introduction of a gene of interest to a region with high transcriptional activity on the chromosome (hereinafter, transcriptional hot spot) is likely to increase the level of recombinant protein production.

The present invention was achieved in view of the above circumstances. An objective of the present invention is to provide expression vectors for mammalian cells which confer mammalian host cells with the ability of producing foreign gene-derived proteins at high levels. Another objective of the present invention is to provide methods for producing transformants utilizing the above-mentioned vectors and methods for producing foreign gene-derived proteins utilizing the above-mentioned vectors.

Means for Solving the Problems

Upon dedicated research to solve the above-mentioned problems, the present inventors successfully developed expression vectors that have the mechanism to incorporate a plasmid DNA into the transcriptional hotspot on the chromosome of a dihydrofolate reductase gene-deficient host cell, and select strains that grow in hypoxanthine-thymidine (hereinafter denoted as HT)-free medium. Since dihydrofolate reductase (DHFR) is necessary for biosynthesis of nucleobases, it is an essential enzyme for all organisms which use DNA as the material for genetic information. Therefore, dihydrofolate reductase gene-deficient host cells cannot grow in a medium that does not contain HT which is a component of nucleic acids. Cells that express a protein of interest can be selected by introducing a construct incorporating the gene of a protein of interest and the DHFR gene into dihydrofolate reductase gene-deficient host cells and then culturing the cells under HT-free conditions. Compared to the method of introducing a construct incorporating the gene of a protein of interest and the neomycin phosphotransferase gene and then performing selection with G418, this method allows gene amplification by MTX which is a DHFR inhibitor and is therefore more suitable for obtaining strains producing the protein of interest at high levels. As a result, an expression vector that enables stable, high-level protein production was constructed, and the present invention was completed.

More specifically, the present invention provides the following:

[1] an expression vector for enabling high-level production of a foreign gene-derived protein in a mammalian host cell, which comprises:
 (a) a translation-impaired dihydrofolate reductase gene cassette (translation-impaired DHFR gene cassette), whose expression is attenuated by altering codons to the least frequently used codons in a mammal; and
 (b) a gene cassette comprising a cloning site for integration of a foreign gene between a highly transcriptionally active promoter and a highly stable polyadenylation signal;
[2] the expression vector of [1], wherein the codons of the translation-impaired DHFR gene cassette of [1](a) have been altered to the least frequently used codons in humans;
[3] the expression vector of [1], wherein the codons of the translation-impaired DHFR gene cassette of [1](a) have been altered to GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and/or GUA for valine;
[4] the expression vector of [1], wherein the translation-impaired DHFR gene cassette of [1](a) uses a promoter with low expression-inducing activity as the promoter;
[5] the expression vector of [4], wherein the low-activity promoter used is a promoter derived from a gene that is hardly expressed in a mammalian cell or a promoter whose enhancer portion has been removed;
[6] the expression vector of [1], wherein a codon-altered region in the translation-impaired DHFR gene cassette of [1](a) is 30% or more of the full length of the gene cassette;
[7] a method for producing a transformant that has ability to produce a high level of a foreign gene-derived protein, which comprises the steps of inserting a foreign gene into the expression vector of any one of [1] to [6], and transforming a dihydrofolate reductase gene-deficient host cell with the expression vector;
[8] a method for producing a foreign gene-derived protein, which comprises the steps of:
 (a) inserting a foreign gene into the expression vector of any one of [1] to [6];
 (b) transforming a dihydrofolate reductase gene-deficient host cell with the expression vector;
 (c) culturing the transformant in a hypoxanthine-thymidine-free medium; and
 (d) collecting the foreign gene-derived protein from the cultured transformant;
[9] the method of [8], wherein a chemically defined medium (CD medium) or a CD medium supplemented with a non-animal-based additive is used for culturing in step (c) of [8]; and
[10] a method of screening for a transformant that has ability to produce a high level of a foreign gene-derived protein, which comprises the steps of:
 (a) inserting a foreign gene into the expression vector of any one of [1] to [6];
 (b) transforming a dihydrofolate reductase gene-deficient host cell with the expression vector; and
 (c) culturing the transformant in a hypoxanthine-thymidine-free medium.

MODE FOR CARRYING OUT THE INVENTION

Figure 1:
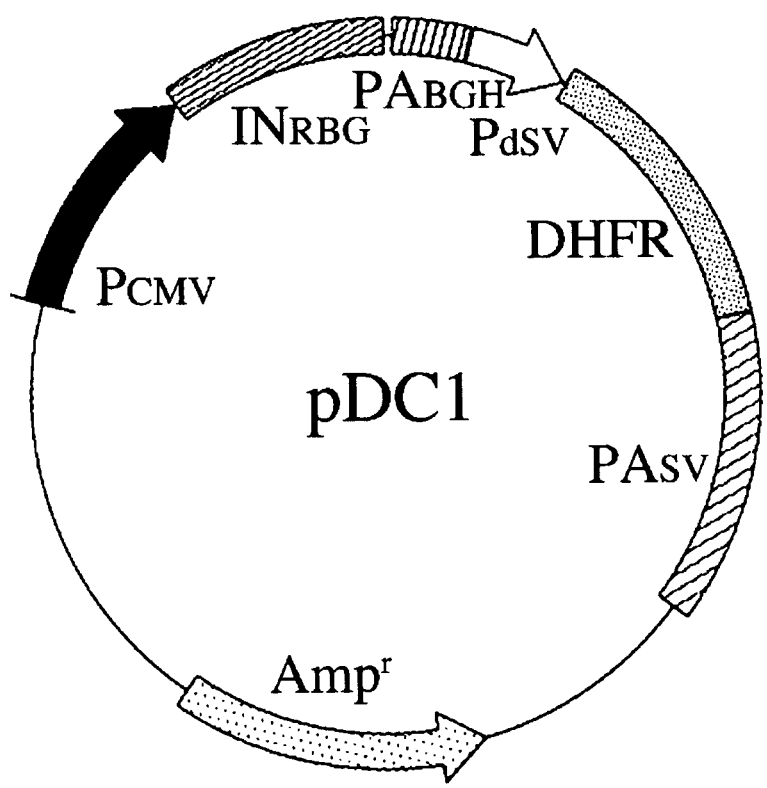
FIG. 1 shows the pDC1 construct with the respective abbreviations shown below. PCMV: cytomegalovirus promoter; INRBG: rabbit growth hormone intron; PABGH: bovine growth hormone gene polyA addition signal; PdSV: enhancer-deleted simian virus 40 promoter; DHFR: dihydrofolate reductase cDNA; PASV: simian virus 40 polyA addition signal; and $Amp^r$: selection marker (ampicillin resistance) in *E. coli*.

By altering the codons of the DHFR gene to the least frequently used codons in mammals to utterly attenuate the expression of DHFR, the present inventors made the survival under selection in medium not containing HT difficult even for transformants unless the incorporated plasmid gene is integrated into a position with very high expression properties on the chromosome of dihydrofolate reductase gene-deficient host cells.

More specifically, the present invention provides expression vectors for inducing high-level production of recombinant proteins in mammalian host cells.

An expression vector of the present invention is constructed by including the following on a backbone vector:
(a) a translation-impaired dihydrofolate reductase gene cassette (a translation-impaired DHFR gene cassette), whose expression is weakened by altering codons to the least frequently used codons in a mammal; and
(b) a gene cassette comprising a cloning site for integration of a foreign gene between a highly transcriptionally-active promoter and a highly stable polyadenylation signal.

The present invention markedly impairs the expression mechanism of DHFR in the host cell transformed through gene transfer by altering the codons of the DHFR gene to the least frequently used codons in mammals, and using promoters with decreased expression-inducing property of DHFR for the DHFR gene cassette (cistron) construct. In the present invention, "gene cassette" refers to a unit with the basic composition of promoter, structural gene, and polyadenylation signal (polyA) that expresses protein through transcription/translation, and it may also include as insertion sequences DNA sequences associated with any of these sequences or any optional DNA sequences. The DHFR gene cassettes of the present invention are defined as "translation-impaired DHFR gene cassette" because they differ from those with a simply attenuated promoter, and they specifically allow acquirement of strains that grow in HT-free media and have the plasmid gene integrated into a transcriptional hot spot.

In the present invention, "the least frequently used codons in mammals" refers to preferably, for example, the least frequently used codons in humans. The least frequently used codons in humans include the codons disclosed in the document by Kim et al. (Gene, 199, p. 293, 1997). Specific examples of the codons are GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and/or GUA for valine, but are not limited thereto.

In the present invention, "to attenuate expression" indicates reducing gene expression at the transcription and/or translation levels, and specifically, this can be achieved by altering the codons to the above-mentioned "least frequently used codons in mammals".

In the above-mentioned "translation-impaired DHFR gene cassette", the regions in which codons are altered are not particularly limited, but preferably, codons in a region corresponding to 30% or more (for example, 40% or more, 50% or more, 60% or more, 70% or more, 80% or more, 90% or more, 95% or more, or 100%) of the full length of the gene cassette are altered. The range of the codon-altered regions can be determined arbitrarily by considering other conditions of the vector.

As the promoter for the above-mentioned "translation-impaired DHFR gene cassette", promoters derived from the promoter of a gene of a protein which is normally difficult to express in a mammalian cell, or promoters produced by deleting the enhancer from a normal promoter may be used. More specifically, a promoter produced by deleting the enhancer region from the SV40 virus antigen promoter (Mol. Cell Biol., 6, p. 2593, 1986), or promoters with an equivalently very low expression property are preferably used.

Integration of plasmid DNA into a transcriptional hot spot on the dihydrofolate reductase gene-deficient host cell chromosome can be accomplished as a result by selection with a medium not containing HT according to the properties of the DHFR gene cassette, but expression of the foreign gene-derived protein itself at the transcriptional hot spot of the chromosome must be strongly induced. Therefore, the promoters and polyadenylation signal (hereinafter, called polyA) in the multicloning site (hereinafter, referred to as MCS) where the protein genes are inserted will be selected from among those having the strongest expression-inducing property. Examples of the promoters include human cytomegalovirus immediate early (hCMV MIE: Cell, 41, p. 521, 1985) promoter, CMV5 promoter which is a fusion promoter of human cytomegalovirus promoter and adenovirus promoter (Nucleic Acid Research, 30, p. 2, 2002), and β-actin promoter (Proc. Natl. Acad. Sci. USA, 84, p. 4831, 1987); and examples of polyA include the bovine growth hormone-derived polyA sequence (DNA, 5, p. 115, 1986). Herein, a DNA fragment carrying a multicloning site for inserting the gene of a protein of interest is called a "gene expression cassette".

Expression vectors of the present invention can be exemplified by expression vectors specifically described in the Examples, but are not limited thereto.

Furthermore, the present invention provides a method for producing transformants with an ability to produce foreign gene-derived proteins at high levels and an ability to grow in a medium not containing HT, which comprises the steps of inserting a foreign gene into the above-mentioned expression vectors and transforming dihydrofolate reductase gene-deficient host cells using the expression vectors.

Specific examples include a method of obtaining transformants with high protein-producing ability, which involves inserting a foreign gene encoding a protein to be expressed into the multicloning site (hereinafter, referred to as MCS) of an expression vector of the present invention, then transforming dihydrofolate reductase gene-deficient host cells with the expression vector by using a transfection method (examples of the transfection method referred to herein include methods well known to those skilled in the art such as lipofectin method, electroporation method, calcium phosphate method, and microinjection method), and then selecting by resistance in a medium not containing HT.

In the present invention, the host cells are not particularly limited as long as they are cells suitable for expressing foreign gene-derived proteins, but preferably include, for example, dihydrofolate reductase gene-deficient mammalian cells, and more preferably dihydrofolate reductase gene-deficient Chinese hamster ovary cells (CHO cells).

Many of the transformed cells that survived selection in an HT-free medium have already achieved a relatively high protein expression level, but to select from these cells transformed cells that have an even higher level of production ability, the level of protein expression may be determined Furthermore, the present invention provides methods for producing a foreign gene-derived protein, which comprise the steps of:
(a) inserting a foreign gene into an expression vector of the present invention;
(b) transforming a dihydrofolate reductase gene-deficient host cell with the expression vector;
(c) culturing the transformant in an HT-free medium; and
(d) collecting the foreign gene-derived protein from the cultured transformant.

In the present invention, in step (c) mentioned above, transformants (colonies) showing high-efficiency protein expression can be selected by culturing in an HT-free medium. The selected transformants may be continuously cultured in the same medium, or they may be cultured after transferring to another medium such as a medium for large-scale expression.

In the present invention, media for culturing or naturalizing transformants are not particularly limited, but are for example, preferably a serum-free medium, and more preferably a CD medium or a CD medium supplemented with non-animal-based additives.

In the present invention, when collecting foreign gene-derived proteins from cultured transformants, the proteins may be purified by methods known to those skilled in the art (filtration, centrifugation, column purification, and such). The foreign gene-derived proteins can be expressed as fusion proteins with other proteins to facilitate purification and such.

Furthermore, the present invention provides a method of screening for transformants with high ability to produce a foreign gene-derived protein, which comprises the steps of:
(a) inserting a foreign gene into an expression vector of the present invention;
(b) transforming a dihydrofolate reductase gene-deficient host cell with the expression vector; and
(c) culturing the transformant in an HT-free medium.

All prior art documents cited in the specification are incorporated herein by reference.

EXAMPLES

Example 1

Construction of pDC1, pDC2, pDC5, pDC6, and pDC7

Figure 2:
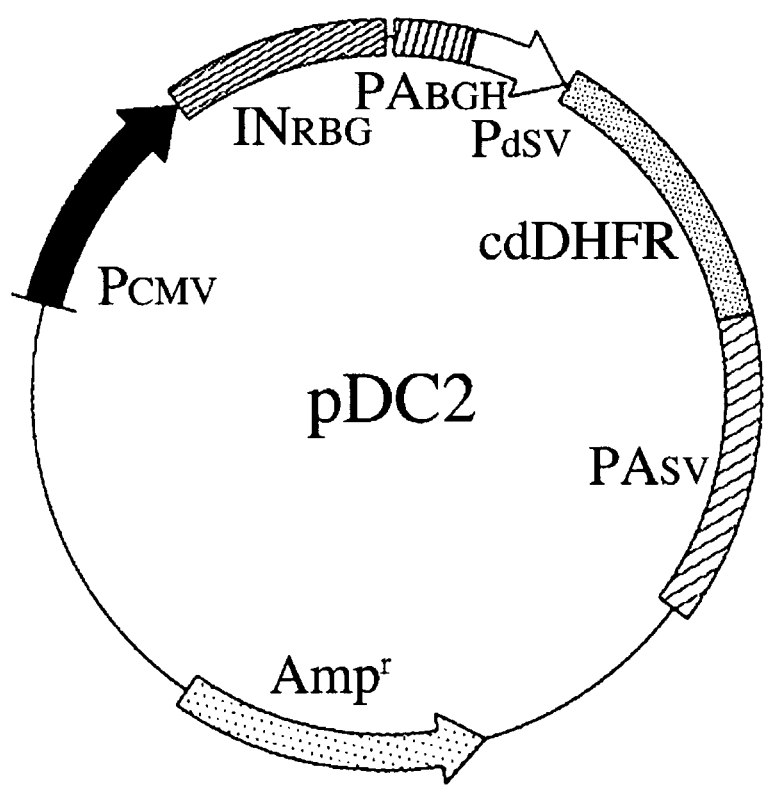
FIG. 2 shows the pDC2 construct with the respective abbreviations shown below. PCMV: cytomegalovirus promoter; INRBG: rabbit growth hormone intron; PABGH: bovine growth hormone gene polyA addition signal; PdSV: enhancer-deleted simian virus 40 promoter; cdDHFR: translation-impaired DHFR gene produced by altering the codons of the entire DHFR nucleotide sequence to the least frequently used codons in mammals; PASV: simian virus 40 polyA addition signal; and $Amp^r$: selection marker (ampicillin resistance) in *E. coli*.
Figure 3:
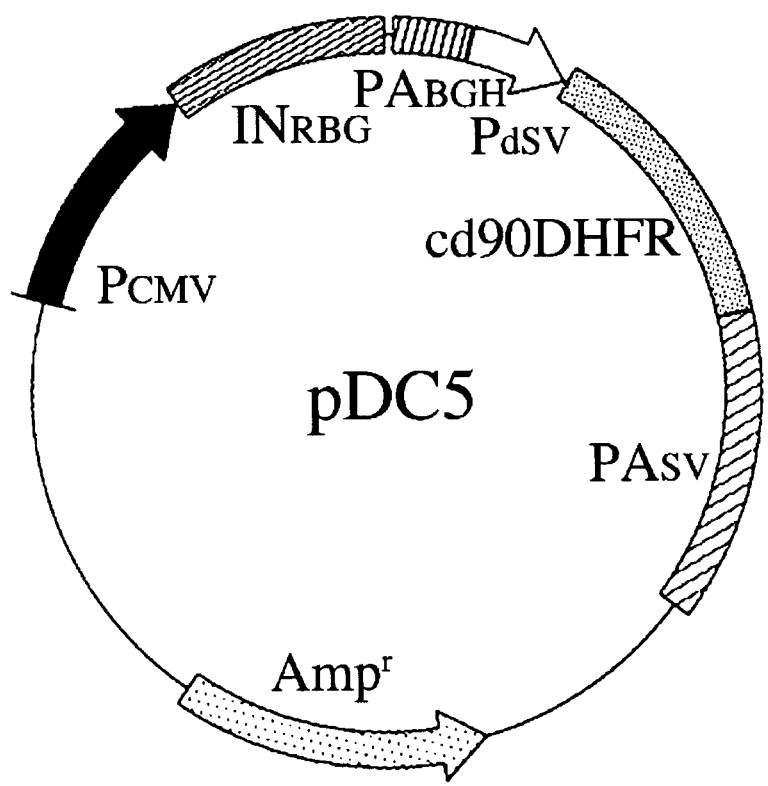
FIG. 3 shows the pDC5 construct with the respective abbreviations shown below. PCMV: cytomegalovirus promoter; INRBG: rabbit growth hormone intron; PABGH: bovine growth hormone gene polyA addition signal; PdSV: enhancer-deleted simian virus 40 promoter; cd90DHFR: translation-impaired NPT gene produced by altering codons in the range of 90 bases from the 5' end of the DHFR nucleotide sequence to the least frequently used codons in mammals; PASV: simian virus 40 polyA addition signal; and $Amp^r$: selection marker (ampicillin resistance) in *E. coli*.
Figure 4:
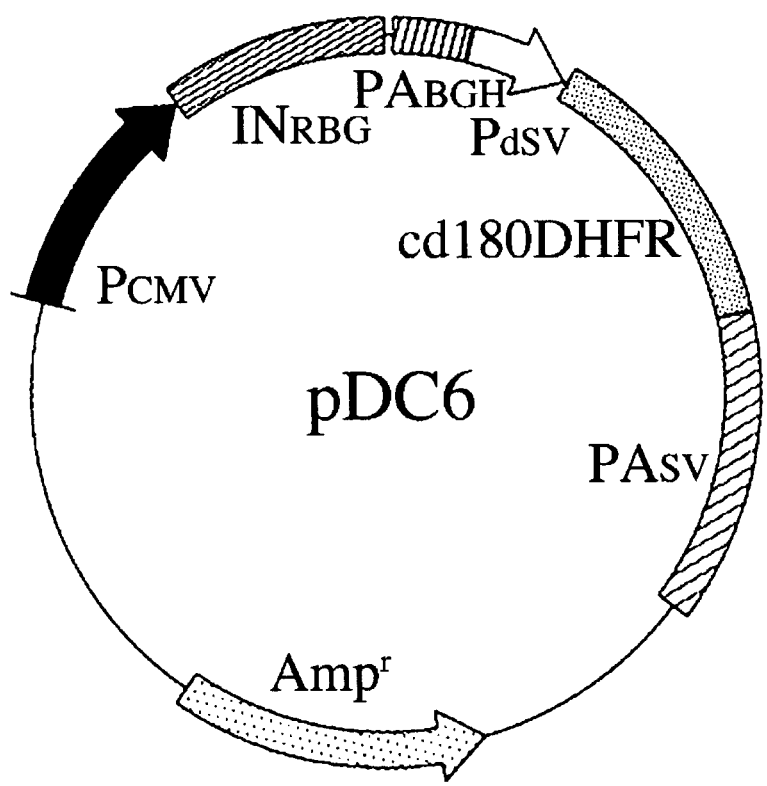
FIG. 4 shows the pDC6 construct with the respective abbreviations shown below. PCMV: cytomegalovirus promoter; INRBG: rabbit growth hormone intron; PABGH: bovine growth hormone gene polyA additional signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA additional signal; and $Amp^r$: selection marker (ampicillin resistance) in *E. coli*.
Figure 5:
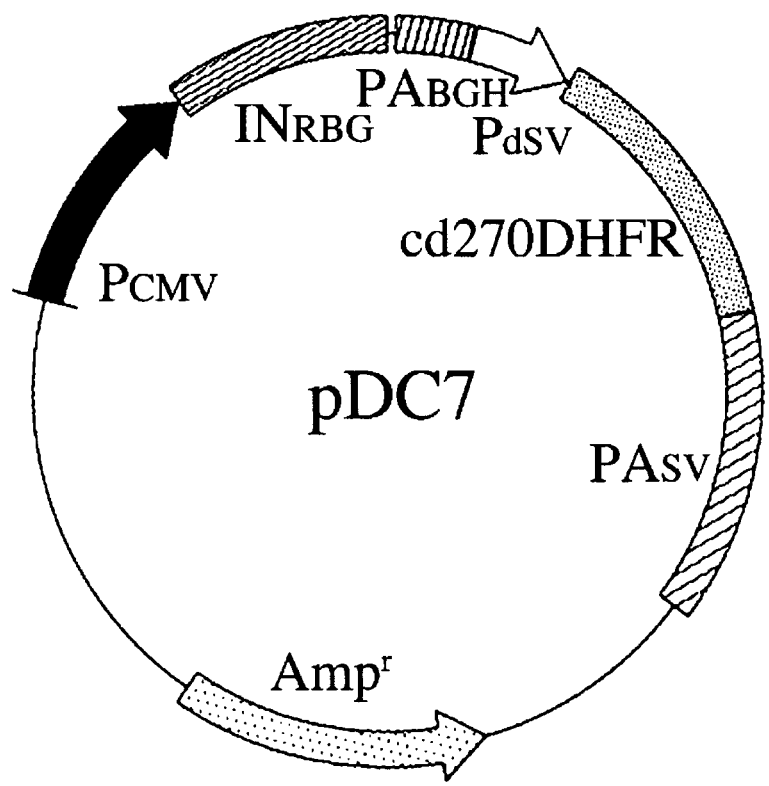
FIG. 5 shows the pDC7 construct with the respective abbreviations shown below. PCMV: cytomegalovirus promoter; INRBG: rabbit growth hormone intron; PABGH: bovine growth hormone gene polyA addition signal; PdSV: enhancer-deleted simian virus 40 promoter; cd270DHFR: translation-impaired DHFR gene produced by altering codons in the range of 270 bases from the 5' end of the nucleotide sequence of DHFR to the least frequently used codons in mammals; PASV: simian virus 40 polyA addition signal; and Amp$^r$: selection marker (ampicillin resistance) in *E. coli*.

Using methods well known to those skilled in the art, vectors of the present invention, pDC1, pDC2, pDC5, pDC6, and pDC7, were constructed. The entire nucleotide sequence of the backbone vector pDC1 is shown in SEQ ID NO: 1. pDC1 carries the wild-type DHFR cDNA between nucleotides No. 1784 and No. 2347 (FIG. 1). pDC2 is constructed by substituting nucleotides No. 1784 to No. 2347 in the sequence of pDC1 with the sequence of SEQ ID NO: 2. The substituted region of pDC2 is introduced with a translation-impaired DHFR gene in which the codons of the entire nucleotide sequence of DHFR have been altered to the least frequently used codons in mammals (FIG. 2).

pDC5 is constructed by substituting nucleotides No. 1784 to No. 2347 in the sequence of pDC1 with the sequence of SEQ ID NO: 3. The substituted region of pDC5 is introduced with a translation-impaired DHFR gene in which codons in the range of 90 bases from the 5' end of the DHFR nucleotide sequence have been altered to the least frequently used codons in mammals (FIG. 3).

pDC6 is constructed by substituting nucleotides No. 1784 to No. 2347 in the sequence of pDC1 with the sequence of SEQ ID NO: 4. The substituted region of pDC6 is introduced with a translation-impaired DHFR gene in which codons in the range of 180 bases from the 5' end of the DHFR nucleotide sequence have been altered to the least frequently used codons in mammals (FIG. 4).

pDC7 is constructed by substituting nucleotides No. 1784 to No. 2347 in the sequence of pDC1 with the sequence of SEQ ID NO: 5. The substituted region of pDC7 is introduced with a translation-impaired DHFR gene in which codons in the range of 270 bases from the 5' end of the DHFR nucleotide sequence have been altered to the least frequently used codons in mammals (FIG. 5).

Example 2

Construction of pDC1/hMBL, pDC2/hMBL, pDC5/hMBL, pDC6/hMBL, and pDC7/hMBL

Figure 6:
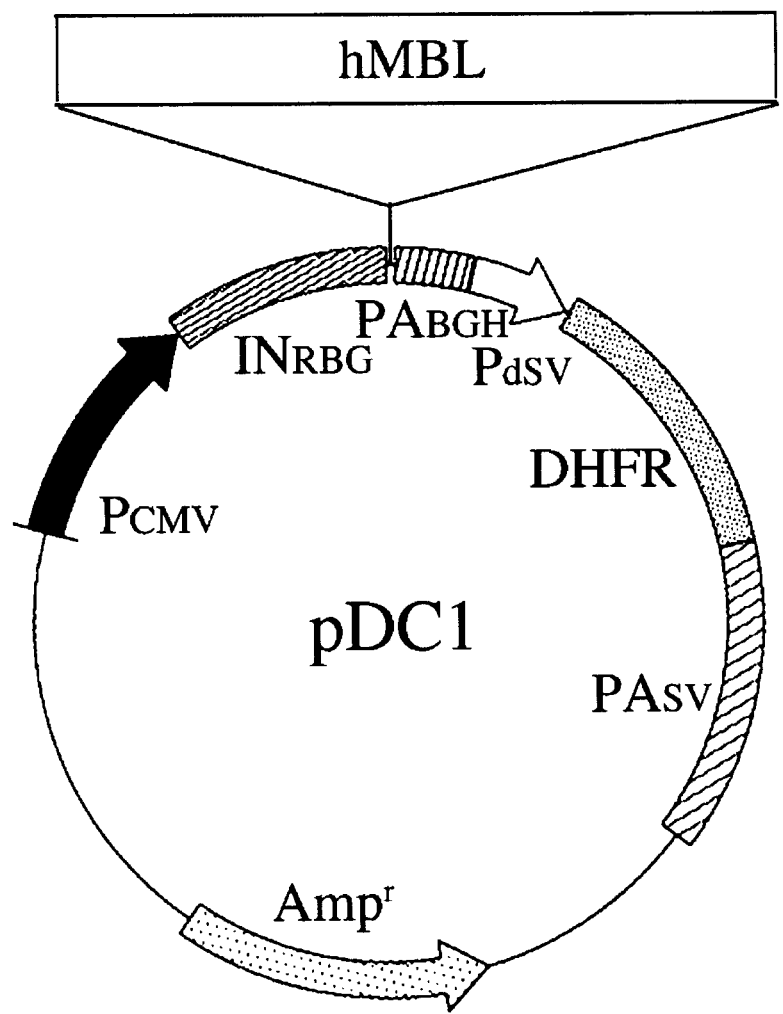
FIG. 6 shows the pDC1/hMBL construct with the respective abbreviations shown below. PCMV: cytomegalovirus promoter; INRBG: rabbit growth hormone intron; hMBL: human mannose-binding lectin cDNA; PABGH: bovine growth hormone gene polyA addition signal; PdSV: enhancer-deleted simian virus 40 promoter; DHFR: dihydrofolate reductase cDNA; PASV: simian virus 40 polyA addition signal; and Amp$^r$: selection marker (ampicillin resistance) in *E. coli*.
Figure 7:
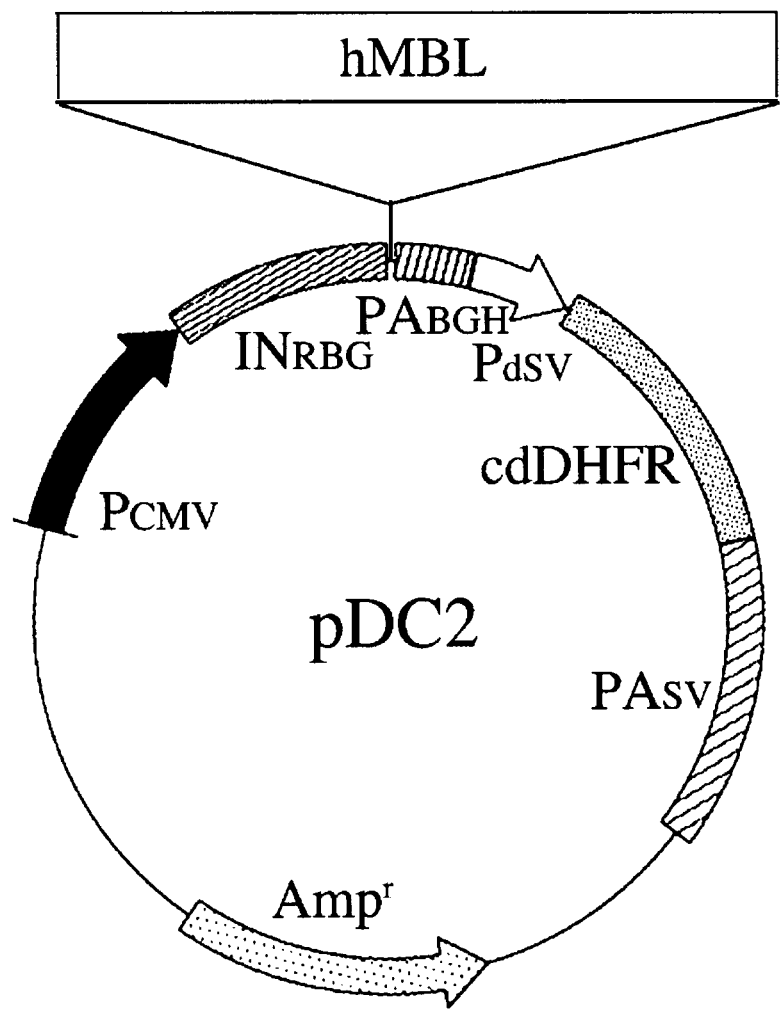
FIG. 7 shows the pDC2/hMBL construct with the respective abbreviations shown below. PCMV: cytomegalovirus promoter; INRBG: rabbit growth hormone intron; hMBL: human mannose-binding lectin cDNA; PABGH: bovine growth hormone gene polyA addition signal; PdSV: enhancer-deleted simian virus 40 promoter; cdDHFR: translation-impaired DHFR gene produced by altering the codons of the entire DHFR nucleotide sequence to the least frequently used codons in mammals; PASV: simian virus 40 polyA addition signal; and Amp$^r$: selection marker (ampicillin resistance) in *E. coli*.
Figure 8:
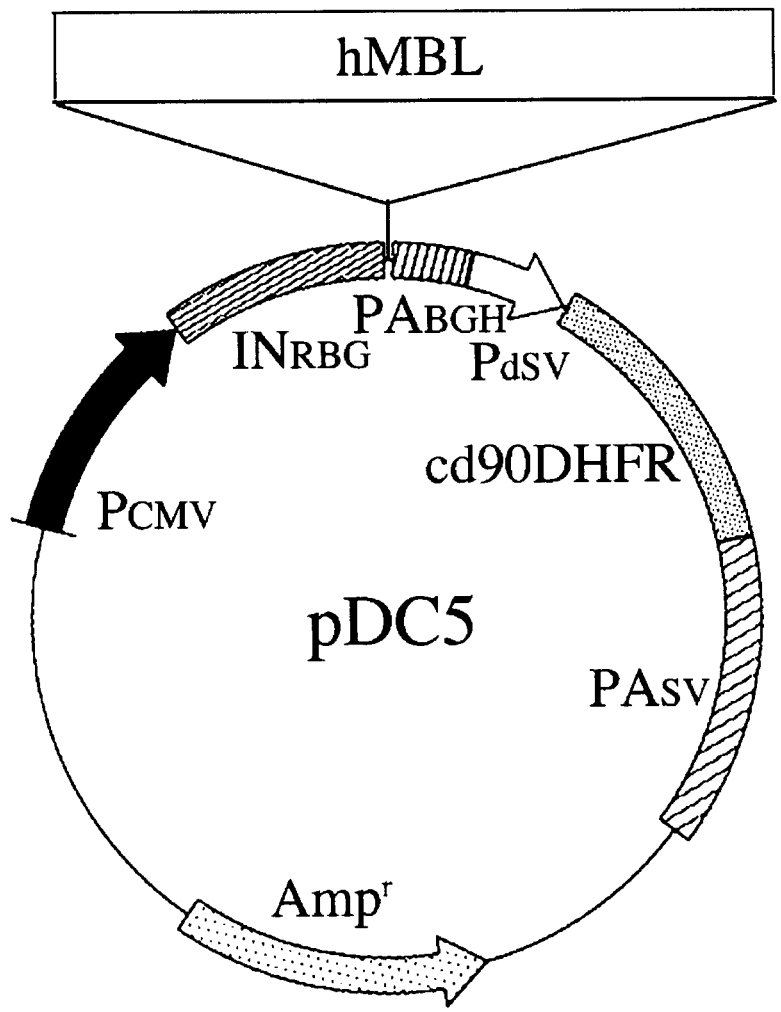
FIG. 8 shows the pDC5/hMBL construct with the respective abbreviations shown below. PCMV: cytomegalovirus promoter; INRBG: rabbit growth hormone intron; hMBL: human mannose-binding lectin cDNA; PABGH: bovine growth hormone gene polyA addition signal; PdSV: enhancer-deleted simian virus 40 promoter; cd90DHFR: translation-impaired DHFR gene produced by altering codons in the range of 90 bases from the 5' end of the nucleotide sequence of DHFR to the least frequently used codons in mammals; PASV: simian virus 40 polyA addition signal; and Amp$^r$: selection marker (ampicillin resistance) in *E. coli*.
Figure 9:
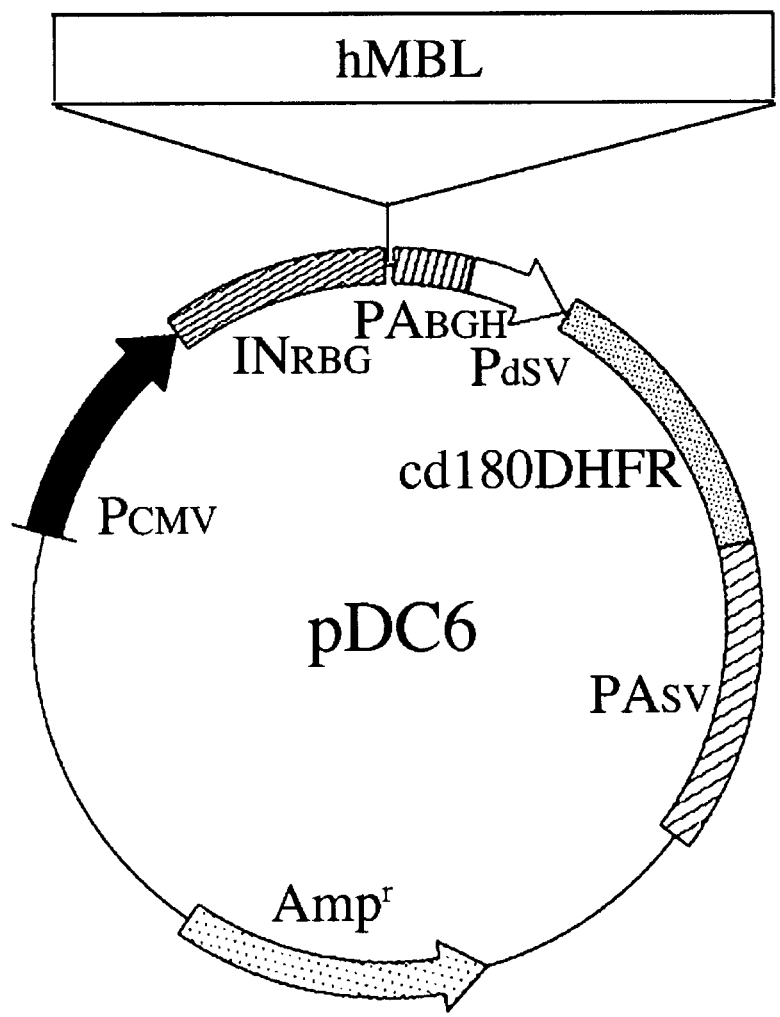
FIG. 9 shows the pDC6/hMBL construct with the respective abbreviations shown below. PCMV: cytomegalovirus promoter; INRBG: rabbit growth hormone intron; hMBL: human mannose-binding lectin cDNA; PABGH: bovine growth hormone gene polyA addition signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA addition signal; and Amp$^r$: selection marker (ampicillin resistance) in *E. coli*.
Figure 10:
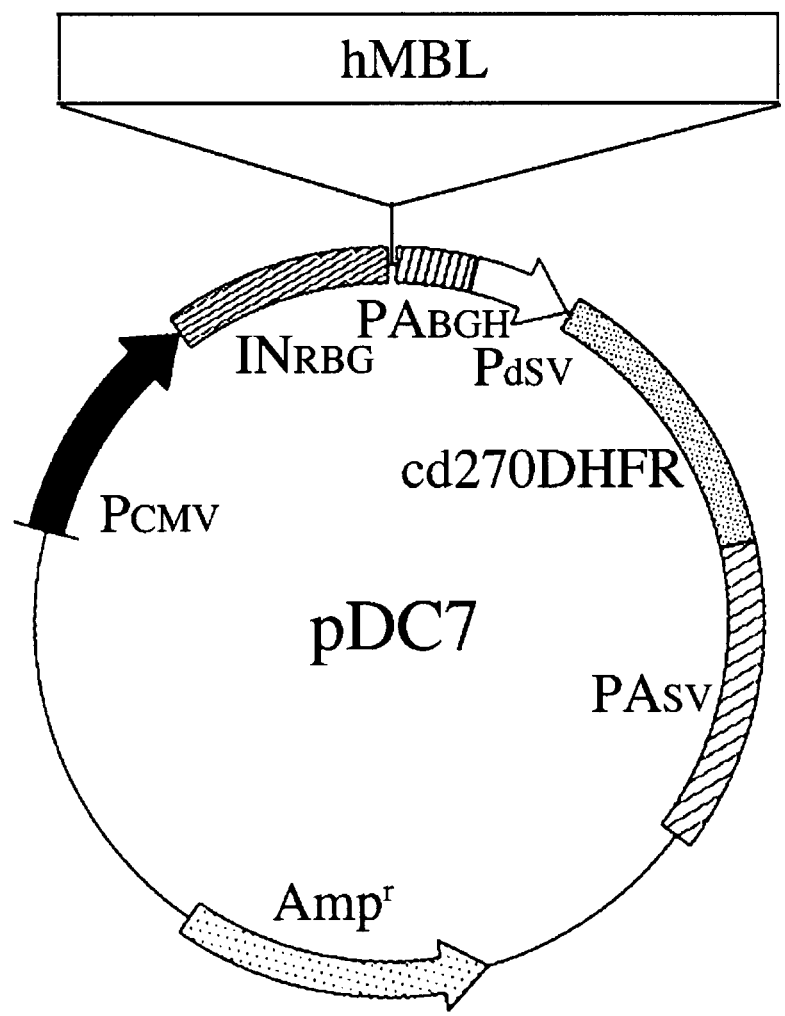
FIG. 10 shows the pDC7/hMBL construct with the respective abbreviations shown below. PCMV: cytomegalovirus promoter; INRBG: rabbit growth hormone intron; hMBL: human mannose-binding lectin cDNA; PABGH: bovine growth hormone gene polyA addition signal; PdSV: enhancer-deleted simian virus 40 promoter; cd270DHFR: translation-impaired DHFR gene produced by altering codons in the range of 270 bases from the 5' end of the nucleotide sequence of DHFR to the least frequently used codons in mammals; PASV: simian virus 40 polyA addition signal; and Amp$^r$: selection marker (ampicillin resistance) in *E. coli*.

Using methods well known to those skilled in the art, nucleotides No. 1267 to No. 1275 in the vectors of the present invention, pDC1, pDC2, pDC5, pDC6, and pDC7, were substituted with a cDNA encoding the human mannan-binding lectin (MBL) of SEQ ID NO: 6 (hereinafter referred to as hMBL), to construct pDC1/hMBL (FIG. 6), pDC2/hMBL (FIG. 7), pDC5/hMBL (FIG. 8), pDC6/hMBL (FIG. 9), and pDC7/hMBL (FIG. 10).

Example 3

Transfection of pDC1/hMBL, pDC2/hMBL, pDC5/hMBL, pDC6/hMBL, and pDC7/hMBL into CHO Cells, and Selection in an HT-Free Medium Using a CD Medium or a CD Medium Supplemented with Non-Animal-Based Additives 10 μg of pDC1/hMBL, pDC2/hMBL, pDC5/hMBL, pDC6/hMBL, and pDC7/hMBL were transfected into 500,000 CHO cells (CHO DG44 cells) in 25 cm²-culture flasks using the Lipofectin method (using Lipofectamine™ LTX; Invitrogen). Gene transfection was performed according to the manufacturer's instructions. 48 hours after gene transfection, the number of cells were counted, and then the cells were diluted in an IS CHO-CD w/Hydrolysate medium (IS Japan) supplemented with 4 mM Gluta MAX™-I (Invitrogen). The cells were plated into five 96-well microtiter plates each at concentrations of 1,000 cells/well and 100 cells/well, a total of 10 plates (960 wells), and after culturing in the presence of 5% carbon dioxide gas at 37° C. for approximately three weeks, viable cells were observed (cell lines growing in HT-free medium). 50 lines from cell lines growing in HT-free medium were arbitrarily selected from the viable cells, transferred to 24-well plates together with the IS CHO-CD w/Hydrolysate medium (IS Japan) supplemented with 4 mM Gluta MAX™-I (Invitrogen), and cultured until the cells occupied ⅓ or more of each well. 0.4 mL of each line was placed into a sterile tube and centrifuged at 200×g for two minutes. The supernatant was discarded, and the cells were suspended in 0.1 mL of fresh medium (IS CHO-CD w/Hydrolysate medium (IS Japan) supplemented with 4 mM Gluta MAX™-I (Invitrogen)). After counting the number of cells, the cells were diluted with the medium to $5\times10^5$ cells/mL, then 0.2 mL of them were transferred to new 24-well plates, and the cells were cultured in the presence of 5% carbon dioxide gas at 37° C. for 72 hours. Then, the cells were centrifuged at 9,300×g for two minutes and the supernatant was collected. Next, the production level of MBL in the culture supernatants was determined.

Example 4

Determination of the MBL Production Levels by pDC1/hMBL, pDC5/hMBL, pDC6/hMBL, and pDC7/hMBL Transfected Cell Lines The production level was assayed by ELISA. 96-well plates (F96 MAXI SORP Nunc-Immunoplate, Cat. no. 442404, Nunc) were coated with 1 μg/mL of an anti-human MBL antibody (gift from Dr. Ohtani at Asahikawa Medical University, Japan) diluted with a coating buffer (15 mM $Na_2CO_3$, 35 mM $NaHCO_3$, 0.05% $NaN_3$, pH 9.6) at 4° C. for 16 hours. After blocking with 4% Block Ace (Dainippon Sumitomo Pharma Co., Ltd.), the 72-hour culture supernatant (1/1,000 to 1/100,000 dilution), two-fold dilution series (20 to 0.3125 ng/mL) of purified human MBL (gift from Dr. Ohtani at Asahikawa Medical University, Japan) in IS CHO-CD w/Hydrolysate medium (IS Japan) which is a serum-free medium for CHO cells, or IS CHO with Hydrolysate medium (IS Japan) was applied to the plates at 100 µL/well, and the plates were incubated at 37° C. for one hour. This was further incubated with 0.1 m/mL of biotinylated human MBL monoclonal antibody (gift from Dr. Ohtani at Asahikawa Medical University, Japan) at 37° C. for one hour. VECTASTAION Elite ABC Kit STANDARD (2 drops of Reagent A, 2 drops of Regent B/5 mL, Vector), which had been incubated at 37° C. for 30 minutes, was applied at 100 µL/well, and this was allowed to react at 37° C. for 45 minutes. PEROXIDASE SUBSTRATE KIT TMB (2 drops of Buffer, 3 drops of TMB, 2 drops of HYDROGEN PEROXIDE/5 mL, Vector), which had been incubated at room temperature for 30 minutes, was further applied at 100 µL/well, and after this was reacted at room temperature for 15 minutes, 1 M phosphoric acid was added at 100 µL/well to stop the reaction. Protein concentration was determined using a microplate reader (Model 680, manufactured by BioRad). Results obtained by the ELISA method, and the top three samples showing high human MBL production levels are shown in Table 1. The cell line with the highest production level showed significantly high productivity compared to the vector with the unaltered codons.

TABLE 1 hMBL PRODUCTION LEVEL OF CELL LINES GROWING IN HT-FREE MEDIA

| CELL LINE NAME | PRODUCTION LEVEL (µg/ml) |
|---|---|
| pDC 1-2 | 20.5 |
| pDC 1-24 | 20.5 |
| pDC 1-50 | 20.0 |
| pDC 5-2 | 10.6 |
| pDC 5-29 | 11.8 |
| pDC 5-82 | 11.3 |
| pDC 6-1 | 51.6 |
| pDC 6-25 | 29.6 |
| pDC 6-49 | 30.0 |
| pDC 7-1 | 33.2 |
| pDC 7-37 | 21.9 |
| pDC 7-43 | 25.8 |

Example 5 hMBL Production Levels by pDC1/hMBL, pDC5/hMBL, pDC6/hMBL, and pDC7/hMBL Transfected Cell Lines The distribution of hMBL expressed by the pDC1, pDC5, pDC6, and pDC7 expression vectors of the present invention in each cell line is shown in Table 2.

For pDC1, among the fifty cell lines growing in HT-free medium, 28.0% produced hMBL at 0 µg/mL or more to less than 5 µg/mL. 36 out of the fifty lines (72.0%) showed production levels of 5 µg/mL or more. 19 out of the fifty lines (38.0%) showed production levels of 10 µg/mL or more. 12 out of the fifty lines (24.0%) showed production levels of 15 µg/mL or more. Two out of the fifty lines (4.0%) showed production levels of 20 µg/mL or more. The line showing the highest production level yielded 20.5 m/mL in 3 days.

For pDC5, among the fifty cell lines growing in HT-free medium, 70.0% produced hMBL at 0 µg/mL or more to less than 5 µg/mL. Fifteen out of the fifty lines (30.0%) showed production levels of 5 µg/mL or more. Three out of the fifty lines (6.0%) showed production levels of 101 µg/mL or more. The line showing the highest production level yielded 11.8 m/mL in 3 days.

For pDC6, among the fifty cell lines growing in HT-free medium, 34.0% produced hMBL at 0 µg/mL or more to less than 5 µg/mL. 33 out of the fifty lines (66.0%) showed production levels of 5 µg/mL or more. 22 out of the fifty lines (44.0%) showed production levels of 10 µg/mL or more. 15 out of the fifty lines (30.0%) showed production levels of 15 µg/mL or more. Seven out of the fifty lines (14.0%) showed production levels of 20 µg/mL or more. Five out of the fifty lines (10.0%) showed production levels of 25 µg/mL or more. Surprisingly, one out of the fifty lines (2.0%) showed a production level of 50 µg/mL or more. The line showing the highest production level yielded 51.6 µg/mL in 3 days.

For pDC7, among the fifty cell lines growing in HT-free medium, 56.0% produced hMBL at 0 µg/mL or more to less than 5 µg/mL. Twenty-two out of the fifty lines (44.0%) showed production levels of 5 µg/mL or more. Sixteen out of the fifty lines (32.0%) showed production levels of 10 µg/mL or more. Thirteen out of the fifty lines (26.0%) showed production levels of 15 µg/mL or more. Eight out of the fifty lines (16.0%) showed production levels of 20 µg/mL or more. Six out of the fifty lines (12.0%) showed production levels of 25 µg/mL or more. Three out of the fifty lines (6.0%) showed production levels of 30 µg/mL or more. Two out of the fifty lines (4.0%) showed production levels of 35 µg/mL or more. Surprisingly, one out of the fifty lines (2.0%) showed a production level of 45 µg/mL or more. The line showing the highest production level yielded 33.2 µg/mL in 3 days.

This was of the highest level when compared to data of early clones before gene amplification by representative expression vectors reported in the literature (DNA, 7, p. 651, 1988; Biotechnology, 10, p. 1455, 1992; Biotechnology, 8, p. 662, 1990; Gene 76, p. 19, 1989; and Biotechnology, 9, p. 64, 1991).

Figure 28:
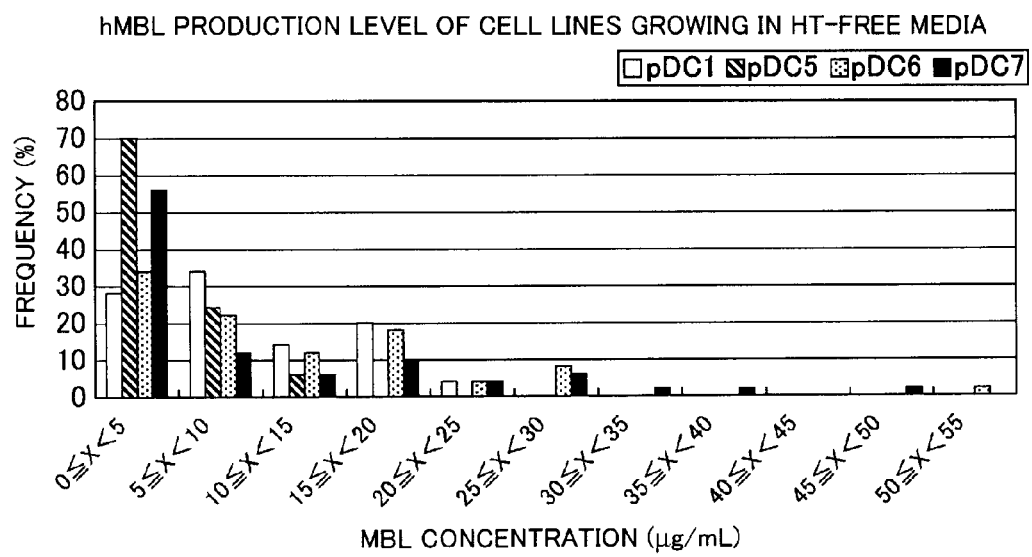
FIG. 28 consists of a Table 2 which is a graph of frequency vs. concentration.

Screening of recombinant cells by gene amplification usually requires six months to a year. Since there are large variations due to culturing conditions and amplification stimulating agent concentrations, it is considered appropriate to compare the primary efficiency of the expression vectors using the pre-amplification expression level of the initial clones. This revealed that the efficiency of the expression vectors of the present invention is very high. The results confirmed that while the vectors of the present invention yield very few lines growing in HT-free medium, they enable establishment of cell lines that are capable of producing high levels of proteins of interest with very high efficiency. This proved that the expression vectors of the present invention enable very high levels of protein expression.
(FIG. 28)

Example 6

Construction of pDC6/hEPO

Figure 11:
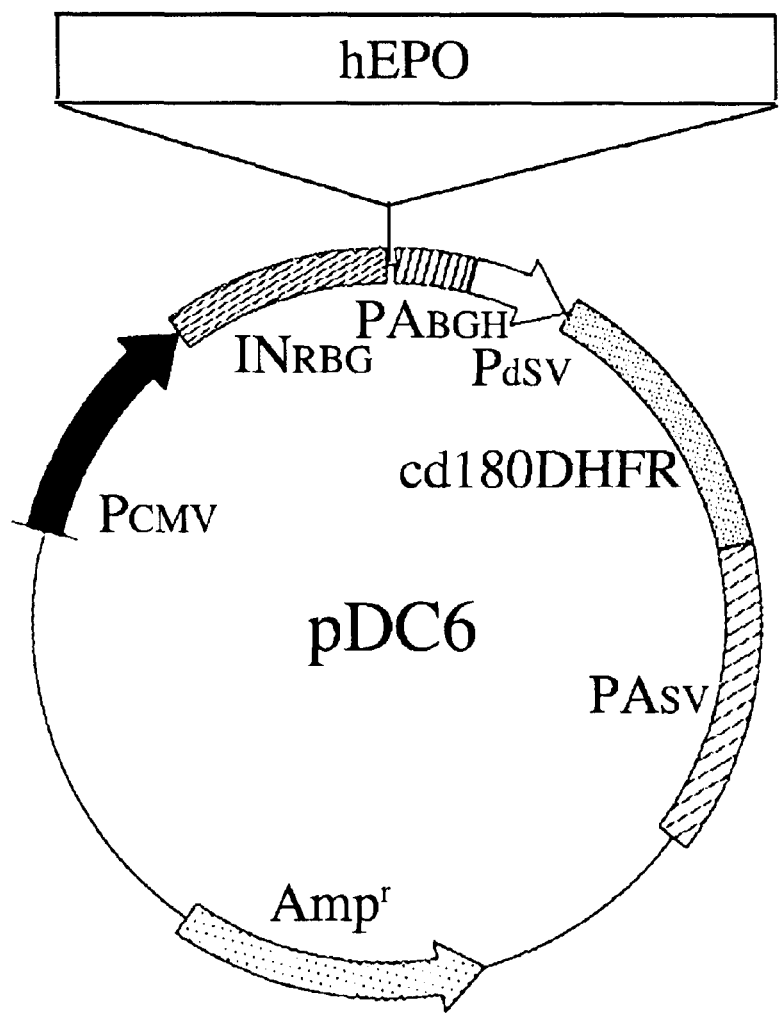
FIG. 11 shows the pDC6/EPO construct with the respective abbreviations shown below. PCMV: cytomegalovirus promoter; INRBG: rabbit growth hormone intron; hEPO: human erythropoietin cDNA; PABGH: bovine growth hormone gene polyA addition signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA addition signal; and Amp$^r$: selection marker (ampicillin resistance) in *E. coli*.

Using methods well known to those skilled in the art, nucleotides No. 1267 to No. 1275 in the vector of the present invention, pDC6, were substituted with a cDNA encoding the human erythropoietin (EPO) of SEQ ID NO: 7 (hereinafter referred to as hEPO), to construct pDC6/hEPO (FIG. 11).

Example 7

Transfection of pDC6/hEPO into CHO Cells, and Selection in an HT-Free Medium using a CD Medium or a CD Medium Supplemented with Non-Animal-Based Additives 2.5 µg of pDC6/hEPO were transfected into 4,000,000 CHO cells (CHO DG44 cells) in 25 cm²-culture flasks using the Lipofectin method (using Lipofectamine™ LTX; Invitrogen). Transfection was performed according to the manufacturer's instructions. 48 hours after gene transfection, the number of cells was counted, and then the cells were diluted in an IS CHO-CD w/Hydrolysate medium (IS Japan) supplemented with 4 mM Gluta MAX™-I (Invitrogen). The cells were plated into five 96-well microtiter plates at a concentration of 4,000 cells/well (480 wells), and after culturing in the presence of 5% carbon dioxide gas at 37° C. for approximately three weeks, viable cells were observed (cell lines growing in HT-free medium).

Figure 12:
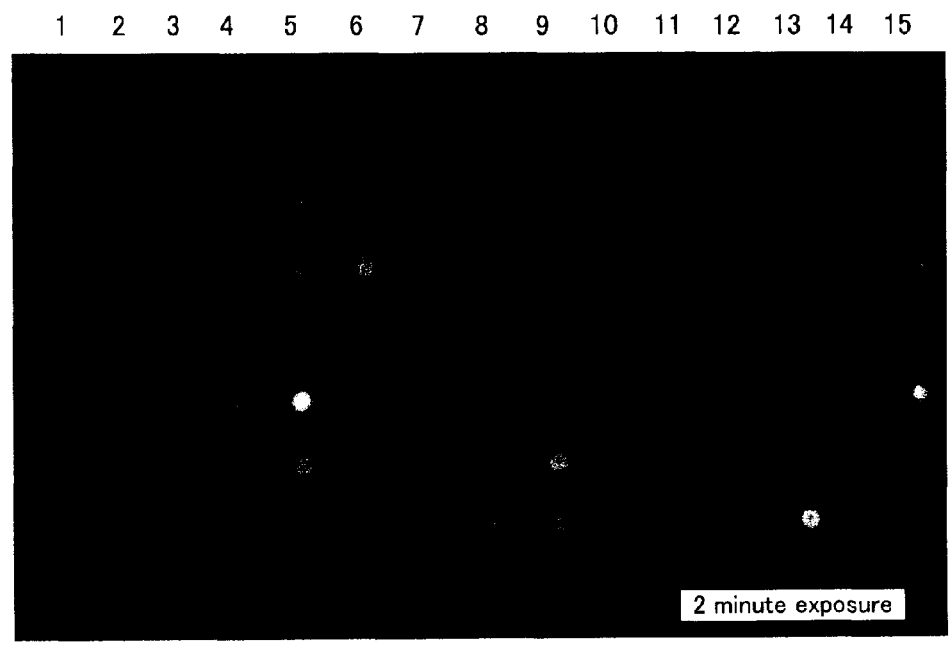
FIG. 12 shows in a chart and a photograph examples of detection of hEPO expressed by CHO cells transfected with the pDC6/hEPO expression vector of the present invention by the dot blot method.

From the viable cells, 82 cell lines growing in HT-free medium were arbitrarily selected, and expression was confirmed by Dotblot. 1 µL each of a two-fold dilution series (10 to 0.16 ng/mL) of a standard preparation of recombinant human EPO (Recombinant Human EPO, Cat. 287-TC, R & D systems) and the culture supernatants of the arbitrarily selected 82 lines were applied to a membrane (Nytran N, ITEM NO. 10416196, SCHLEICHER & SCHUELL). After incubation at room temperature for 30 minutes, this was blocked with 4% Block Ace (Dainippon Sumitomo Pharma Co., Ltd.) at room temperature for 30 minutes. Further, 0.21 µg/mL of a rabbit polyclonal anti-EPO antibody (EPO (H-162), rabbit polyclonal IgG, Cat.sc-7956, Santa Cruz Biotechnology) diluted with PBST (D-PBS, 0.05% Tween 20) was added and this was shaken at room temperature for 30 minutes. 0.2 m/mL of a peroxidase-labeled anti-rabbit IgG antibody (Peroxidase Conjugated Affinity Purified Anti-RABBIT IgG F8c, Cat. 611-1303, Rock Land) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The image obtained by Dotblot is shown in FIG. 12.

The top ten lines having high luminescence intensity in Dotblots were transferred to 24-well plates together with the IS CHO-CD w/Hydrolysate medium (IS Japan) supplemented with 4 mM Gluta MAX™-I (Invitrogen), and cultured until the cells occupied ⅓ or more of each well. 0.4 mL of each line was placed into a sterile tube and centrifuged at 200×g for two minutes. The supernatant was discarded, and the cells were suspended in 0.1 mL of fresh medium (IS CHO-CD w/Hydrolysate medium (IS Japan) supplemented with 4 mM Gluta MAX™-I (Invitrogen)). After counting the number of cells, the cells were diluted with the medium to $5\times10^5$ cells/mL, then 0.2 mL of them were transferred to new 24-well plates, and the cells were cultured in the presence of 5% carbon dioxide gas at 37° C. for 72 hours. Then, the cells were centrifuged at 9,300×g for two minutes and the supernatant was collected. Next, the production level was determined Example 8

Measurement of the Level of hEPO Produced in the pDC6/hEPO-Transfected Cell Lines The production level was determined by ELISA. 96-well plates (F96 MAXI SORP Nunc-Immuno plate, Cat no. 442404, Nunc) were coated at 4° C. for 16 hours with 1 µg/mL of an anti-human EPO antibody (rhEPO MAb R6K, Fuso Pharmaceutical Industries) diluted with a solid phase antibody solution (D-PBS (Dulbecco's phosphate buffer, Sigma-Aldrich)). After blocking with a blocking solution (4% Block Ace (Dainippon Sumitomo Pharma Co., Ltd.) mixed in a 1:3 ratio with D-PBS (Dulbecco's phosphate buffer, Sigma Aldrich)), 100 µL each of 72-hour culture supernatants (1/1000 to 1/100,000 dilution), two-fold dilution series (500 to 15.6 mIU/mL) of purified human EPO (Fuso Pharmaceutical Industries) in antigen antibody diluent (4% Block Ace (Dainippon Sumitomo Pharma Co., Ltd.) mixed in a 1:9 ratio with D-PBS (Dulbecco's phosphate buffer, Sigma Aldrich)), and antigen antibody diluent (4% Block Ace (Dainippon Sumitomo Pharma Co., Ltd.) mixed in a 1:9 ratio with D-PBS (Dulbecco's phosphate buffer, Sigma Aldrich)) were applied, and incubation was carried out at 25° C. for two hours. This was further incubated with 0.1m/mL of a peroxidase-labeled human EPO monoclonal antibody (POD-rhEPO MAb R2C, Fuso Pharmaceutical Industries) at 25° C. for two hours. Sure Blue TMB Microwell Peroxidase Substrate (KPL) was applied at 100 µL/well, and after this was reacted at 25° C. for 30 minutes, 1 M phosphoric acid was added at 100 µL/well to stop the reaction. Protein concentration was determined using a microplate reader (Model 680, manufactured by BioRad) and on the microplate reader, the absorbance was measured at the wavelength of 450 nm with the wavelength of 655 nm as control. Table 3 shows the top ten samples with high human EPO production level according to the results obtained by ELISA. The cell line showing the highest production level yielded 3,727±109 IU/mL in 3 days. This value which comes from an uncloned early-stage cell line, i.e., in a state that has not undergone gene amplification, indicated a very high level compared to representative erythropoietin production levels reported in literature (JP-A (Kokai) 2002-45191; J. Microbiol. Biotechnol. 2008 July; 18(7):1342-1351; Biotechnol. Appl. Biochem. 2000 December; 32 (Pt 3):167-172; Proc. Natl. Acad. Sci. USA. 1986 September; 83(17):6465-6469). This proved that the expression vectors of the present invention enable very high levels of protein expression. Next, Western blotting of hEPO in culture supernatants was carried out to confirm protein expression.

TABLE 3

| pDC6/hEPO Cell Line No. | Converted value IU/mL |
| --- | --- |
| 27 | 547 ± 41 |
| 36 | 1,965 ± 44 |
| 50 | 3,682 ± 155 |
| 60 | 1,989 ± 80 |
| 62 | 2,351 ± 78 |
| 67 | 1,095 ± 42 |
| 72 | 1,558 ± 88 |
| 77 | 3,727 ± 109 |
| 78 | 1,872 ± 150 |
| 82 | 3,727 ± 78 |

Example 9

Western Blotting of Culture Supernatants of pDC6/hEPO-Transfected Cells

Figure 13:
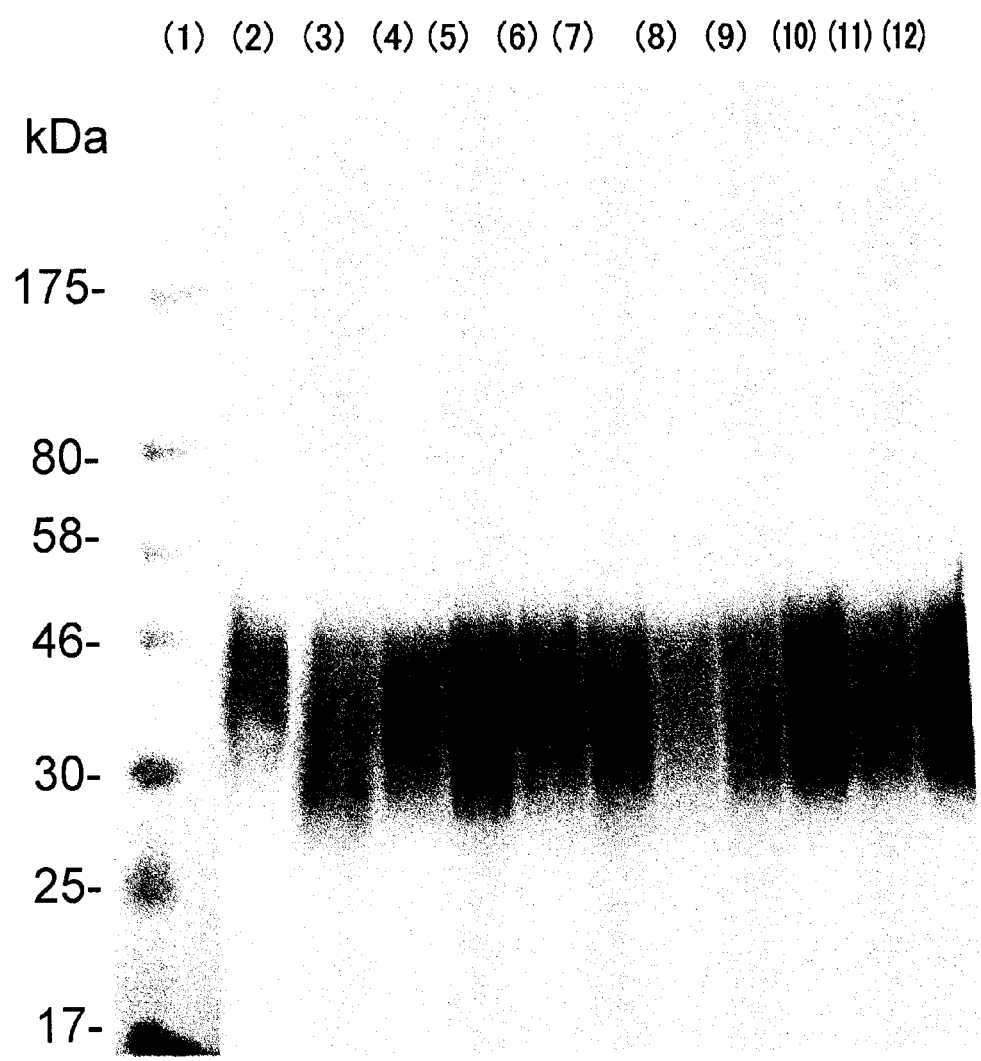
FIG. 13 shows in a photograph examples of detection of hEPO expressed by CHO cells transfected with the pDC6/hEPO expression vector of the present invention by Western blotting. Lane 1: molecular weight marker; lane 2: standard preparation of EPO (R&D systems, 100 ng); lane 3: three-day culture supernatant of Cell Line No. 27; lane 4: three-day culture supernatant of Cell Line No. 36; lane 5: three-day culture supernatant of Cell Line No. 50; lane 6: three-day culture supernatant of Cell Line No. 60; lane 7: three-day culture supernatant of Cell Line No. 62; lane 8: three-day culture supernatant of Cell Line No. 67; lane 9: three-day culture supernatant of Cell Line No. 72; lane 10: three-day culture supernatant of Cell Line No. 77; lane 11: three-day culture supernatant of Cell Line No. 78; and lane 12: three-day culture supernatant of Cell Line No. 82.

Three-day culture supernatants of ten samples with the highest human EPO production level obtained in Example 8 described above were analyzed by Western blotting. 10 µL each of the culture supernatants was mixed with 10 µL of Laemmli Sample Buffer (BIO-RAD) containing 5% 2-mercaptoethnanol (Wako) for reduction by heating at 98° C. for five minutes (TaKaRa PCR Thermal Cycler PERSONAL, TaKaRa BIOMEDICALS). Furthermore, a 100 ng/10 µL standard preparation of rhEPO (Recombinant human EPO, Cat 287-TC, R&D systems) was mixed with 10 μL of Laemmli Sample Buffer (BIO-RAD) containing 5% 2-mercaptoethanol (Wako) for reduction by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 10% to 20% 17 well (Wako) were placed in an electrophoresis vessel (DPE-1020, DAIICHI PURE CHEMICALS CO., LTD), and 20 μL of the heat-treated sample solutions and standard preparation were applied to the Super™ 10% to 20% 17 well (Wako), and electrophoresis was carried out at 40 mA for 55 minutes (power-supply apparatus: My Run, COSMO BIO CO., LTD was used). Then, the gel was removed from the glass plates, and soaked in a transfer buffer (Tris/Glycin Buffer (BIO-RAD) containing 30% methanol (Wako)) while shaking (ROTO-SHAKE GENIE, Scientific Industries) for five minutes. Immobilon-P Transfer Membrane (MILLIPORE) was activated by sequential soaking in 8 mL of methanol (Wako) for 15 seconds, 8 mL of MilliQ water (MILLIPORE) for two minutes, and 8 mL of transfer buffer (Tris/Glycin Buffer (BIO-RAD) containing 30% methanol (Wako)) for five minutes while shaking (ROTO-SHAKE GENIE, Scientific Industries). In a transfer apparatus (TRANS-BLO, SD SEMI-DRY TRANSFER CELL, BIO-RAD), filter papers (Extra Thick Blot Paper Criterion™ Size, BIO-RAD) soaked with transfer buffer (Tris/Glycin Buffer (BIO-RAD) containing 30% methanol (Wako)), the activated Immobilon-P Transfer Membrane (MILLIPORE), the gel after electrophoresis soaked in transfer buffer (Tris/Glycin Buffer (BIO-RAD) containing 30% methanol (Wako)), and filter papers (Extra Thick Blot Paper Criterion™ Size, BIO-RAD) soaked with transfer buffer (Tris/Glycin Buffer (BIO-RAD) containing 30% methanol (Wako)) were laid in order from the cathode side, a cover was placed, and electrophoresis was carried out at 80 mA (PowerPac™ HC, BIO-RAD) for one and half hours to transfer the separated proteins onto the Immobilon-P Transfer Membrane (MILLIPORE). After transfer, the Immobilon-P Transfer Membrane (MILLIPORE) was soaked in 8 mL of ImmunoBlock (registered trademark, Laboratory Products division of Dainippon Sumitomo Pharma Co., Ltd.) and blocked at 4° C. for 18 hours; and 10 mL of Epo (H-162) rabbit polyclonal IgG (Santa Cruz Biotechnology) diluted 1000 times with D-PBS (Wako) containing 0.05% Tween 20 (Polyoxyethylene (20) Sorbitan Monolaurate, Wako) was reacted with the proteins on the membrane for one hour at room temperature while shaking (ROTO-SHAKE GENIE, Scientific Industries). After removing the unbound antibodies, 10 mL of a peroxidase-conjugated affinity purified anti-rabbit IgG F(c) [Goat] (Rock Land) diluted 5000 times with D-PBS (Wako) containing 0.05% Tween 20 (Polyoxyethylene (20) Sorbitan Monolaurate, Wako) was added, and this was reacted for one hour at room temperature while shaking (ROTO-SHAKE GENIE, Scientific Industries). After removing the unbound antibodies, 2 mL of Immobilon™ Western Chemiluminescent HRP Substrate (MILLIPORE) was added for chemiluminescence, and 30-second photographs were taken using Light-Capture ATTO Cooled CCD Camera System (ATTO) at its normal settings. The image obtained by Western blotting is shown in FIG. 13. Bands similar to that of the standard preparation were detected.

Example 10

Measurement of hEPO Production Levels in 7-day Cultures and 14-day Cultures

Cell lines showing high levels of EPO production as well as fast growth (Nos. 27, 36, 50, 78, and 82) were selected and further cultured for 7 and 14 days, and the hEPO concentrations in the culture supernatants were measured. The culturing method involved initially measuring the cell number, diluting the cells with a medium to obtain $0.5 \times 10^5$ cells/mL, then transferring 7.5 mL of this to a new T75 flask, culturing in the presence of 5% carbon dioxide at 37° C. for 7 and 14 days, and collecting the supernatant after centrifugation at 9300 g for two minutes. The production levels were determined by ELISA. 96-well plates (F96 MAXI SORP Nunc-Immuno plate, Cat no. 442404, Nunc) were coated at 4° C. for 16 hours with 1 μg/mL of an anti-human EPO antibody (rhEPO MAb R6K, Fuso Pharmaceutical Industries) diluted with a solid phase antibody solution (D-PBS (Dulbecco's phosphate buffer, Sigma-Aldrich)). After blocking with a blocking solution (4% Block Ace (Dainippon Sumitomo Pharma Co., Ltd.) mixed in a 1:3 ratio with D-PBS (Dulbecco's phosphate buffer, Sigma Aldrich)), 100 μL each of the 7-day and 14-day culture supernatants (1/1,000 to 1/100,000 dilution), two-fold dilution series (500 to 15.6 mIU/mL) of purified human EPO (Fuso Pharmaceutical Industries) in antigen antibody diluent (4% Block Ace (Dainippon Sumitomo Pharma Co., Ltd.) mixed in a 1:9 ratio with D-PBS (Dulbecco's phosphate buffer, Sigma Aldrich)), and antigen antibody diluent (4% Block Ace (Dainippon Sumitomo Pharma Co., Ltd.) mixed in a 1:9 ratio with D-PBS (Dulbecco's phosphate buffer, Sigma Aldrich)) were applied, and incubation was carried out at 25° C. for two hours. This was further incubated with 0.1 m/mL of a peroxidase-labeled human EPO monoclonal antibody (POD-rhEPO MAb R2C, Fuso Pharmaceutical Industries) at 25° C. for two hours. Sure Blue TMB Microwell Peroxidase Substrate (KPL) was applied at 100 μL/well, and after this was reacted at 25° C. for 30 minutes, 1 M phosphoric acid was added at 100 μL/well to stop the reaction. Protein concentration was determined using a microplate reader (Model 680, manufactured by BioRad) and on the microplate reader, the absorbance was measured at the wavelength of 450 nm with the wavelength of 655 nm as control. Table 4 shows the production levels of the 7-day and 14-day cultures in a table according to the results obtained by ELISA. The cell line showing the highest production level yielded 31,590±444 IU/mL in 14 days. This value which comes from an uncloned early-stage cell line, i.e., also in a state that has not undergone gene amplification, indicated a very high level compared to representative erythropoietin production levels reported in literature (JP-A (Kokai) 2002-45191; J. Microbiol. Biotechnol. 2008 July; 18(7):1342-1351; Biotechnol. Appl. Biochem. 2000 December; 32 (Pt 3):167-172; Proc. Natl. Acad. Sci. USA. 1986 September; 83(17):6465-6469). Usually, gene amplification by MTX is carried out after cloning to try to increase the production level; however, the production level of gene-amplified clones is sometimes not stable. Moreover, the screening of recombinant cells from genetic amplification requires six months to a year. In this regard, cells obtained by transfecting the above vector showed a high production level to the extent that gene amplification is not necessary, and cells with high production levels were easily obtained with success and in a short period of time. Accordingly, the vector of the present invention was revealed to have a very high performance.

TABLE 4

| pDC6/hEPO Cell Line No. | EPO production level IU/mL/7 days | EPO production level IU/mL/14 days |
| --- | --- | --- |
| 27 | 3,738 ± 54 | 2,601 ± 61 |
| 36 | 9,310 ± 151 | 18,897 ± 139 |
| 50 | 7,600 ± 489 | 12,167 ± 252 |

TABLE 4-continued

| pDC6/hEPO Cell Line No. | EPO production level IU/mL/7 days | EPO production level IU/mL/14 days |
| --- | --- | --- |
| 78 | 12,210 ± 294 | 31,590 ± 444 |
| 82 | 16,133 ± 396 | 24,949 ± 428 |

Example 11

Generation of High-Yield hEPO-Producing Cell Lines

To generate cells having an even higher production ability, the number of cells in screening was increased in an attempt to generate high-yield hEPO-producing cell lines.

2.5 μg of pDC6/hEPO were transfected into 16,000,000 CHO cells (CHO DG44 cells) in 25 cm²-culture flasks using the Lipofectin method (using Lipofectamine™ LTX; Invitrogen). Transfection was performed according to the manufacturer's instructions. 48 hours after gene transfection, the number of cells was counted, and then the cells were diluted in a CD Opti CHO AGT medium (Invitrogen) supplemented with 4 mM Gluta MAX™-I (Invitrogen). The cells were plated into 45 96-well microtiter plates at a concentration of 16,000 cells/well (4320 wells), and after culturing in the presence of 5% carbon dioxide gas at 37° C. for approximately three weeks, viable cells were observed (cell lines growing in HT-free medium).

Dotblot was used to confirm expression of all lines from the plates onto which cells were plated. 2 μL each of the culture supernatants of all the lines were applied to a membrane (Nytran N, ITEM NO. 10416196, SCHLEICHER & SCHUELL), and after incubation at room temperature for 30 minutes, this was blocked with 4% Block Ace (Dainippon Sumitomo Pharma Co., Ltd.) at room temperature for 30 minutes. Further, 0.2 μg/mL of a rabbit polyclonal anti-EPO antibody (EPO (H-162), rabbit polyclonal IgG, Cat.sc-7956, Santa Cruz Biotechnology) diluted with PBST (D-PBS, 0.05% Tween 20) was added and this was shaken at room temperature for 30 minutes. 0.2 μg/mL of a peroxidase-labeled anti-rabbit IgG antibody (Peroxidase Conjugated Affinity Purified Anti-RABBIT IgG F8c, Cat. 611-1303, Rock Land) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The captured images were analyzed using Image J (NIH) and the luminescence intensities were compared. The 450 lines having the highest luminescence intensity were transferred to 24-well plates together with CD Opti CHO AGT medium (Invitrogen) supplemented with 4 mM Gluta MAX™-I (Invitrogen), and cultured as stationary cultures in the presence of 5% carbon dioxide gas at 37° C. until the cells occupied ⅓ or more of each well.

Expression was confirmed by Dotblot for the top 450 lines. 2 μL each of the culture supernatants of all the lines were applied to a membrane (Nytran N, ITEM NO. 10416196, SCHLEICHER & SCHUELL), and after incubation at room temperature for 30 minutes, this was blocked with 4% Block Ace (Dainippon Sumitomo Pharma Co., Ltd.) at room temperature for 30 minutes. Further, 0.2 μg/mL of a rabbit polyclonal anti-EPO antibody (EPO (H-162), rabbit polyclonal IgG, Cat.sc-7956, Santa Cruz Biotechnology) diluted with PBST (D-PBS, 0.05% Tween 20) was added and this was shaken at room temperature for 30 minutes. 0.2 μg/mL of a peroxidase-labeled anti-rabbit IgG antibody (Peroxidase Conjugated Affinity Purified Anti-RABBIT IgG F8c, Cat. 611-1303, Rock Land) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The captured images were analyzed using Image J (NIH) and the luminescence intensities were compared. The 200 lines having the highest luminescence intensity were transferred to 6-well plates together with a CD Opti CHO AGT medium (Invitrogen) supplemented with 4 mM Gluta MAX™-I (Invitrogen), and cultured while shaking at 90 min$^{-1}$ in the presence of 5% carbon dioxide gas at 37° C. until the cells occupied ⅓ or more of each well.

Expression was confirmed by Dotblot for the top 200 lines. 2 μL each of the culture supernatants of all the lines were applied to a membrane (Nytran N, ITEM NO. 10416196, SCHLEICHER & SCHUELL), and after incubation at room temperature for 30 minutes, this was blocked with 4% Block Ace (Dainippon Sumitomo Pharma Co., Ltd.) at room temperature for 30 minutes. Further, 0.2 m/mL of a rabbit polyclonal anti-EPO antibody (EPO (H-162), rabbit polyclonal IgG, Cat.sc-7956, Santa Cruz Biotechnology) diluted with PBST (D-PBS, 0.05% Tween 20) was added and this was shaken at room temperature for 30 minutes. 0.2 m/mL of a peroxidase-labeled anti-rabbit IgG antibody (Peroxidase Conjugated Affinity Purified Anti-RABBIT IgG F8c, Cat. 611-1303, Rock Land) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The captured images were analyzed using Image J (NIH) and the luminescence intensities were compared. The 80 lines having the highest luminescence intensity were transferred to 6-well plates together with a CD Opti CHO AGT medium (Invitrogen) supplemented with 4 mM Gluta MAX™-I (Invitrogen), and cultured while shaking at 90 min$^{-1}$ at 37° C., 5% $CO_2$, until the cells occupied ⅓ or more of each well. Further, the 80 lines having the highest luminescence intensity were transferred into two wells of 6-well plates together with CD Opti CHO AGT medium (Invitrogen) supplemented with 4 mM Gluta MAX™-I (Invitrogen), and cultured while shaking at 90 min$^{-1}$ at 37° C., 5% $CO_2$, until the cells occupied ⅓ or more of each well. Further, the 80 lines having the highest luminescence intensity were transferred into six wells of 6-well plates together with a CD Opti CHO AGT medium (Invitrogen) supplemented with 4 mM Gluta MAX™-I (Invitrogen), and cultured while shaking at 90 min$^{-1}$ in the presence of 5% carbon dioxide gas at 37° C. until the cells occupied ⅓ or more of each well.

Expression was confirmed by Dotblot for the top 80 lines. 2 μL each of the culture supernatants of all the lines were applied to a membrane (Nytran N, ITEM NO. 10416196, SCHLEICHER & SCHUELL), and after incubation at room temperature for 30 minutes, this was blocked with 4% Block Ace (Dainippon Sumitomo Pharma Co., Ltd.) at room temperature for 30 minutes. Further, 0.2 m/mL of a rabbit polyclonal anti-EPO antibody (EPO (H-162), rabbit polyclonal IgG, Cat.sc-7956, Santa Cruz Biotechnology) diluted with PBST (D-PBS, 0.05% Tween 20) was added and this was shaken at room temperature for 30 minutes. 0.2m/mL of a peroxidase-labeled anti-rabbit IgG antibody (Peroxidase Conjugated Affinity Purified Anti-RABBIT IgG F8c, Cat. 611-1303, Rock Land) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The captured images were analyzed using Image J (NIH) and the luminescence intensities were compared. For the 40 lines having the highest luminescence intensity, 0.4 mL from each line was placed into a sterile tube and centrifuged at 200×g for two minutes. The supernatant was discarded, and the cells were suspended in 0.1 mL of fresh medium (IS CHO-CD w/Hydrolysate medium (IS Japan) supplemented with 4 mM Gluta MAX™-I (Invitrogen)). After counting the cell number, the cells were diluted with the medium to $5\times10^5$ cells/mL, then 0.2 mL of them were transferred to new 24-well plates, and the cells were cultured in the presence of 5% carbon dioxide gas at 37° C. for 72 hours. Then, the cells were centrifuged at 9,300×g for two minutes and the supernatant was collected. The production levels were determined

Example 12

Measurement of the Level of hEPO Produced by High-Yield EPO-Producing Cell Lines The production level was determined by ELISA. 96-well plates (F96 MAXI SORP Nunc-Immuno plate, Cat no. 442404, Nunc) were coated at 4° C. for 16 hours with 1 µg/mL of an anti-human EPO antibody (rhEPO MAb R6K, Fuso Pharmaceutical Industries) diluted with a solid phase antibody solution (D-PBS (Dulbecco's phosphate buffer, Sigma-Aldrich)). After blocking with a blocking solution (4% Block Ace (Dainippon Sumitomo Pharma Co., Ltd.) mixed in a 1:3 ratio with D-PBS (Dulbecco's phosphate buffer, Sigma Aldrich)), 100 µL each of 72-hour culture supernatants (1/40,000 to 1/160,000 dilution), two-fold dilution series (500 to 15.6 mIU/mL) of purified human EPO (Fuso Pharmaceutical Industries) in antigen antibody diluent (4% Block Ace (Dainippon Sumitomo Pharma Co., Ltd.) mixed in a 1:9 ratio with D-PBS (Dulbecco's phosphate buffer, Sigma Aldrich)), and antigen antibody diluent (4% Block Ace (Dainippon Sumitomo Pharma Co., Ltd.) mixed in a 1:9 ratio with D-PBS (Dulbecco's phosphate buffer, Sigma Aldrich)) were applied, and incubation was carried out at 25° C. for two hours. This was further incubated with 0.1 m/mL of a peroxidase-labeled human EPO monoclonal antibody (POD-rhEPO MAb R2C, Fuso Pharmaceutical Industries) at 25° C. for two hours. Sure Blue TMB Microwell Peroxidase Substrate (KPL) was applied at 100 µL/well, and after this was reacted at 25° C. for 30 minutes, 1 M phosphoric acid was added at 100 µL/well to stop the reaction. Protein concentration was determined using a microplate reader (Model 680, manufactured by BioRad) and on the microplate reader, the absorbance was measured at the wavelength of 450 nm with the wavelength of 655 nm as control. Table 5 shows the top 40 samples with high human EPO production level according to the results obtained by ELISA.

TABLE 5

| pDC6/hEPO Cell Line No. | EPO production level IU/mL | pDC6/hEPO Cell Line No. | EPO production level IU/mL |
|---|---|---|---|
| 1 | 2,960 ± 27.8 | 21 | 4,204 ± 159.1 |
| 2 | 2,476 ± 27.8 | 22 | 3,307 ± 144.2 |
| 3 | 6,356 ± 83.9 | 23 | 3,733 ± 70.6 |
| 4 | 7,311 ± 192.5 | 24 | — ± — |
| 5 | 3,142 ± 46.8 | 25 | 4,489 ± 35.3 |
| 6 | 6,889 ± 77.0 | 26 | 12,390 ± 123.1 |
| 7 | 4,684 ± 66.7 | 27 | 2,422 ± 23.1 |
| 8 | 2,631 ± 61.1 | 28 | 2,662 ± 35.3 |
| 9 | 3,387 ± 55.5 | 29 | 1,331 ± 6.7 |
| 10 | 1,416 ± 13.3 | 30 | 1,836 ± 26.7 |
| 11 | 3,347 ± 88.8 | 31 | 804 ± 11.5 |
| 12 | 10,622 ± 277.6 | 32 | 13,744 ± 123.1 |
| 13 | 4,413 ± 68.4 | 33 | 4,356 ± 123.9 |
| 14 | 6,556 ± 126.2 | 34 | 4,084 ± 38.5 |
| 15 | 1,424 ± 13.9 | 35 | 2,013 ± 53.3 |
| 16 | 4,702 ± 116.5 | 36 | 3,596 ± 68.4 |
| 17 | 8,067 ± 66.7 | 37 | 7,241 ± 162.8 |
| 18 | 2,742 ± 65.8 | 38 | 7,056 ± 61.5 |
| 19 | 2,551 ± 101.8 | 39 | 4,231 ± 30.8 |
| 20 | 3,702 ± 126.0 | 40 | 7,262 ± 248.7 |

Of the 40 lines growing in HT-free medium generated by repeating the above screening, 15% produced hEPO at 0 IU/mL/3 days or more to less than 2,000 IU/mL/3 days. Of the 40 lines, 34 lines (85%) produced 2,000 IU/mL/3 days or more. Of the 40 lines, 19 lines (47.5%) produced 4,000 IU/mL/3 days or more. Of the 40 lines, 11 lines (27.5%) produced 6,000 IU/mL/3 days or more. Of the 40 lines, four lines (10%) produced 8,000 IU/mL/3 days or more. Of the 40 lines, three lines (7.5%) produced 10,000 IU/mL/3 days or more. Surprisingly, of the 40 lines, two lines (5.0%) produced 12,000 IU/mL/3 days or more. The line showing the highest production level yielded 13,744±123 IU/mL in 3 days. This value which comes from an uncloned early-stage cell line, i.e., also in a state that has not undergone gene amplification, indicated a very high level compared to representative erythropoietin production levels reported in literature (JP-A (Kokai) 2002-45191; J. Microbiol. Biotechnol. 2008 July; 18(7): 1342-1351; Biotechnol. Appl. Biochem. 2000 December; 32 (Pt 3):167-172; Proc. Natl. Acad. Sci. USA. 1986 September; 83(17):6465-6469). This proved that the expression vectors of the present invention enable very high levels of protein expression.

Example 13

Construction of pDC6/D-EPO

Figure 14:
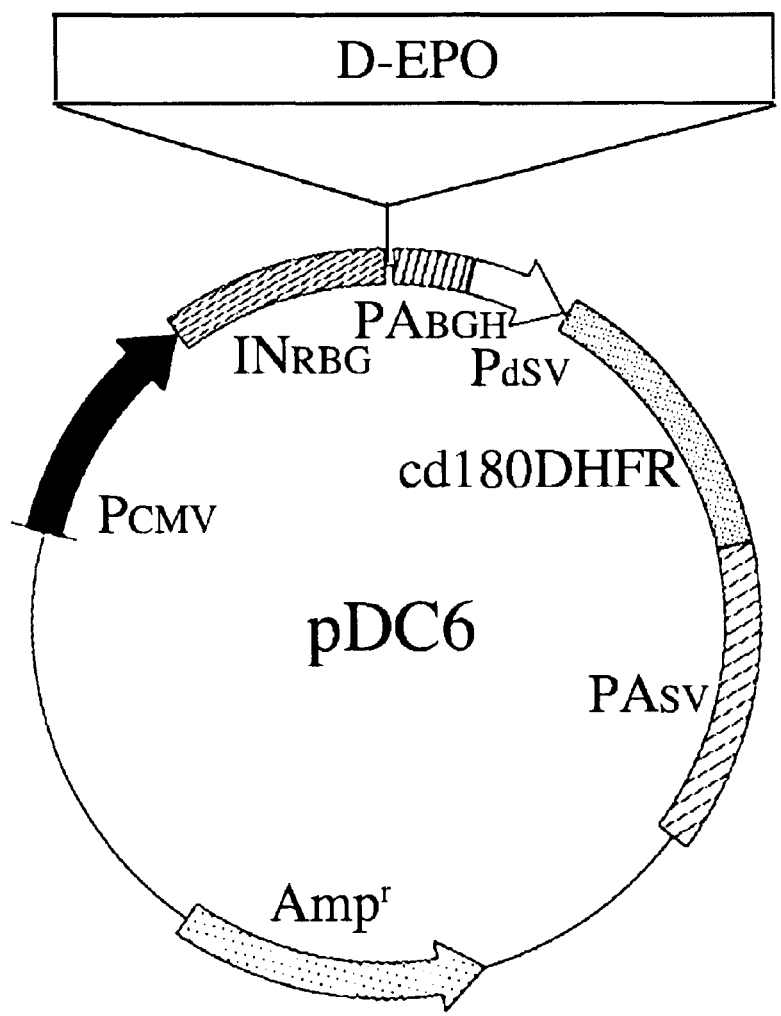
FIG. 14 shows the pDC6/D-EPO construct with the respective abbreviations shown below. PCMV: cytomegalovirus promoter; INRBG: rabbit growth hormone intron; D-EPO: Darbepoetin alpha cDNA; PABGH: bovine growth hormone gene polyA addition signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA addition signal; and Amp$^r$: selection marker (ampicillin resistance) in *E. coli*.

Using methods well known to those skilled in the art, nucleotides No. 1267 to No. 1275 in the vector of the present invention, pDC6, were substituted with a cDNA encoding the Darbepoetin alpha (D-EPO) of SEQ ID NO: 8 (hereinafter referred to as D-EPO) to construct pDC6/D-EPO (FIG. 14).

Example 14

Transfection of pDC6/D-EPO into CHO Cells, and Selection in an HT-Free Medium Using a CD Medium or a CD Medium Supplemented with Non-Animal-Based Additives 2.5 µg of pDC6/D-EPO were transfected into 4,000,000 CHO cells (CHO DG44 cells) in 25 cm²-culture flasks using the Lipofectin method (using Lipofectamine™ LTX; Invitrogen). Transfection was performed according to the manufacturer's instructions. 48 hours after gene transfection, the number of cells was counted, and then the cells were diluted in an IS CHO-CD w/Hydrolysate medium (IS Japan) supplemented with 4 mM Gluta MAX™-I (Invitrogen). The cells were plated into five 96-well microtiter plates at a concentration of 4,000 cells/well (480 wells), and after culturing in the presence of 5% carbon dioxide gas at 37° C. for approximately three weeks, viable cells were observed (cell lines growing in HT-free medium).

Figure 15:
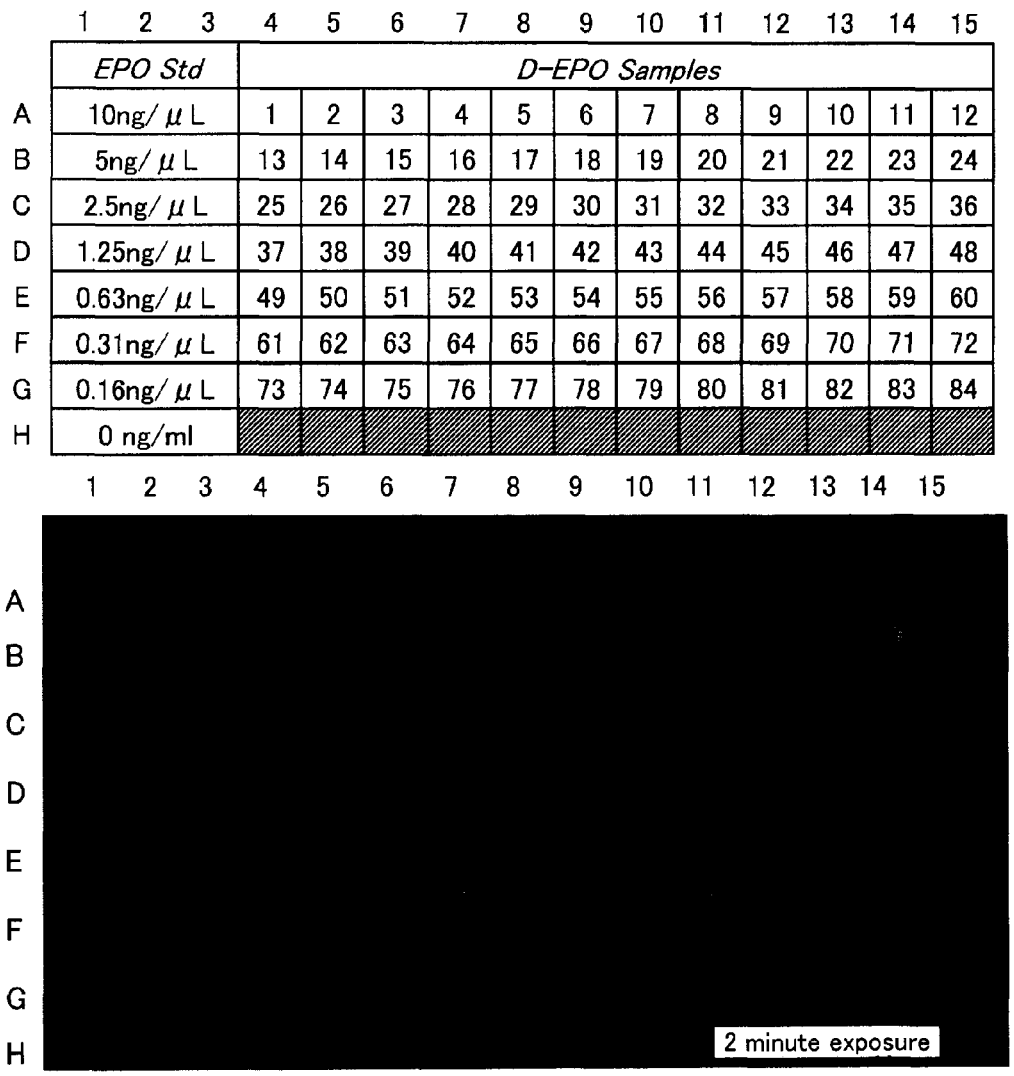
FIG. 15 shows in a chart and a photograph examples of detection of D-EPO expressed by CHO cells transfected with the pDC6/D-EPO expression vector of the present invention by the dot blot method.

From the viable cells, 84 cell lines growing in HT-free medium were arbitrarily selected, and expression was confirmed by Dotblot. 1 µL each of a two-fold dilution series (10 to 0.16 ng/mL) of a standard preparation of recombinant human EPO (Recombinant Human EPO, Cat. 287-TC, R & D systems) and the culture supernatants of the arbitrarily selected 84 lines were applied to a membrane (Nytran N, ITEM NO. 10416196, SCHLEICHER & SCHUELL), and after incubation at room temperature for 30 minutes, this was blocked with 4% Block Ace (Dainippon Sumitomo Pharma Co., Ltd.) at room temperature for 30 minutes. Further, 0.2 µg/mL of a rabbit polyclonal anti-EPO antibody (EPO (H-162), rabbit polyclonal IgG, Cat.sc-7956, Santa Cruz Biotechnology) diluted with PBST (D-PBS, 0.05% Tween 20) was added and this was shaken at room temperature for 30 minutes. 0.2 µg/mL of a peroxidase-labeled anti-rabbit IgG antibody (Peroxidase Conjugated Affinity Purified Anti-RABBIT IgG F8c, Cat. 611-1303, Rock Land) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The image obtained by Dotblot is shown in FIG. 15.

Lines for which luminescence was observed in Dotblots were transferred to 24-well plates together with IS CHO-CD w/Hydrolysate medium (IS Japan) supplemented with 4 mM Gluta MAX™-I (Invitrogen), and cultured until the cells occupied ⅓ or more of each well. Lines for which further growth was observed were transferred to 6-well plates together with IS CHO-CD w/Hydrolysate medium (IS Japan) supplemented with 4 mM Gluta MAX™-I (Invitrogen), and cultured until the cells occupied ⅓ or more of each well. Lines for which further growth was observed were transferred to T75 flasks (BD) together with IS CHO-CD w/Hydrolysate medium (IS Japan) supplemented with 4 mM Gluta MAX™-I (Invitrogen), and cultured until the cells attained $1.0 \times 10^6$ cells/mL or more in each well.

15 mL of each line were placed into a 15 mL tube and centrifuged at 1,100 rpm for seven minutes. The supernatant was discarded, and the cells were suspended in 15 mL of fresh medium (IS CHO-CD w/Hydrolysate medium (IS Japan) supplemented with 4 mM Gluta MAX™-I (Invitrogen)). After counting the cell number, the cells were diluted with the medium to $5 \times 10^5$ cells/mL, then 7.5 mL of them were transferred to new T75 flasks, and the cells were cultured in the presence of 5% carbon dioxide gas at 37° C. for 14 days. On day 3, day 7, and day 14 of culture, 1 mL of each culture solution was collected, centrifuged at 9,300×g for two minutes, and the supernatant was collected. Next, the production level was determined.

Example 15

Measurement of the Level of D-EPO Produced by the pDC6/D-EPO-Transfected Cell Lines The production level was determined by ELISA. 96-well plates (F96 MAXI SORP Nunc-Immuno plate, Cat no. 442404, Nunc) were coated at 4° C. for 16 hours with 1 µg/mL of an anti-human EPO antibody (rEPO MAb R6K, Fuso Pharmaceutical Industries) diluted with a solid phase antibody solution (D-PBS (Dulbecco's phosphate buffer, Sigma-Aldrich)). After blocking with a blocking solution (4% Block Ace (Dainippon Sumitomo Pharma Co., Ltd.) mixed in a 1:3 ratio with D-PBS (Dulbecco's phosphate buffer, Sigma Aldrich)), 100 µL each of 3-day, 7-day, or 14-day culture supernatant (1/1000 to 1/100,000 dilution), two-fold dilution series (10 to 0.156 ng/mL) of Darbepoetin alpha (Nesp injection 120 µg/0.6 mL plastic syringe, Kyowa Hakko Kirin Co. Ltd.) in antigen antibody diluent (4% Block Ace (Dainippon Sumitomo Pharma Co., Ltd.) mixed in a 1:9 ratio with D-PBS (Dulbecco's phosphate buffer, Sigma Aldrich)), and antigen antibody diluent (4% Block Ace (Dainippon Sumitomo Pharma Co., Ltd.) mixed in a 1:9 ratio with D-PBS (Dulbecco's phosphate buffer, Sigma Aldrich)) were applied, and incubation was carried out at 25° C. for two hours. This was further incubated with 0.1 µg/mL of a peroxidase-labeled human EPO monoclonal antibody (POD-rEPO MAb R2C, Fuso Pharmaceutical Industries) at 25° C. for two hours. Sure Blue TMB Microwell Peroxidase Substrate (KPL) was applied at 100 µL/well, and after this was reacted at 25° C. for 30 minutes, 1 M phosphoric acid was added at 100 µL/well to stop the reaction. Protein concentration was determined using a microplate reader (Model 680, manufactured by BioRad) and on the microplate reader, the absorbance was measured at the wavelength of 450 nm with the wavelength of 655 nm as control. Table 6 shows the top five samples with high D-EPO production level according to the results obtained by ELISA. The line showing the highest production level yielded 22±0.3 µg/mL in 3 days, 135±3.3 µg/mL in 7 days, and 170±3.7 µg/mL in 14 days. Next, Western blotting of D-EPO in culture supernatants was carried out to confirm protein expression.

TABLE 6

| pDC6/D-EPO | D-EPO production level | | |
|---|---|---|---|
| Cell Line No. | µg/mL/3 days | µg/mL/7 days | µg/mL/14 days |
| 12 | 14 ± 0.0 | 95 ± 4.8 | 134 ± 1.4 |
| 23 | 14 ± 0.1 | 97 ± 3.5 | 173 ± 2.6 |
| 24 | 12 ± 0.2 | 87 ± 1.5 | 170 ± 1.4 |
| 30 | 22 ± 0.3 | 135 ± 3.3 | 170 ± 3.7 |
| 36 | 20 ± 0.3 | 122 ± 9.6 | 130 ± 3.5 |

Example 16

Western Blotting of Culture Supernatants of pDC6/D-EPO-Transfected Cells 3-day, 7-day, and 14-day culture supernatants of five samples with the highest D-EPO production level obtained in Example 15 described above were analyzed by Western blotting. 10 µL each of the culture supernatants was mixed with 10 µL of Laemmli Sample Buffer (BIO-RAD) containing 5% 2-mercaptoethnanol (Wako) for reduction by heating at 98° C. for five minutes (TaKaRa PCR Thermal Cycler PERSONAL, TaKaRa BIOMEDICALS). Furthermore, a 100 ng/10 µL standard preparation of Darbepoetin alpha (Nesp injection 120 µg/0.6 mL plastic syringe, Kyowa Hakko Kirin Co. Ltd.) was mixed with 10 µL of Laemmli Sample Buffer (BIO-RAD) containing 5% 2-mercaptoethanol (Wako) for reduction by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 10% to 20% 17 well (Wako) were placed in an electrophoresis vessel (DPE-1020, DAIICHI PURE CHEMICALS CO., LTD), and 20 µL of the heat-treated sample solutions and standard preparation were applied to the Super™ 10% to 20% 17 well (Wako), and electrophoresis was carried out at 40 mA for 55 minutes (power-supply apparatus: My Run, COSMO BIO CO., LTD was used). Thereafter, the gel was removed from the glass plates, and soaked in a transfer buffer (Tris/Glycin Buffer (BIO-RAD) containing 30% methanol (Wako)) while shaking (ROTO-SHAKE GENIE, Scientific Industries) for five minutes.

Figure 16:
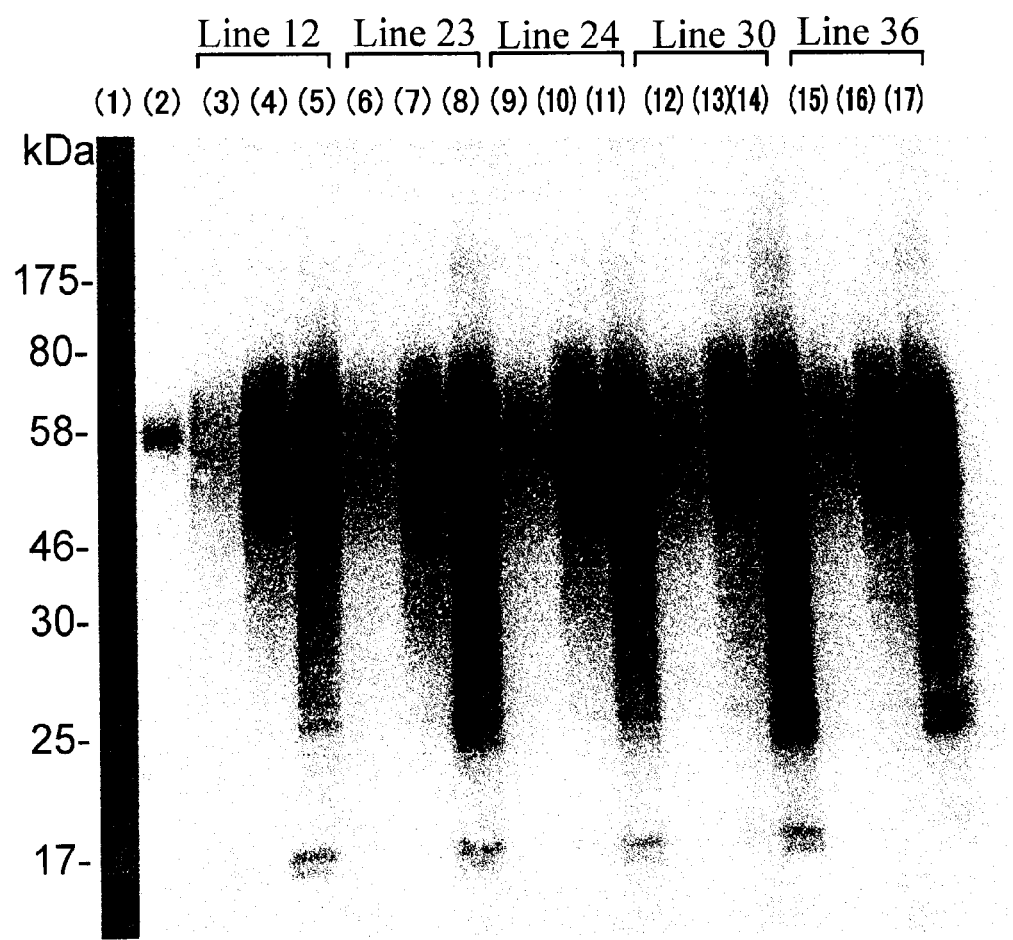
FIG. 16 shows in a photograph examples of detection of D-EPO expressed by CHO cells transfected with the pDC6/D-EPO expression vector of the present invention by Western blotting. Lane 1: molecular weight marker; lane 2: Darbepoetin alpha (Nesp injection 120 μg/0.6 mL plastic syringe, Kyowa Hakko Kirin Co. Ltd., 100 ng); lane 3: 3-day culture supernatant of Cell Line No. 12; lane 4: 7-day culture supernatant of Cell Line No. 12; lane 5: 14-day culture supernatant of Cell Line No. 12; lane 6: 3-day culture supernatant of Cell Line No. 23; lane 7: 7-day culture supernatant of Cell Line No. 23; lane 8: 14-day culture supernatant of Cell Line No. 23; lane 9: 3-day culture supernatant of Cell Line No. 24; lane 10: 7-day culture supernatant of Cell Line No. 24; lane 11: 14-day culture supernatant of Cell Line No. 24; lane 12: 3-day culture supernatant of Cell Line No. 30; lane 13: 7-day culture supernatant of Cell Line No. 30; lane 14: 14-day culture supernatant of Cell Line No. 33; lane 15: 3-day culture supernatant of Cell Line No. 36; lane 16: 7-day culture supernatant of Cell Line No. 36; and lane 17: 14-day culture supernatant of Cell Line No. 36.

Immobilon-P Transfer Membrane (MILLIPORE) was activated by sequential soaking in 8 mL of methanol (Wako) for 15 seconds, 8 mL of MilliQ water (MILLIPORE) for two minutes, and 8 mL of transfer buffer (Tris/Glycin Buffer (BIO-RAD) containing 30% methanol (Wako)) for five minutes while shaking (ROTO-SHAKE GENIE, Scientific Industries). In a transfer apparatus (TRANS-BLO, SD SEMI-DRY TRANSFER CELL, BIO-RAD), filter papers (Extra Thick Blot Paper Criterion™ Size, BIO-RAD) soaked with transfer buffer (Tris/Glycin Buffer (BIO-RAD) containing 30% methanol (Wako)), the activated Immobilon-P Transfer Membrane (MILLIPORE), the gel after electrophoresis soaked in transfer buffer (Tris/Glycin Buffer (BIO-RAD) containing 30% methanol (Wako)), and filter papers (Extra Thick Blot Paper Criterion™ Size, BIO-RAD) soaked with transfer buffer (Tris/Glycin Buffer (BIO-RAD) containing 30% methanol (Wako)) were laid in order from the cathode side, a cover was placed, and electrophoresis was carried out at 80 mA (PowerPac HC™, BIO-RAD) for one and half hours to transfer the separated proteins onto the Immobilon-P Transfer Membrane (MILLIPORE). After transfer, the Immobilon-P Transfer Membrane (MILLIPORE) was soaked in 8 mL of ImmunoBlock (registered trademark, Laboratory Products division of Dainippon Sumitomo Pharma Co., Ltd.) and blocked at 4° C. for 18 hours, and 10 mL of Epo (H-162) rabbit polyclonal IgG (Santa Cruz Biotechnology) diluted 1000 times with D-PBS (Wako) containing 0.05% Tween 20 (Polyoxyethylene (20) Sorbitan Monolaurate, Wako) was reacted with the proteins on the membrane for one hour at room temperature while shaking (ROTO-SHAKE GENIE, Scientific Industries). After removing the unbound antibodies, 10 mL of a peroxidase-conjugated affinity purified anti-rabbit IgG F(c) (Goat) (Rock Land) diluted 5000 times with D-PBS (Wako) containing 0.05% Tween 20 (Polyoxyethylene (20) Sorbitan Monolaurate, Wako) was added and this was reacted for one hour at room temperature while shaking (ROTO-SHAKE GENIE, Scientific Industries). After removing the unbound antibodies, 2 mL of Immobilon™ Western Chemiluminescent HRP Substrate (MILLIPORE) was added for chemiluminescence, and 5-second photographs were taken using Light-Capture ATTO Cooled CCD Camera System (ATTO) at its normal settings. The image obtained by Western blotting is shown in FIG. 16. Bands similar to that of the standard preparation were detected.

Example 17

Construction of pDC6/hG-CSF

Figure 17:
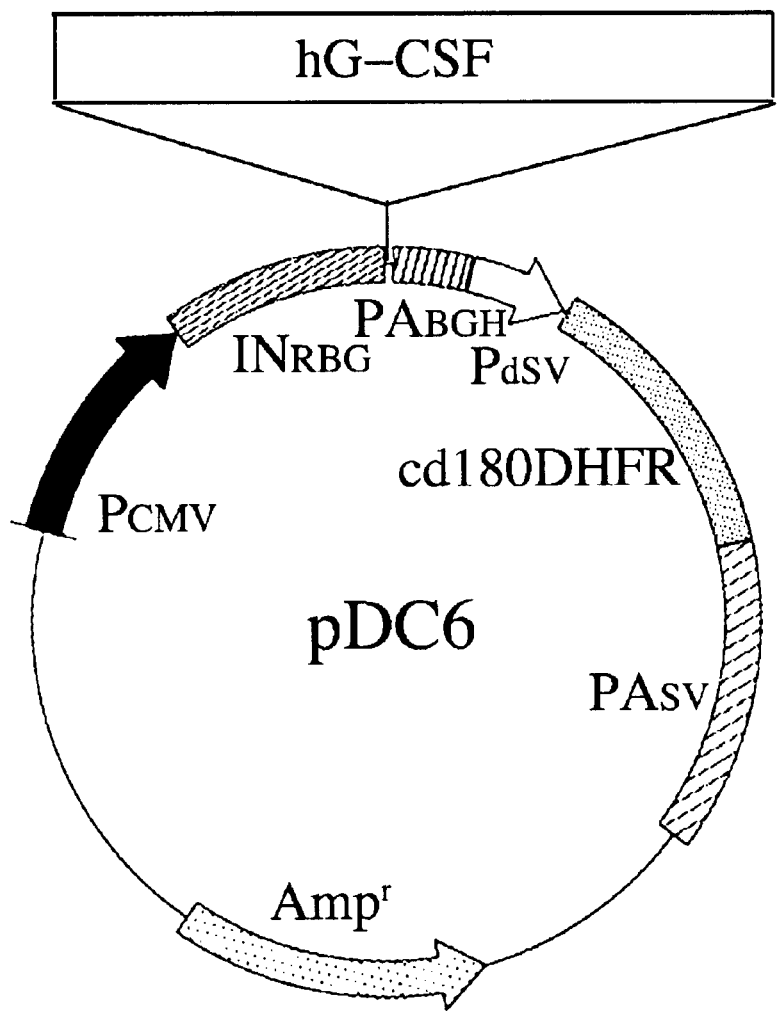
FIG. 17 shows the pDC6/hG-CSF construct with the respective indications shown below. PCMV: cytomegalovirus promoter; INRBG: rabbit growth hormone intron; hG-CSF: human granulocyte colony-stimulating factor (G-CSF) cDNA; PABGH: bovine growth hormone gene polyA addition signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA addition signal; and Amp$^r$: selection marker (ampicillin resistance) in *E. coli*.

Using methods well known to those skilled in the art, nucleotides No. 1267 to No. 1275 in the vector of the present invention, pDC6, were substituted with a cDNA encoding the human granulocyte colony-stimulating factor (G-CSF) of SEQ ID NO: 9 (hereinafter referred to as hG-CSF) to construct pDC6/hG-CSF (FIG. 17).

Example 18

Transfection of pDC6/hG-CSF into CHO Cells, and Selection in an HT-Free Medium Using a CD Medium or a CD Medium Supplemented with Non-Animal-Based Additives 2.5 µg of pDC6/hG-CSF were transfected into 4,000,000 CHO cells (CHO DG44 cells) in 25 cm²-culture flasks using the Lipofectin method (using Lipofectamine™ LTX; Invitrogen). Transfection was performed according to the manufacturer's instructions. 48 hours after gene transfection, the number of cells was counted, and then the cells were diluted in a CD Opti CHO AGT medium (Invitrogen) supplemented with 4 mM Gluta MAX™-I (Invitrogen). The cells were plated into five 96-well microtiter plates at a concentration of 4,000 cells/well (480 wells), and after culturing in the presence of 5% carbon dioxide gas at 37° C. for approximately three weeks, viable cells were observed (cell lines growing in HT-free medium).

Figure 18:
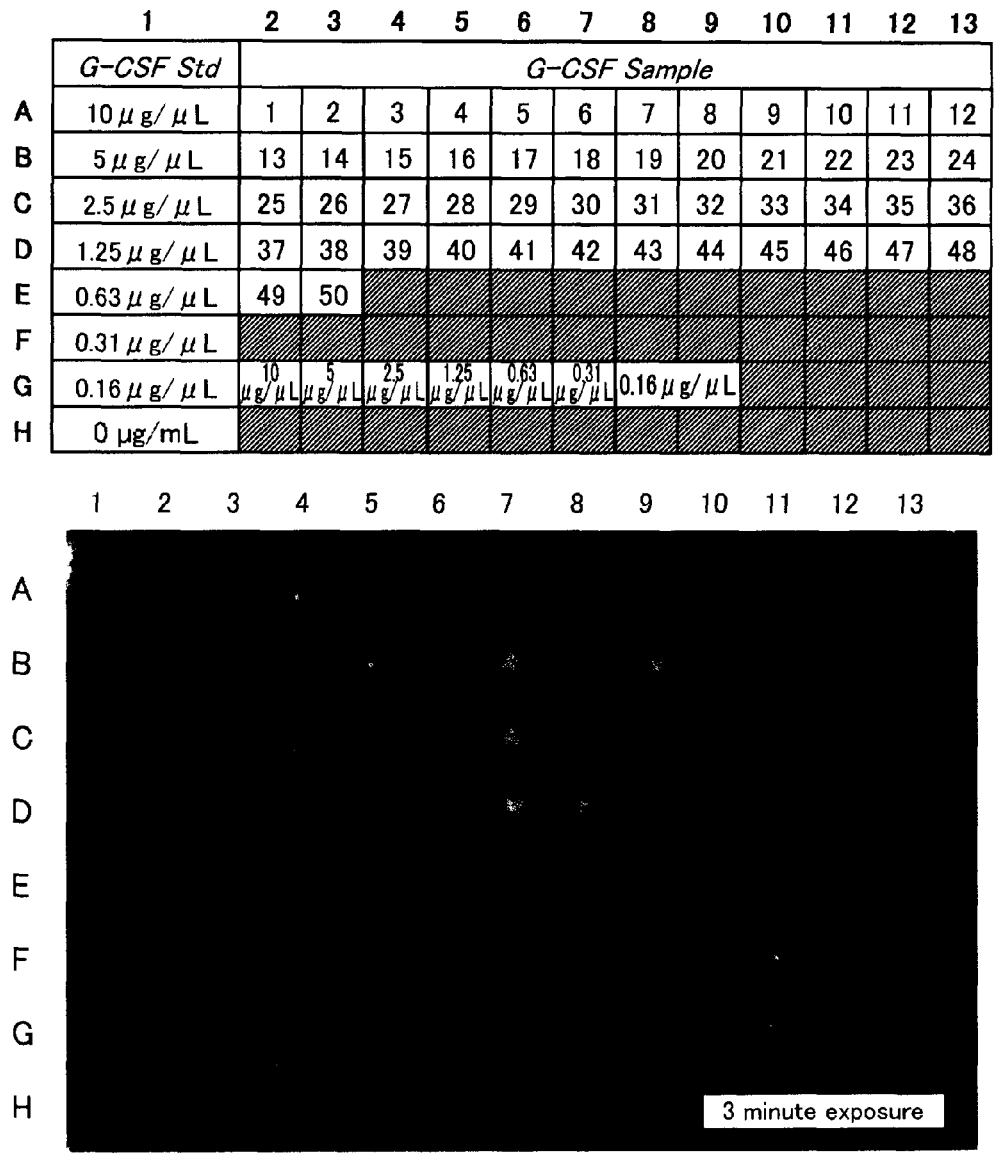
FIG. 18 shows a chart and a photograph indicating examples of detection of hG-CSF expressed by CHO cells transfected with the pDC6/hG-CSF expression vector of the present invention by the dot blot method.

From the viable cells, 50 cell lines growing in HT-free medium were arbitrarily selected, and expression was confirmed by Dotblot. 2 µL each of a two-fold dilution series (10 to 0.0390625 Kg/mL) of a standard preparation of recombinant human G-CSF (Recombinant Human G-CSF, Cat. 1001C, APOLLO) and the culture supernatants of the arbitrarily selected 50 lines were applied to a membrane (Nytran N, ITEM NO. 10416196, SCHLEICHER & SCHUELL), and after incubation at room temperature for 30 minutes, this was blocked with 4% Block Ace (Dainippon Sumitomo Pharma Co., Ltd.) at room temperature for 30 minutes. Further, 0.5 mg/mL of an anti human G-CSF mouse monoclonal antibody (Monoclonal anti-human G-CSF antibody, Cat. MAB214, R & D) diluted with PBST (D-PBS, 0.05% Tween 20) was added and this was shaken at room temperature for 30 minutes. 0.2 Kg/mL of a peroxidase-labeled anti-mouse IgG antibody (goat anti-mouse IgG (H+L), Cat. 115-036-062, Jackson) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The image obtained by Dotblot is shown in FIG. 18.

Lines for which luminescence was observed in Dotblots were transferred to 24-well plates together with CD Opti CHO AGT medium (Invitrogen) supplemented with 4 mM Gluta MAX™-I (Invitrogen), and cultured until the cells occupied ⅓ or more of each well. Lines for which further growth was observed were transferred to 6-well plates together with CD Opti CHO AGT medium (Invitrogen) supplemented with 4 mM Gluta MAX™-I (Invitrogen), and cultured until the cells occupied ⅓ or more of each well. Lines for which further growth was observed were transferred to T75 flasks (BD) together with CD Opti CHO AGT medium (Invitrogen) supplemented with 4 mM Gluta MAX™-I (Invitrogen), and cultured until the cells attained $1.0 \times 10^6$ cells/mL or more in each well.

15 mL of each line were placed into a 15 mL tube and centrifuged at 1,100 rpm for seven minutes. The supernatant was discarded, and the cells were suspended in 15 mL of fresh medium (CD Opti CHO AGT medium (Invitrogen) supplemented with 4 mM Gluta MAX™-I (Invitrogen)). After counting the cell number, the cells were diluted with the medium to $5 \times 10^5$ cells/mL, then 7.5 mL of them were transferred to new T75 flasks, and the cells were cultured in the presence of 5% carbon dioxide gas at 37° C. for 14 days. On day 3, day 7, and day 14 of culture, 1 mL of each culture solution was collected, centrifuged at 9,300×g for two minutes, and the supernatant was collected. The production level was determined Example 19

Measurement of the Level of hG-CSF Produced by the pDC6/hG-CSF-Transfected Cell Lines The production level was determined by ELISA. 96-well plates (F96 MAXI SORP Nunc-Immuno plate, Cat no. 442404, Nunc) were coated at 4° C. for 16 hours with 0.5 μg/mL of an anti-human G-CSF antibody (Anti-human G-CSF monoclonal Antibody, Cat No. MAB214, R&D system) diluted with a coating buffer (15 mM, $Na_2CO_3$, 35 mM $NaHCO_3$, 0.05% $NaN_3$, pH 9.6). After blocking with a blocking solution (4% Block Ace (Dainippon Sumitomo Pharma Co., Ltd.) mixed in a 1:3 ratio with D-PBS (Dulbecco's phosphate buffer, Sigma Aldrich)), 100 μL each of 3-day, 7-day, and 14-day culture supernatants (1/10,000 to 1/200,000 dilution), two-fold dilution series (5 to 0.078125 ng/mL) of a standard preparation of recombinant human G-CSF (Recombinant human G-CSF, Cat 1001C, APOLLO) in antigen antibody diluent (4% Block Ace (Dainippon Sumitomo Pharma Co., Ltd.) mixed in a 1:9 ratio with D-PBS (Dulbecco's phosphate buffer, Sigma Aldrich)), and antigen antibody diluent (4% Block Ace (Dainippon Sumitomo Pharma Co., Ltd.) mixed in a 1:9 ratio with D-PBS (Dulbecco's phosphate buffer, Sigma Aldrich)) were applied, and incubation was carried out at 25° C. for one hour. This was further incubated with 0.25 m/mL of a biotinylated human G-CSF antibody (Biotinylated Anti-human G-CSF Antibody, Cat No BAF214, R&D system) at 25° C. for one hour. Standard Ultra-Sensitive ABC Staining kit (Reagent A 2 drops, Regent B 2 drops/10 mL, Pro#32050, PIERCE) incubated at 25° C. for 30 minutes was applied at 100 μL/well, and reaction was carried out at 25° C. for 30 minutes. Sure Blue TMB Microwell Peroxidase Substrate (KPL) was applied at 100 μL/well, and after this was reacted at 25° C. for 30 minutes, 1 M phosphoric acid was added at 100 μL/well to stop the reaction. Protein concentration was determined using a microplate reader (Model 680, manufactured by BioRad) and on the microplate reader, the absorbance was measured at the wavelength of 450 nm with the wavelength of 655 nm as control. Table 7 shows the top ten samples with high human G-CSF production level according to the results obtained by ELISA. The line showing the highest production level yielded 34.7±1.1 m/mL in 3 days, 193.6±0.6 m/mL in 7 days, and 235.5±14.8 m/mL in 14 days. This value which comes from an uncloned early-stage cell line, i.e., also in a state that has not undergone gene amplification, indicated a very high level compared to representative G-CSF production levels reported in literature (J Biosci Bioeng. 2000, 89(6):534-538; Gene 1996, Nov. 21, 180(1-2):145-150; Mol Biotechnol. 1997 June, 7(3):231-240; Japanese Patent Application Kohyo Publication No. (JP-A) H01-500483 (unexamined Japanese national phase publication corresponding to a non-Japanese international publication)).

This proved that the expression vectors of the present invention enable very high levels of protein expression. Next, Western blotting of hG-CSF in culture supernatants was carried out to confirm protein expression.

TABLE 7

| pDC6/hIG-CSF | G-CSF production level | | |
|---|---|---|---|
| Cell Line No. | μg/mL/3 days | μg/mL/7 days | μg/mL/14 days |
| 3 | 0.6 ± 0.6 | 51.9 ± 1.3 | 68.5 ± 1.7 |
| 6 | 35.7 ± 1.5 | 149.7 ± 0.5 | 180.7 ± 1.6 |
| 7 | 10.5 ± 0.2 | 33.2 ± 0.2 | 27.2 ± 0.3 |
| 13 | 42.6 ± 0.5 | 105.6 ± 0.5 | 96.9 ± 1.4 |
| 14 | 31.2 ± 0.1 | 150.2 ± 0.5 | 188.4 ± 3.1 |
| 15 | 11.5 ± 0.1 | 49.4 ± 0.3 | 49.7 ± 0.6 |
| 16 | 34.7 ± 1.1 | 193.6 ± 0.6 | 235.5 ± 14.8 |
| 17 | 32.7 ± 1.4 | 177.0 ± 0.6 | 231.3 ± 4.4 |
| 19 | 5.8 ± 0.1 | 42.1 ± 1.4 | 70.7 ± 0.5 |
| 20 | 3.1 ± 0.1 | 40.0 ± 0.3 | 65.6 ± 0.7 |

Example 20

Figure 19:
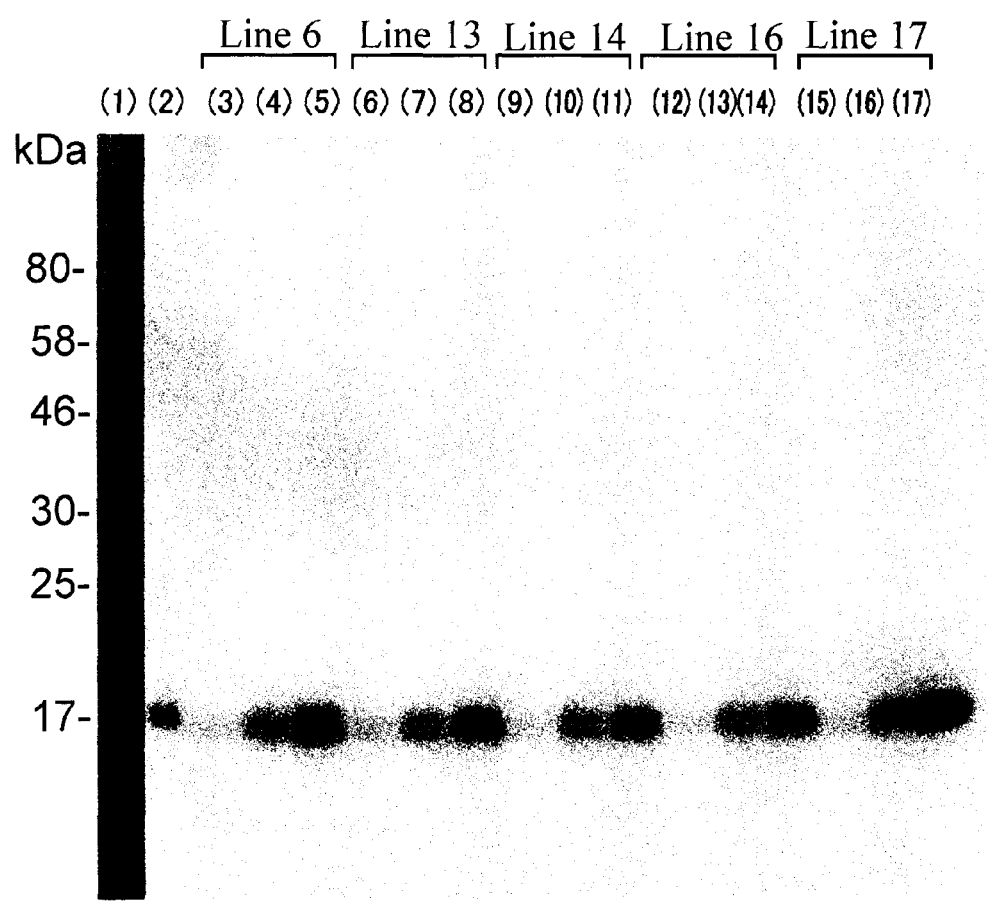
FIG. 19 shows in a photograph examples of detection of hG-CSF expressed by CHO cells transfected with the pDC6/hG-CSF expression vector of the present invention by Western blotting. Lane 1: molecular weight marker; lane 2: standard preparation of human G-CSF (Humanzyme, 50 μg/lane); lane 3: 3-day culture supernatant of Cell Line No. 6; lane 4: 7-day culture supernatant of Cell Line No. 6; lane 5: 14-day culture supernatant of Cell Line No. 6; lane 6: 3-day culture supernatant of Cell Line No. 13; lane 7: 7-day culture supernatant of Cell Line No. 13; lane 8: 14-day culture supernatant of Cell Line No. 13; lane 9: 3-day culture supernatant of Cell Line No. 14; lane 10: 7-day culture supernatant of Cell Line No. 14; lane 11: 14-day culture supernatant of Cell Line No. 14; lane 12: 3-day culture supernatant of Cell Line No. 16; lane 13: 7-day culture supernatant of Cell Line No. 16; lane 14: 14-day culture supernatant of Cell Line No. 16; lane 15: 3-day culture supernatant of Cell Line No. 17; lane 16: 7-day culture supernatant of Cell Line No. 17; and lane 17: 14-day culture supernatant of Cell Line No. 17.

Western Blotting of Culture Supernatants of pDC6/hG-CSF-Transfected Cells 3-day, 7-day, and 14-day culture supernatants of five samples with the highest human G-CSF production level obtained in the above-described Example 19 were analyzed by Western blotting. 10 μL each of the culture supernatants was mixed with 10 μL of Laemmli Sample Buffer (BIO-RAD) containing 5% 2-mercaptoethnanol (Wako) for reduction by heating at 98° C. for five minutes (TaKaRa PCR Thermal Cycler PERSONAL, TaKaRa BIOMEDICALS). Furthermore, a 10 μg/10 μL recombinant human G-CSF standard preparation (Recombinant human G-CSF, Cat 1001C, APOLLO) was mixed with 10 μL of Laemmli Sample Buffer (BIO-RAD) containing 5% 2-mercaptoethanol (Wako) for reduction by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 10% to 20% 17 well (Wako) were placed in an electrophoresis vessel (DPE-1020, DAIICHI PURE CHEMICALS CO., LTD), and 20 μL of the heat-treated sample solutions and standard preparation were applied to the Super™ 10% to 20% 17 well (Wako), and electrophoresis was carried out at 40 mA for 55 minutes (power-supply apparatus: My Run, COSMO BIO CO., LTD was used). Thereafter, the gel was removed from the glass plates, and soaked in a transfer buffer (Tris/Glycin Buffer (BIO-RAD) containing 30% methanol (Wako)) while shaking (ROTO-SHAKE GENIE, Scientific Industries) for five minutes. Immobilon-P Transfer Membrane (MILLIPORE) was activated by sequential soaking in 8 mL of methanol (Wako) for 15 seconds, 8 mL of MilliQ water (MILLIPORE) for two minutes, and 8 mL of transfer buffer (Tris/Glycin Buffer (BIO-RAD) containing 30% methanol (Wako)) for five minutes while shaking (ROTO-SHAKE GENIE, Scientific Industries). In a transfer apparatus (TRANS-BLO, SD SEMI-DRY TRANSFER CELL, BIO-RAD), filter papers (Extra Thick Blot Paper Criterion™ Size, BIO-RAD) soaked with transfer buffer (Tris/Glycin Buffer (BIO-RAD) containing 30% methanol (Wako)), the activated Immobilon-P Transfer Membrane (MILLIPORE), the gel after electrophoresis soaked in transfer buffer (Tris/Glycin Buffer (BIO-RAD) containing 30% methanol (Wako)), and filter papers (Extra Thick Blot Paper Criterion™ Size, BIO-RAD) soaked with transfer buffer (Tris/Glycin Buffer (BIO-RAD) containing 30% methanol (Wako)) were laid in order from the minus side, a cover was placed, and electrophoresis was carried out at 80 mA (PowerPac HC™, BIO-RAD) for one and half hours to transfer the separated proteins onto the Immobilon-P Transfer Membrane (MILLIPORE). After transfer, the Immobilon-P Transfer Membrane (MILLIPORE) was soaked in 8 mL of Immuno-Block (registered trademark, Laboratory Products division of Dainippon Sumitomo Pharma Co., Ltd.) and blocked at 4° C. for 18 hours, and 10 mL of an anti-human G-CSF mouse monoclonal antibody (Monoclonal anti-human G-CSF antibody, Cat MAB214, R & D) diluted 2000 times with D-PBS (Wako) containing 0.05% Tween 20 (Polyoxyethylene (20) Sorbitan Monolaurate, Wako) was reacted with the proteins on the membrane for one hour at room temperature while shaking (ROTO-SHAKE GENIE, Scientific Industries). After removing the unbound antibodies, 10 mL of a peroxidase-labeled anti-mouse IgG antibody (goat anti-mouse IgG (H+L), Cat 115-036-062, Jackson) diluted 5000 times with D-PBS (Wako) containing 0.05% Tween 20 (Polyoxyethylene (20) Sorbitan Monolaurate, Wako) was added and this was reacted for one hour at room temperature while shaking (ROTO-SHAKE GENIE, Scientific Industries). After removing the unbound antibodies, 2 mL of Immobilon™ Western Chemiluminescent HRP Substrate (MILLIPORE) was added for chemiluminescence, and 30-second photographs were taken using Light-Capture ATTO Cooled CCD Camera System (ATTO) at its normal setting. The image obtained by Western blotting is shown in FIG. 19. Bands similar to that of the standard preparation were detected.

Example 21

Construction of pDC6/hGM-CSF

Figure 20:
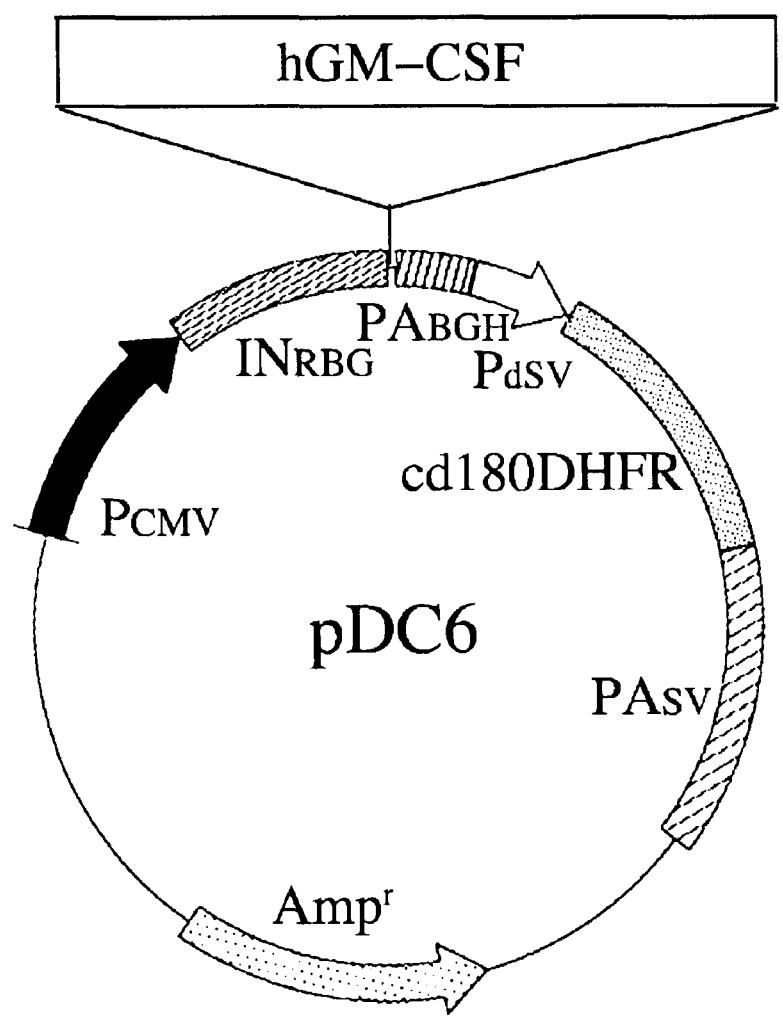
FIG. 20 shows the pDC6/hGM-CSF construct with the respective abbreviations shown below. PCMV: cytomegalovirus promoter; INRBG: rabbit growth hormone intron; hGM-CSF: human granulocyte macrophage colony-stimulating factor (GM-CSF) cDNA; PABGH: bovine growth hormone gene polyA addition signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA addition signal; and Amp$^r$: selection marker (ampicillin resistance) in *E. coli*.

Using methods well known to those skilled in the art, nucleotides No. 1267 to No. 1275 in the vector of the present invention, pDC6, were substituted with a cDNA encoding the human granulocyte macrophage colony-stimulating factor (GM-CSF) of SEQ ID NO: 10 (hereinafter referred to as hGM-CSF) to construct pDC6/hGM-CSF (FIG. 20).

Example 22

Transfection of pDC6/hGM-CSF into CHO Cells, and Selection in an HT-Free Medium Using a CD Medium or a CD Medium Supplemented with Non-Animal-Based Additives 2.5 µg of pDC6/hGM-CSF were transfected into 4,000,000 CHO cells (CHO DG44 cells) in 25 cm²-culture flasks using the Lipofectin method (using Lipofectamine™ LTX; Invitrogen). Transfection was performed according to the manufacturer's instructions. 48 hours after gene transfection, the number of cells was counted, and then the cells were diluted in an IS CHO-CD w/Hydrolysate medium (IS Japan) supplemented with 4 mM Gluta MAX™-I (Invitrogen). The cells were plated into five 96-well microtiter plates at a concentration of 4,000 cells/well (480 wells), and after culturing in the presence of 5% carbon dioxide gas at 37° C. for approximately three weeks, viable cells were observed (cell lines growing in HT-free medium).

Figure 21:
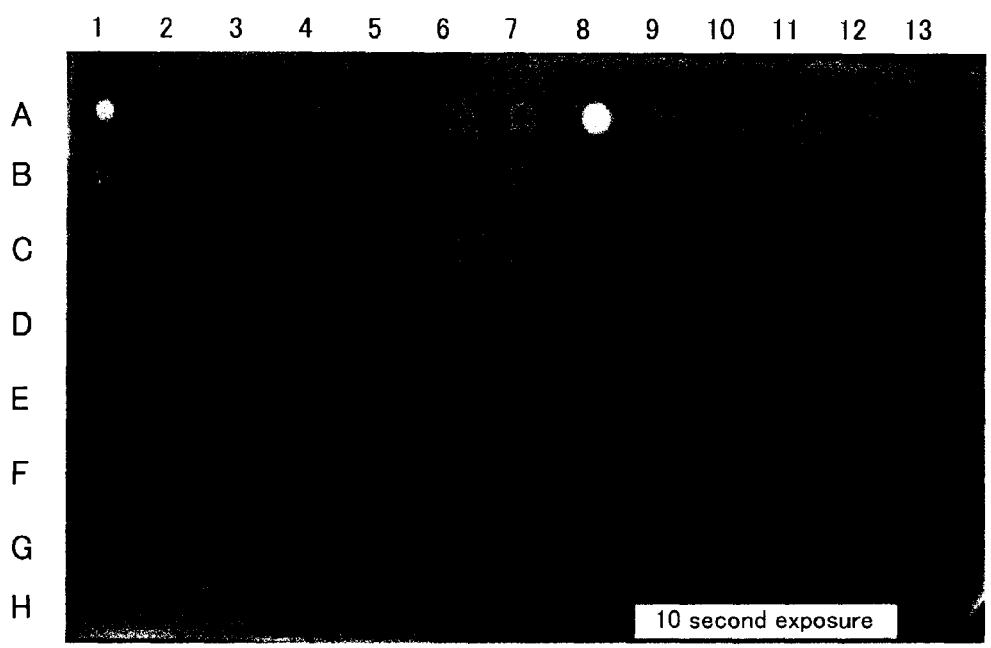
FIG. 21 shows in a chart and a photograph examples of detection of hGM-CSF expressed by CHO cells transfected with the pDC6/hGM-CSF expression vector of the present invention by the dot blot method.

From the viable cells, 48 cell lines growing in HT-free medium were arbitrarily selected, and expression was confirmed by Dotblot. 2 µL each of a two-fold dilution series (100 to 0.16 ng/mL) of a standard preparation of recombinant human GM-CSF (Recombinant Human GM-CSF, Cat No. 071-04111, Wako) and the culture supernatants of the arbitrarily selected 48 lines were applied to a membrane (Nytran N, ITEM NO. 10416196, SCHLEICHER & SCHUELL), and after incubation at room temperature for 30 minutes, this was blocked with 4% Block Ace (Dainippon Sumitomo Pharma Co., Ltd.) at room temperature for 30 minutes. Further, 1 µg/mL of an anti-human GM-CSF goat polyclonal antibody (anti-human GMCSF neutralizing antibody, Cat. AB-215-NA, R & D systems) diluted with PBST (D-PBS, 0.05% Tween 20) was added and this was shaken at room temperature for 30 minutes. 0.2 µg/mL of a peroxidase-labeled anti-goat IgG antibody (Peroxidase Conjugated Affinity Purified Anti-Goat IgG [Rabbit]) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The image obtained by Dotblot is shown in FIG. 21.

Lines for which luminescence was observed in Dotblots were transferred to 24-well plates together with IS CHO-CD w/Hydrolysate medium (IS Japan) supplemented with 4 mM Gluta MAX™-I (Invitrogen), and cultured until the cells occupied ⅓ or more of each well. Lines for which further growth was observed were transferred to 6-well plates together with IS CHO-CD w/Hydrolysate medium (IS Japan) supplemented with 4 mM Gluta MAX™-I (Invitrogen), and cultured until the cells occupied ⅓ or more of each well. Lines for which further growth was observed were transferred to T75 flasks (BD) together with IS CHO-CD w/Hydrolysate medium (IS Japan) supplemented with 4 mM Gluta MAX™-I (Invitrogen), and cultured until the cells attained $1.0 \times 10^6$ cells/mL or more in each well.

15 mL of each line were placed into a 15 mL tube and centrifuged at 1,100 rpm for seven minutes. The supernatant was discarded, and the cells were suspended in 15 mL of fresh medium (IS CHO-CD w/Hydrolysate medium (IS Japan) supplemented with 4 mM Gluta MAX™-I (Invitrogen)). After counting the cell number, the cells were diluted with the medium to $5 \times 10^5$ cells/mL, then 7.5 mL of them were transferred to new T75 flasks, and the cells were cultured in the presence of 5% carbon dioxide gas at 37° C. for 14 days. On day 3, day 7, and day 14 of culture, 1 mL of each culture solution was collected, centrifuged at 9,300×g for two minutes, and the supernatant was collected. The production level was determined Example 23

Measurement of the Level of hGM-CSF Produced by the pDC6/hGM-CSF-Transfected Cell Lines The production level was determined by ELISA. 96-well plates (F96 MAXI SORP Nunc-Immuno plate, Cat no. 442404, Nunc) were coated at 4° C. for 16 hours with 0.5 µg/mL of an anti-human GM-CSF antibody (mouse anti-hGM-CSF capture mAb, Cat No. 404CE14G12, Invitrogen) diluted with a coating buffer (15 mM, $Na_2CO_3$, 35 mM $NaHCO_3$, 0.05% $NaN_3$, pH 9.6). After blocking with a blocking solution (4% Block Ace (Dainippon Sumitomo Pharma Co., Ltd.) mixed in a 1:3 ratio with D-PBS (Dulbecco's phosphate buffer, Sigma Aldrich)), 100 µL each of 72-hour culture supernatants (1/1,000 to 1/25,000 dilution), two-fold dilution series (10 to 0.15625 ng/mL) of recombinant human GM-CSF (Recombinant Human GM-CSF Expressed in Human Cell, Cat No. HZ-1001, HumanZyme Inc.) in antigen antibody diluent (4% Block Ace (Dainippon Sumitomo Pharma Co., Ltd.) mixed in a 1:9 ratio with D-PBS (Dulbecco's phosphate buffer, Sigma Aldrich)), and antigen antibody diluent (4% Block Ace (Dainippon Sumitomo Pharma Co., Ltd.) mixed in a 1:9 ratio with D-PBS (Dulbecco's phosphate buffer, Sigma Aldrich)) were applied, and incubation was carried out at 25° C. for one hour. This was further incubated with 0.25 µg/mL of a biotinylated human GM-CSF antibody (mouse anti-hGM-CSF biotin conjugate, Cat No. 404CE10A8, Invitrogen) at 25° C. for one hour. Standard Ultra-Sensitive ABC Staining kit (Reagent A 2 drops, Regent B 2 drops/10 mL, Pro#32050, PIERCE) incubated at 25° C. for 30 minutes was applied at 100 µL/well, and reaction was carried out at 25° C. for 30 minutes. Sure Blue TMB Microwell Peroxidase Substrate (KPL) was applied at 100 µL/well, and after this was reacted at 25° C. for 30 minutes, 1 M phosphoric acid was added at 100 µL/well to stop the reaction. Protein concentration was determined using a microplate reader (Model 680, manufactured by BioRad) and on the microplate reader, the absorbance was measured at the wavelength of 450 nm with the wavelength of 655 nm as control. Table 8 shows the top six samples with high human GM-CSF production level according to the results obtained by ELISA. The line showing the highest production level yielded 33.1±0.8 µg/mL in 3 days, 171.7±3.0m/mL in 7 days, and 321.7±2.1 µg/mL in 14 days. This value which comes from an uncloned early-stage cell line, i.e., also in a state that has not undergone gene amplification, indicated a very high level compared to representative GM-CSF production levels reported in literature (Journal of Biotechnology 109 (2004) 179-191; Biotechnol. Prog. 2005, 21, 17-21; Eur. J. Biochem. 271, 907-919 (2004); J Biosci Bioeng. 2002, 94(3):271-274).

This proved that the expression vectors of the present invention enable very high levels of protein expression. Next, Western blotting of hGM-CSF in culture supernatants was carried out to confirm protein expression.

TABLE 8

| pDC6/hIGM-CSF | GM-CSF production level | | |
|---|---|---|---|
| Cell Line No. | µg/mL/3 days | µg/mL/7 days | µg/mL/14 days |
| 3 | 24.1 ± 0.6 | 97.2 ± 1.4 | 248.0 ± 4.6 |
| 6 | 9.0 ± 0.2 | 27.0 ± 1.2 | 94.3 ± 0.8 |
| 11 | 15.7 ± 0.2 | 80.2 ± 1.6 | 151.9 ± 5.5 |
| 17 | 7.8 ± 0.1 | 48.6 ± 1.7 | 103.5 ± 2.1 |
| 36 | 33.1 ± 0.8 | 171.7 ± 3.0 | 321.7 ± 2.1 |
| 48 | 14.5 ± 0.9 | 82.8 ± 1.1 | 178.8 ± 3.5 |

Example 24

Figure 22:
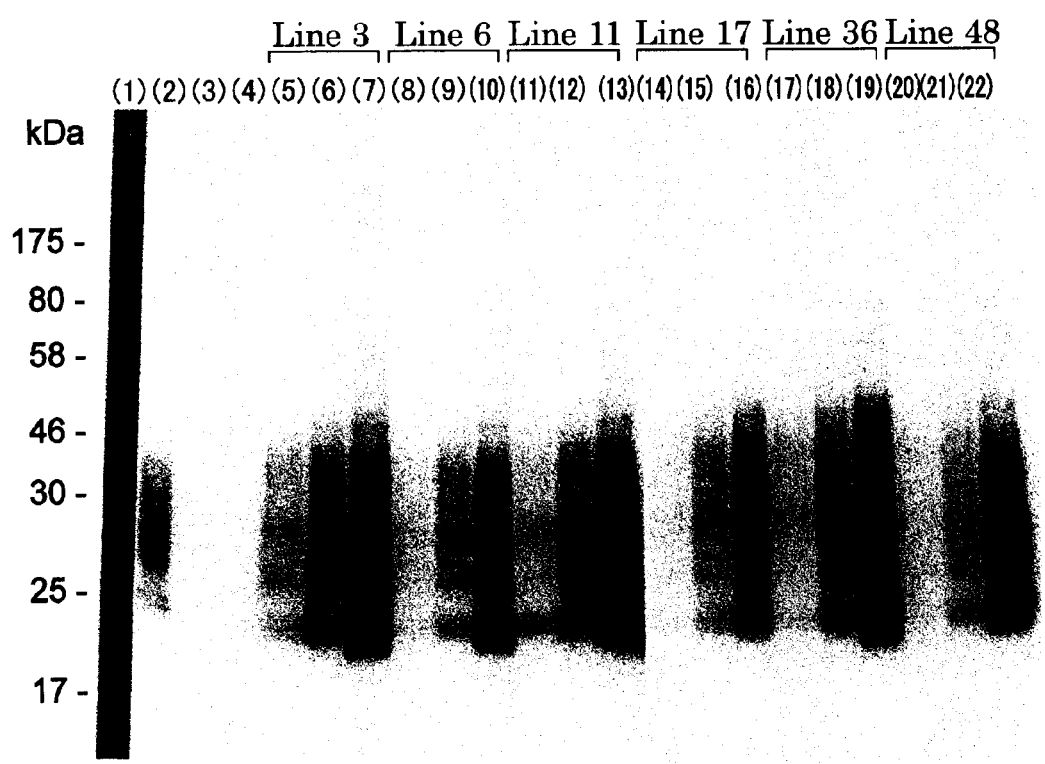
FIG. 22 shows in a photograph examples of detection of hGM-CSF expressed by CHO cells transfected with the pDC6/hGM-CSF expression vector of the present invention by Western blotting. Lane 1: molecular weight marker; lane 2: standard preparation of human GM-CSF (Humanzyme, 5 μg/lane); lane 3: 14-day culture supernatant of CHO DG44 cells; lane 4: sample buffer; lane 5: 3-day culture supernatant of Cell Line No. 3; lane 6: 7-day culture supernatant of Cell Line No. 3; lane 7: 14-day culture supernatant of Cell Line No. 3; lane 8: 3-day culture supernatant of Cell Line No. 6; lane 9: 7-day culture supernatant of Cell Line No. 6; lane 10: 14-day culture supernatant of Cell Line No. 6; lane 11: 3-day culture supernatant of Cell Line No. 11; lane 12: 7-day culture supernatant of Cell Line No. 11; lane 13: 14-day culture supernatant of Cell Line No. 11; lane 14: 3-day culture supernatant of Cell Line No. 17; lane 15: 7-day culture supernatant of Cell Line No. 17; lane 16: 14-day culture supernatant of Cell Line No. 17; lane 17: 3-day culture supernatant of Cell Line No. 36; lane 18: 7-day culture supernatant of Cell Line No. 36; lane 19: 14-day culture supernatant of Cell Line No. 36; lane 20: 3-day culture supernatant of Cell Line No. 48; lane 21: 7-day culture supernatant of Cell Line No. 48; and lane 22: 14-day culture supernatant of Cell Line No. 48.

Western Blotting of Culture Supernatants of pDC6/hGM-CSF-Transfected Cells 3-day, 7-day, and 14-day culture supernatants of six samples with the highest human GM-CSF production level obtained in Example 23 described above were analyzed by Western blotting. 10 µL each of the culture supernatants was mixed with 10 µL of Laemmli Sample Buffer (BIO-RAD) containing 5% 2-mercaptoethnanol (Wako) for reduction by heating at 98° C. for five minutes (TaKaRa PCR Thermal Cycler PERSONAL, TaKaRa BIOMEDICALS). Furthermore, a 10 µg/10 µL human GM-CSF standard preparation (Recombinant Human GM-CSF Expressed in Human Cell, Cat No. HZ-1001, HumanZyme Inc.) was mixed with 10 µL of Laemmli Sample Buffer (BIO-RAD) containing 5% 2-mercaptoethanol (Wako) for reduction by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 10% to 20% 17 well (Wako) were placed in an electrophoresis vessel (DPE-1020, DAIICHI PURE CHEMICALS CO., LTD), and 20 µL of the heat-treated sample solutions and standard preparation were applied to the Super™ 10% to 20% 17 well (Wako), and electrophoresis was carried out at 40 mA for 55 minutes (power-supply apparatus: My Run, COSMO BIO CO., LTD was used). Thereafter, the gel was removed from the glass plates, and soaked in a transfer buffer (Tris/Glycin Buffer (BIO-RAD) containing 30% methanol (Wako)) while shaking (ROTO-SHAKE GENIE, Scientific Industries) for five minutes. Immobilon-P Transfer Membrane (MILLIPORE) was activated by sequential soaking in 8 mL of methanol (Wako) for 15 seconds, 8 mL of MilliQ water (MILLIPORE) for two minutes, and 8 mL of transfer buffer (Tris/Glycin Buffer (BIO-RAD) containing 30% methanol (Wako)) for five minutes while shaking (ROTO-SHAKE GENIE, Scientific Industries). In a transfer apparatus (TRANS-BLO, SD SEMI-DRY TRANSFER CELL, BIO-RAD), filter papers (Extra Thick Blot Paper Criterion™ Size, BIO-RAD) soaked with transfer buffer (Tris/Glycin Buffer (BIO-RAD) containing 30% methanol (Wako)), the activated Immobilon-P Transfer Membrane (MILLIPORE), the gel after electrophoresis soaked in transfer buffer (Tris/Glycin Buffer (BIO-RAD) containing 30% methanol (Wako)), and filter papers (Extra Thick Blot Paper Criterion™ Size, BIO-RAD) soaked with transfer buffer (Tris/Glycin Buffer (BIO-RAD) containing 30% methanol (Wako)) were laid in order from the minus side, a cover was placed, and electrophoresis was carried out at 80 mA (PowerPac HC™, BIO-RAD) for one and half hours to transfer the separated proteins onto the Immobilon-P Transfer Membrane (MILLIPORE). After transfer, the Immobilon-P Transfer Membrane (MILLIPORE) was soaked in 8 mL of ImmunoBlock (registered trademark, Laboratory Products division of Dainippon Sumitomo Pharma Co., Ltd.) and blocked at 4° C. for 18 hours, and 10 mL of an anti-human GM-CSF antibody (anti-human GM-CSF neutralizing antibody, Cat No. AB-215-NA, R & D systems) diluted 2000 times with D-PBS (Wako) containing 0.05% Tween 20 (Polyoxyethylene (20) Sorbitan Monolaurate, Wako) was reacted with the proteins on the membrane for one hour at room temperature while shaking (ROTO-SHAKE GENIE, Scientific Industries). After removing the unbound antibodies, 10 mL of a peroxidase-labeled rabbit anti-goat IgG antibody (peroxidase conjugated affinity purified anti-goat IgG, Cat No. 605-4302, Rock Land) diluted 5000 times with D-PBS (Wako) containing 0.05% Tween 20 (Polyoxyethylene (20) Sorbitan Monolaurate, Wako) was added and this was reacted for one hour at room temperature while shaking (ROTO-SHAKE GENIE, Scientific Industries). After removing the unbound antibodies, 2 mL of Immobilon™ Western Chemiluminescent HRP Substrate (MILLIPORE) was added for chemiluminescence, and 5-second photographs were taken using Light-Capture ATTO Cooled CCD Camera System (ATTO) at its normal settings. The image obtained by Western blotting is shown in FIG. 22. Bands similar to that of the standard preparation were observed, and the intensities of the bands were suggested to be darker in proportion to the number of days of culture.

Example 25

Construction of pDC6/hIFNα

Figure 23:
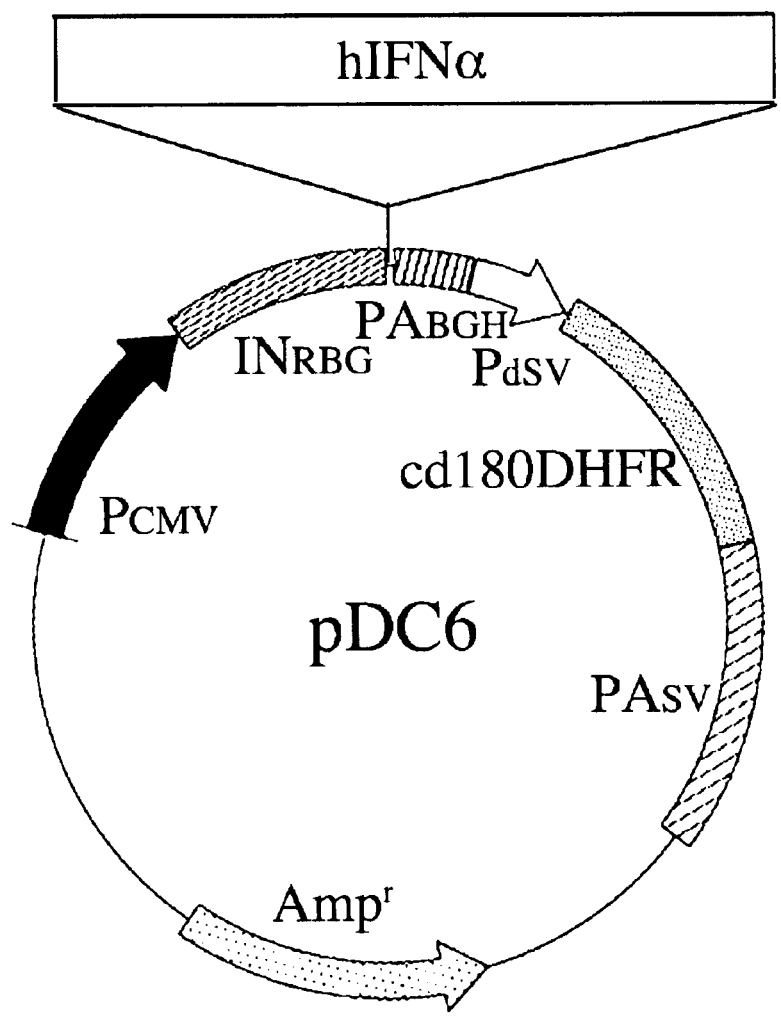
FIG. 23 shows the pDC6/hIFNα construct with the respective abbreviations shown below. PCMV: cytomegalovirus promoter; INRBG: rabbit growth hormone intron; hIFNα: human interferon α2b cDNA; PABGH: bovine growth hormone gene polyA addition signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA addition signal; and Amp$^r$: selection marker (ampicillin resistance) in *E. coli*.

Using methods well known to those skilled in the art, nucleotides No. 1267 to No. 1275 in the vector of the present invention, pDC6, were substituted with a cDNA encoding the human interferon α2b (hIFNα) of SEQ ID NO: 11 (hereinafter referred to as hIFNα) to construct pDC6/hIFNα (FIG. 23).

Example 26

Transfection of pDC6/hIFNα into CHO Cells, and Selection in an HT-Free Medium Using a CD Medium or a CD Medium Supplemented with Non-Animal-Based Additives 2.5 μg of pDC6/hIFNα were transfected into 4,000,000 CHO cells (CHO DG44 cells) in 25 cm²-culture flasks using the Lipofectin method (using Lipofectamine™ LTX; Invitrogen). Transfection was performed according to the manufacturer's instructions. 48 hours after gene transfection, the number of cells was counted, and then the cells were diluted in an IS CHO-CD w/Hydrolysate medium (IS Japan) supplemented with 4 mM Gluta MAX™-I (Invitrogen). The cells were plated into five 96-well microtiter plates at a concentration of 4,000 cells/well (480 wells), and after culturing in the presence of 5% carbon dioxide gas at 37° C. for approximately three weeks, viable cells were observed (cell lines growing in HT-free medium).

Figure 24:
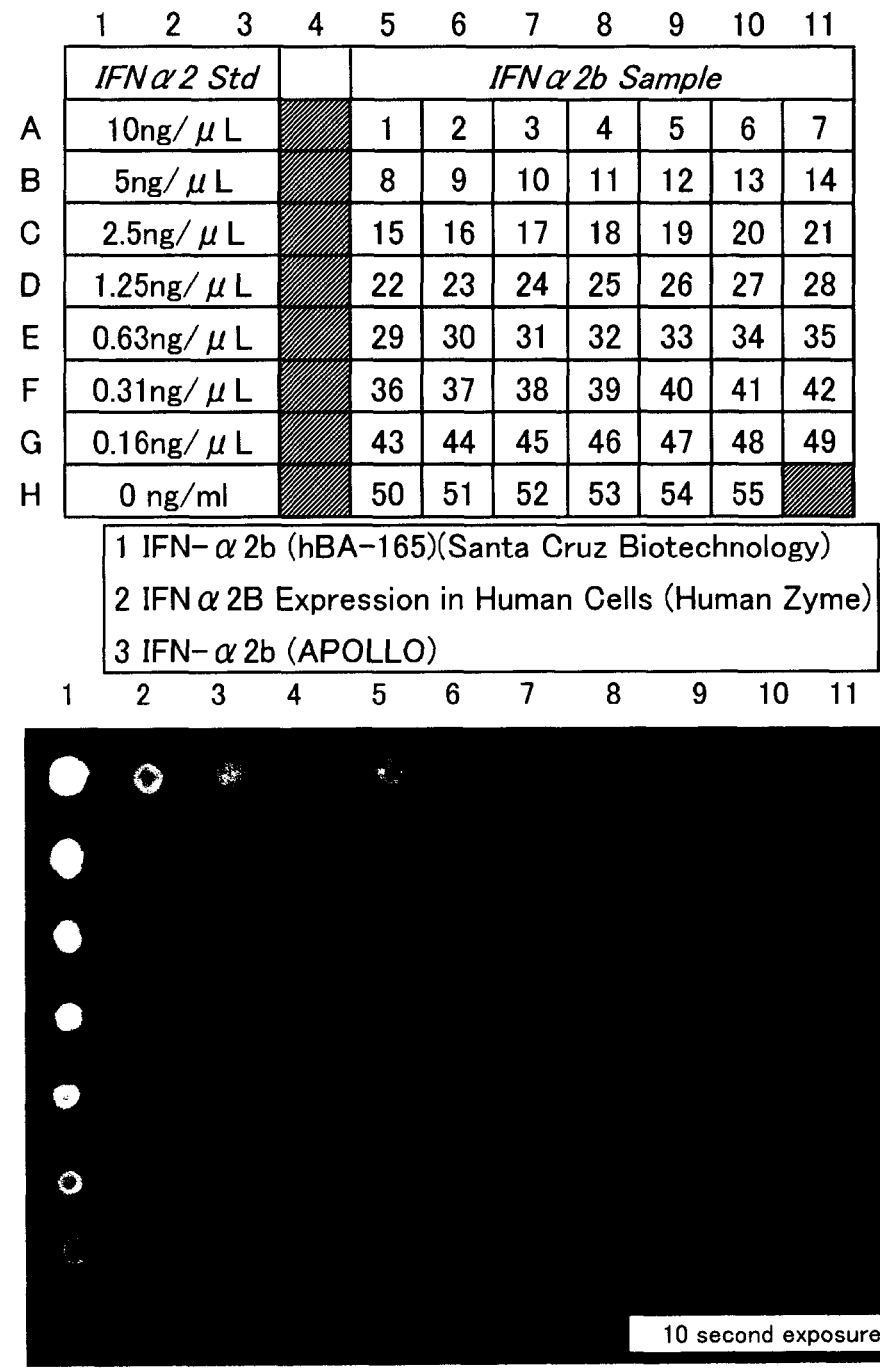
FIG. 24 shows in a chart and a photograph examples of detection of hIFNα expressed by CHO cells transfected with the pDC6/hIFNα expression vector of the present invention by the dot blot method.

From the viable cells, 66 cell lines growing in HT-free medium were arbitrarily selected, and expression was confirmed by Dotblot. 2 μL each of a two-fold dilution series (10 to 0.16 ng/mL) of a standard preparation of recombinant human IFNα2b (IFN-α2b (hBA-165), Cat. sc-4624, Santa Cruz Biotechnology) and IFNα2B Expression in Human Cells, Cat HZ-1072, Human Zyme, IFN-α2b, Cat 5002C, APOLLO) and the culture supernatants of the arbitrarily selected 66 lines were applied to a membrane (Nytran N, ITEM NO. 10416196, SCHLEICHER & SCHUELL), and after incubation at room temperature for 30 minutes, this was blocked with 4% Block Ace (Dainippon Sumitomo Pharma Co., Ltd.) at room temperature for 30 minutes. Further, 1 μg/mL of an anti-human IFNα rabbit polyclonal antibody ((rabbit polyclonal antibody against human interferon alpha (PBL, Cat 31130-1) diluted with PBST (D-PBS, 0.05% Tween 20) was added and this was shaken at room temperature for 30 minutes. 0.2 μg/mL of a peroxidase-labeled anti-rabbit IgG antibody (Peroxidase Conjugated Affinity Purified Anti-RABBIT IgG F8c, Cat. 611-1303, Rock Land) diluted with PBST (D-PBS, 0.05% Tween 20) was added and this was shaken for 30 minutes. Immobilon™ Western Chemiluminescent HRP Substrate (2 mL Luminol Reagent, 2 mL Peroxide Solution, MILLIPORE, Cat.WBKLS0050, MILLIPORE) was reacted at room temperature for five minutes and added. This was incubated at room temperature for five minutes, and chemiluminescence was captured using a detector (ATTO Light-Capture, AE-6981FC, ATTO). The image obtained by Dotblot is shown in FIG. 24.

Lines for which luminescence was observed in Dotblots were transferred to 24-well plates together with IS CHO-CD w/Hydrolysate medium (IS Japan) supplemented with 4 mM Gluta MAX™-I (Invitrogen), and cultured until the cells occupied ⅓ or more of each well. Lines for which further growth was observed were transferred to 6-well plates together with IS CHO-CD w/Hydrolysate medium (IS Japan) supplemented with 4 mM Gluta MAX™-I (Invitrogen), and cultured until the cells occupied ⅓ or more of each well. Lines for which further growth was observed were transferred to T75 flasks (BD) together with IS CHO-CD w/Hydrolysate medium (IS Japan) supplemented with 4 mM Gluta MAX™-I (Invitrogen), and cultured until the cells attained $1.0 \times 10^6$ cells/mL or more in each well.

15 mL of each line were placed into a 15 mL tube and centrifuged at 1,100 rpm for seven minutes. The supernatant was discarded, and the cells were suspended in 15 mL of fresh medium (IS CHO-CD w/Hydrolysate medium (IS Japan) supplemented with 4 mM Gluta MAX™-I (Invitrogen)). After counting the cell number, the cells were diluted with the medium to $5 \times 10^5$ cells/mL, then 7.5 mL of them were transferred to new T75 flasks, and the cells were cultured in the presence of 5% carbon dioxide gas at 37° C. for 14 days. On day 3, day 7, and day 14 of culture, 1 mL of each culture solution was collected, centrifuged at 9,300×g for two minutes, and the supernatant was collected. The production level was determined Example 27

Measurement of the Level of hIFNα Produced by the pDC6/hIFNα-Transfected Cell Lines The production level was determined by ELISA. 96-well plates (F96 MAXI SORP Nunc-Immuno plate, Cat no. 442404, Nunc) were coated at 4° C. for 16 hours with 0.5 m/mL of an anti-human IFNα antibody (Monoclonal Antibody to Human Interferon-α, Pro. 3423-3, MABTECH) diluted with a coating buffer (15 mM, $Na_2CO_3$, 35 mM $NaHCO_3$, 0.05% $NaN_3$, pH 9.6). After blocking with a blocking solution (4% Block Ace (Dainippon Sumitomo Pharma Co., Ltd.) mixed in a 1:3 ratio with D-PBS (Dulbecco's phosphate buffer, Sigma Aldrich)), 100 μL each of 72-hour culture supernatants (1/40,000 to 1/640,000 dilution), two-fold dilution series (80 to 1.25 IU/mL) of recombinant interferon α-2b (Intron A for injection 1,000, Schering Plough) in antigen antibody diluent (4% Block Ace (Dainippon Sumitomo Pharma Co., Ltd.) mixed in a 1:9 ratio with D-PBS (Dulbecco's phosphate buffer, Sigma Aldrich)), and antigen antibody diluent (4% Block Ace (Dainippon Sumitomo Pharma Co., Ltd.) mixed in a 1:9 ratio with D-PBS (Dulbecco's phosphate buffer, Sigma Aldrich)) were applied, and incubation was carried out at 25° C. for one hour. This was further incubated with 0.5 m/mL of a biotinylated human IFNα monoclonal antibody (Monoclonal Antibody to Human Interferon-α Biotin conjugate, Pro. 3423-6, MABTECH) at 25° C. for one hour. Standard Ultra-Sensitive ABC Staining kit (Reagent A 2 drops, Regent B 2 drops/10 mL, Pro#32050, PIERCE) incubated at 25° C. for 30 minutes was applied at 100 μL/well, and reaction was carried out at 25° C. for 30 minutes. Sure Blue TMB Microwell Peroxidase Substrate (KPL) was applied at 100 μL/well, and after this was reacted at 25° C. for 30 minutes, 1 M phosphoric acid was added at 100 μL/well to stop the reaction. Protein concentration was determined using a microplate reader (Model 680, manufactured by BioRad) and on the microplate reader, the absorbance was measured at the wavelength of 450 nm with the wavelength of 655 nm as control. Table 9 shows the top three samples with high human IFNα production level according to the results obtained by ELISA. The line showing the highest production level yielded $(56.3 \pm 5.0) \times 10^4$ IU/mL in 3 days, $(219.3 \pm 11.1) \times 10^4$ IU/mL in 7 days, and $(436.5 \pm 17.1) \times 10^4$ IU/mL in 14 days. This value which comes from an uncloned early-stage cell line, i.e., also in a state that has not undergone gene amplification, indicated a very high level compared to representative IFNα production levels reported in literature (J Gen Virol. 1985 April; 66(Pt 4): 685-691; Nucleic Acids Res. 1983 Feb. 11; 11(3): 555-573; Phil. Trans. R. Soc. Lond. B299, 7-28 (1982); JP-A (Kohyo) 2003-530070).

This proved that the expression vectors of the present invention enable very high levels of protein expression. Next, Western blotting of hIFNα in culture supernatants was carried out to confirm protein expression.

TABLE 9

| pDC6/hIFN α 2b Cell Line No. | IFNα2b production level ×10⁴ IU/mL/3 days | IFNα2b production level ×10⁴ IU/mL/7 days | IFNα2b production level ×10⁴ IU/mL/14 days |
| --- | --- | --- | --- |
| 3rd-8 | 31.4 ± 1.2 | 127.9 ± 8.2 | 371.4 ± 10.3 |
| 3rd-14 | 16.7 ± 1.2 | 94.6 ± 0.9 | 252.8 ± 5.1 |
| 2nd-12 | 56.3 ± 5.0 | 219.3 ± 11.1 | 436.5 ± 17.1 |

Example 28

Figure 25:
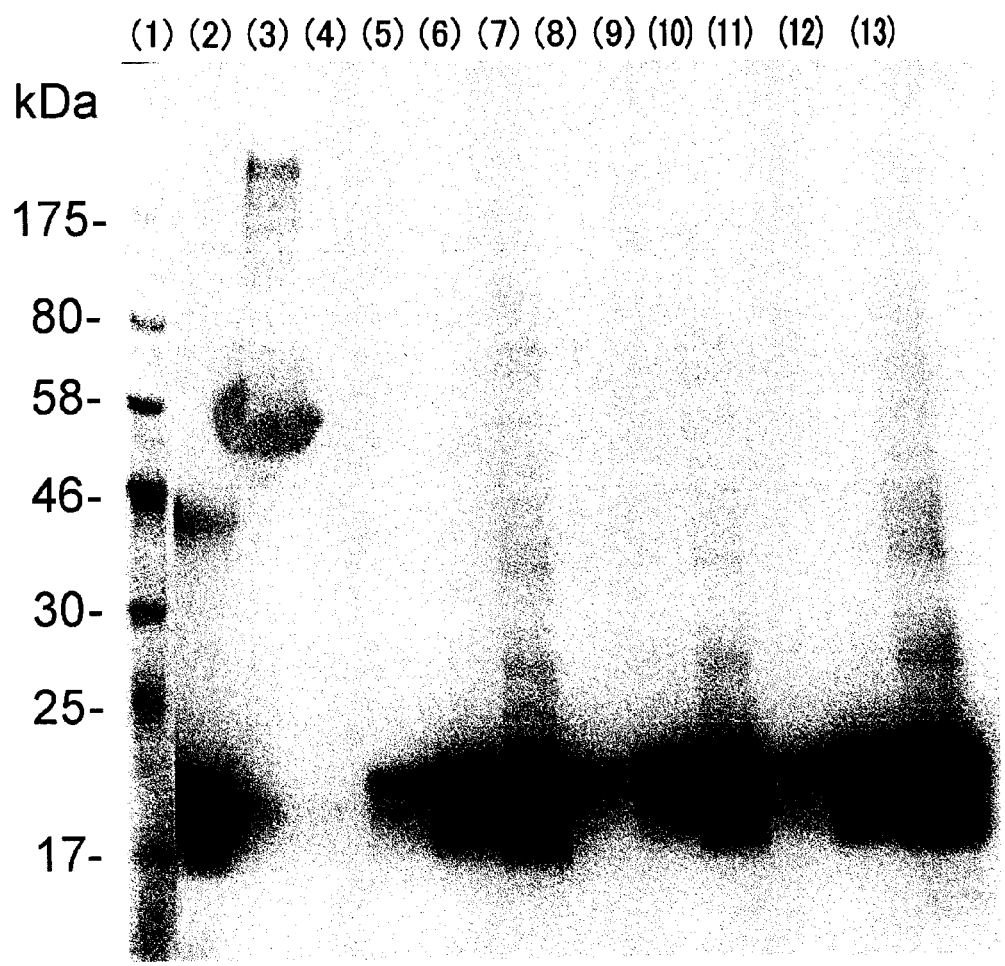
FIG. 25 shows in a photograph examples of detection of hIFNα expressed by CHO cells transfected with the pDC6/hIFNα expression vector of the present invention by Western blotting. Each of the following are indicated: lane 1: molecular weight marker; lane 2: standard preparation of human IFNα (IFNα2B Expression in Human Cells, Cat HZ-1072, Human Zyme, IFN-α2b); lane 3: standard preparation of human IFNα (iLite™ Alphabeta IFN stock solution (200 IU/ml), biomonitor); lane 4: 14-day culture supernatant of CHO DG44 cells; lane 5: 3-day culture supernatant of Cell Line No. 3rd-8; lane 6: 7-day culture supernatant of Cell Line No. 3rd-8; lane 7: 14-day culture supernatant of Cell Line No. 3rd-8; lane 8: 3-day culture supernatant of Cell Line No. 3rd-14; lane 9: 7-day culture supernatant of Cell Line No. 3rd-14; lane 10: 14-day culture supernatant of Cell Line No. 3rd-14; lane 11: 3-day culture supernatant of Cell Line No. 2nd-12; lane 12: 7-day culture supernatant of Cell Line No. 2nd-12; and lane 13: 14-day culture supernatant of Cell Line No. 2nd-12.

Western Blotting of Culture Supernatants of pDC6/hIFNα-Transfected Cells 3-day, 7-day, and 14-day culture supernatants of ten samples with the highest human hIFNα production level obtained in Example 27 described above were analyzed by Western blotting. 10 μL each of the culture supernatants was mixed with 10 μL of Laemmli Sample Buffer (BIO-RAD) containing 5% 2-mercaptoethnanol (Wako) for reduction by heating at 98° C. for five minutes (TaKaRa PCR Thermal Cycler PERSONAL, TaKaRa BIOMEDICALS). Furthermore, a 10 μg/10 μL standard preparation of human IFNα (IFNα2B Expression in Human Cells, Cat HZ-1072, Human Zyme, IFN-α2b) and a 200 IU/mL/10 μL standard preparation of human IFNα (iLite™ Alphabeta IFN stock solution (200 IU/mL), biomonitor) were mixed with 10 μL of Laemmli Sample Buffer (BIO-RAD) containing 5% 2-mercaptoethanol (Wako) for reduction by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 10% to 20% 17 well (Wako) were placed in an electrophoresis vessel (DPE-1020, DAIICHI PURE CHEMICALS CO., LTD), and 20 μL of the heat-treated sample solutions and standard preparation were applied to the Super™ 10% to 20% 17 well (Wako), and electrophoresis was carried out at 40 mA for 55 minutes (power-supply apparatus: My Run, COSMO BIO CO., LTD was used). Thereafter, the gel was removed from the glass plates, and soaked in a transfer buffer (Tris/Glycin Buffer (BIO-RAD) containing 30% methanol (Wako)) while shaking (ROTO-SHAKE GENIE, Scientific Industries) for five minutes. Immobilon-P Transfer Membrane (MILLIPORE) was activated by sequential soaking in 8 mL of methanol (Wako) for 15 seconds, 8 mL of MilliQ water (MILLIPORE) for two minutes, and 8 mL of transfer buffer (Tris/Glycin Buffer (BIO-RAD) containing 30% methanol (Wako)) for five minutes while shaking (ROTO-SHAKE GENIE, Scientific Industries). In a transfer apparatus (TRANS-BLO, SD SEMI-DRY TRANSFER CELL, BIO-RAD), filter papers (Extra Thick Blot Paper Criterion™ Size, BIO-RAD) soaked with transfer buffer (Tris/Glycin Buffer (BIO-RAD) containing 30% methanol (Wako)), the activated Immobilon-P Transfer Membrane (MILLIPORE), the gel after electrophoresis soaked in transfer buffer (Tris/Glycin Buffer (BIO-RAD) containing 30% methanol (Wako)), and filter papers (Extra Thick Blot Paper Criterion™ Size, BIO-RAD) soaked with transfer buffer (Tris/Glycin Buffer (BIO-RAD) containing 30% methanol (Wako)) were laid in order from the minus side, a cover was placed, and electrophoresis was carried out at 80 mA (PowerPac HC™, BIO-RAD) for one and half hours to transfer the separated proteins onto the Immobilon-P Transfer Membrane (MILLIPORE). After transfer, the Immobilon-P Transfer Membrane (MILLIPORE) was soaked in 8 mL of ImmunoBlock (registered trademark, Laboratory Products division of Dainippon Sumitomo Pharma Co., Ltd.) and blocked at 4° C. for 18 hours, and 10 mL of a rabbit polyclonal antibody against human interferon alpha (Cat No. 31130-1, PBL) diluted 2000 times with D-PBS (Wako) containing 0.05% Tween 20 (Polyoxyethylene (20) Sorbitan Monolaurate, Wako) was reacted with the proteins on the membrane for one hour at room temperature while shaking (ROTO-SHAKE GENIE, Scientific Industries). After removing the unbound antibodies, 10 mL of peroxidase conjugated affinity purified anti-rabbit IgG F(c) (Goat) (Rock Land) diluted 5000 times with D-PBS (Wako) containing 0.05% Tween 20 (Polyoxyethylene (20) Sorbitan Monolaurate, Wako) was added and this was reacted for one hour at room temperature while shaking (ROTO-SHAKE GENIE, Scientific Industries). After removing the unbound antibodies, 2 mL of Immobilon™ Western Chemiluminescent HRP Substrate (MILLIPORE) was added for chemiluminescence, and 3-second photographs were taken using Light-Capture ATTO Cooled CCD Camera System (ATTO) at its normal settings. The image obtained by Western blotting is shown in FIG. 25. Bands similar to that of the standard preparation were detected.

Example 29

Construction of pDC6/hOPN

Figure 26:
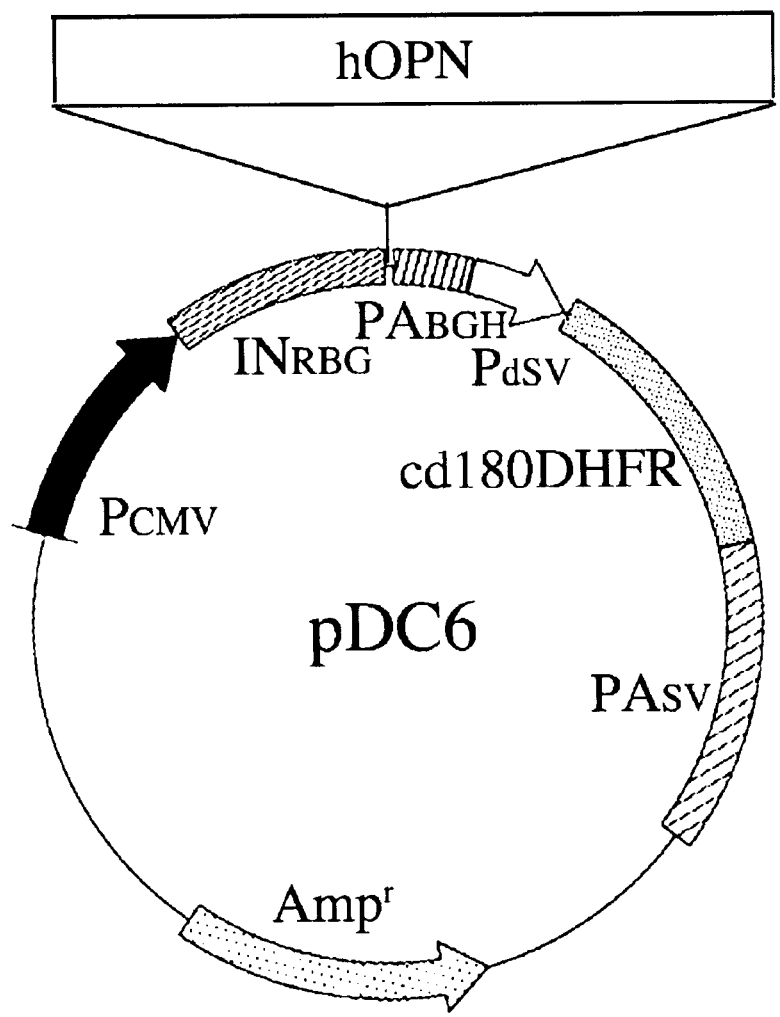
FIG. 26 shows the pDC6/hOPN construct with the respective abbreviations shown below. PCMV: cytomegalovirus promoter; INRBG: rabbit growth hormone intron; hOPN: human osteopontin cDNA; PABGH: bovine growth hormone gene polyA addition signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA addition signal; and Amp$^r$: selection marker (ampicillin resistance) in *E. coli*.

Using methods well known to those skilled in the art, nucleotides No. 1267 to No. 1275 in the vector of the present invention, pDC6, were substituted with a cDNA encoding the human osteopontin (OPN) of SEQ ID NO: 12 (hereinafter referred to as hOPN) to construct pDC6/hOPN (FIG. 26).

Example 30

Transfection of pDC6/hOPN into CHO Cells, and Selection in an HT-Free Medium Using a CD Medium or a CD Medium Supplemented with Non-Animal-Based Additives 2.5 μg of pDC6/hOPN were transfected into 4,000,000 CHO cells (CHO DG44 cells) in 25 cm²-culture flasks using the Lipofectin method (using Lipofectamine™ LTX; Invitrogen). Transfection was performed according to the manufacturer's instructions. 48 hours after gene transfection, the number of cells was counted, and then the cells were diluted in an IS CHO CD w/H (IS Japan) supplemented with 4 mM Gluta MAX™-I (Invitrogen). The cells were plated into five 96-well microtiter plates at a concentration of 4,000 cells/well (480 wells), and after culturing in the presence of 5% carbon dioxide gas at 37° C. for approximately three weeks, viable cells were observed (cell lines growing in HT-free medium).

Expression was verified by Western blotting for all cells for which growth was observed. Lines for which luminescence was observed in Western blots were transferred to 24-well plates together with IS CHO CD w/H (IS Japan) supplemented with 4 mM Gluta MAX™-I (Invitrogen), and cultured until the cells occupied ⅓ or more of each well. Lines for which further growth was observed were transferred to 6-well plates together with IS CHO CD w/H (IS Japan) supplemented with 4 mM Gluta MAX™-I (Invitrogen), and cultured until the cells occupied ⅓ or more of each well. Lines for which further growth was observed were transferred to T75 flasks (BD) together with IS CHO CD w/H (IS Japan) supplemented with 4 mM Gluta MAX™-I (Invitrogen), and cultured until the cells attained $1.0 \times 10^6$ cells/mL or more in each well.

15 mL of each line were placed into a 15 mL tube and centrifuged at 1,100 rpm for seven minutes. The supernatant was discarded, and the cells were suspended in 15 mL of fresh medium (IS CHO CD w/H (IS Japan) supplemented with 4 mM Gluta MAX™-I (Invitrogen)). After counting the number of cells, the cells were diluted with the medium to $5 \times 10^5$ cells/mL, then 7.5 mL of them were transferred to new T75 flasks, and the cells were cultured in the presence of 5% carbon dioxide gas at 37° C. for 14 days. On day 3, day 7, and day 14 of culture, 1 mL of each culture solution was collected, centrifuged at 9,300×g for two minutes, and the supernatant was collected. The production level was determined Example 31

Measurement of the Level of hOPN Produced by the pDC6/hOPN-Transfected Cell Lines Determination of the production level was carried out using an ELISA kit (Human Osteopontin Assay Kit, Code 27158, IBL). To antibody plates (anti-human OPN (0-17) Rabbit IgG A.P. solid phase), 100 µL each of 3-day, 7-day, and 14-day culture supernatants (¹⁄₁₀ to 1/8,000 dilution) and two-fold dilution series (5 to 320 ng/mL) of a standard preparation of recombinant human OPN in a dilution buffer (PBS containing 1% BSA and 0.05% Tween-20) were applied, and incubation was carried out at 37° C. for one hour. This was further incubated with a labeled antibody (HRP-labeled anti-human OPN (10A16) Mouse IgG MoAb Fab A.P.) at 4° C. for one hour. TMB substrate solution was applied at 100 µL/well, and after this was reacted at 25° C. for 30 minutes, a stop solution (1N $H_2SO_4$) was added at 100 µL/well to stop the reaction. Protein concentration was determined using a microplate reader (Model 680, manufactured by BioRad) and on the microplate reader, the absorbance was measured at the wavelength of 450 nm with the wavelength of 655 nm as control. Line 32 yielded 1.12±0.07 µg/mL in 3 days, 7.40±0.24 µg/mL in 7 days, and 13.75±0.03 µg/mL in 14 days. Next, Western blotting was carried out for hOPN in the culture supernatant to confirm protein expression.

Example 32

Figure 27:
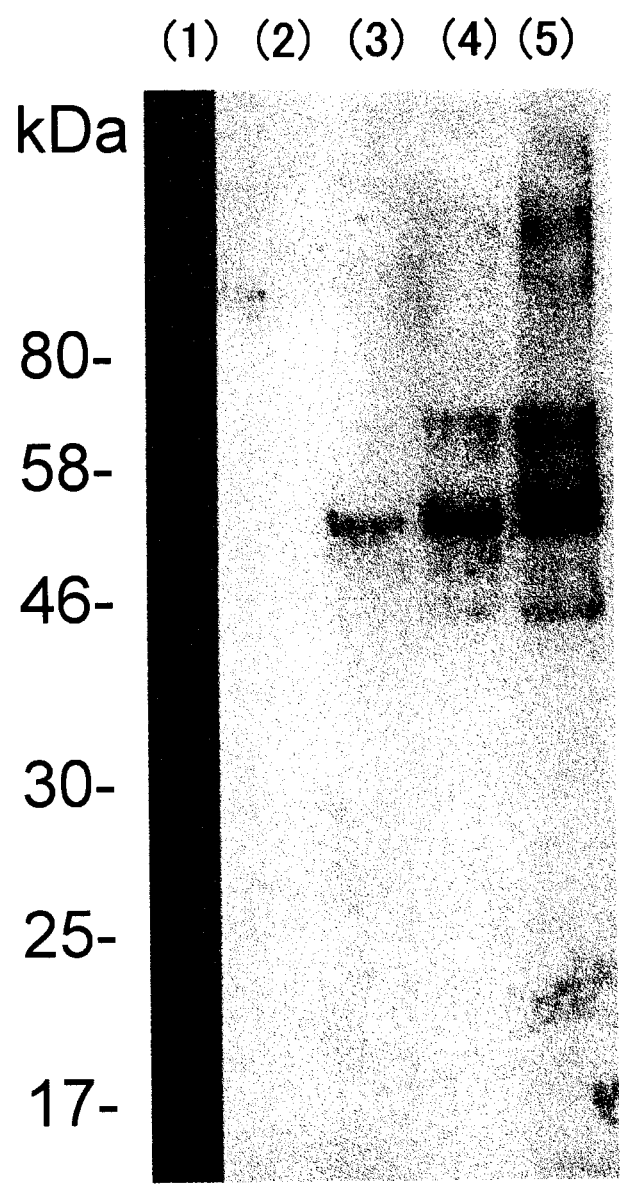
FIG. 27 shows in a photograph examples of detection of hOPN expressed by CHO cells transfected with the pDC6/hOPN expression vector of the present invention by Western blotting. Lane 1: molecular weight marker; lane 2:14-day culture supernatant of CHO DG44 cells; lane 3: 3-day culture supernatant of Cell Line No. 32; lane 4: 7-day culture supernatant of Cell Line No. 32; and lane 5: 14-day culture supernatant of Cell Line No. 32.

Western Blotting of Culture Supernatants of pDC6/hOPN-Transfected Cells 3-day, 7-day, and 14-day culture supernatants of Line 32 obtained in Example 31 described above were analyzed by Western blotting. 10 µL each of the culture supernatants was mixed with 10 µL of Laemmli Sample Buffer (BIO-RAD) containing 5% 2-mercaptoethnanol (Wako) for reduction by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 10% to 20% 17 well (Wako) were placed in an electrophoresis vessel (DPE-1020, DAIICHI PURE CHEMICALS CO., LTD), and 20 µL of the heat-treated sample solutions and standard preparation were applied to the Super™ 10% to 20% 17 well (Wako), and electrophoresis was carried out at 40 mA for 55 minutes (power-supply apparatus: My Run, COSMO BIO CO., LTD was used). Thereafter, the gel was removed from the glass plates, and soaked in a transfer buffer (Tris/Glycin Buffer (BIO-RAD) containing 30% methanol (Wako)) while shaking (ROTO-SHAKE GENIE, Scientific Industries) for five minutes. Immobilon-P Transfer Membrane (MILLIPORE) was activated by sequential soaking in 8 mL of methanol (Wako) for 15 seconds, 8 mL of MilliQ water (MILLIPORE) for two minutes, and 8 mL of transfer buffer (Tris/Glycin Buffer (BIO-RAD) containing 30% methanol (Wako)) for five minutes while shaking (ROTO-SHAKE GENIE, Scientific Industries). In a transfer apparatus (TRANS-BLO, SD SEMI-DRY TRANSFER CELL, BIO-RAD), filter papers (Extra Thick Blot Paper Criterion™ Size, BIO-RAD) soaked with transfer buffer (Tris/Glycin Buffer (BIO-RAD) containing 30% methanol (Wako)), the activated Immobilon-P Transfer Membrane (MILLIPORE), the gel after electrophoresis soaked in transfer buffer (Tris/Glycin Buffer (BIO-RAD) containing 30% methanol (Wako)), and filter papers (Extra Thick Blot Paper Criterion™ Size, BIO-RAD) soaked with transfer buffer (Tris/Glycin Buffer (BIO-RAD) containing 30% methanol (Wako)) were laid in order from the minus side, a cover was placed, and electrophoresis was carried out at 80 mA (PowerPac HC™, BIO-RAD) for an hour and a half to transfer the separated proteins onto the Immobilon-P Transfer Membrane (MILLIPORE). After transfer, the Immobilon-P Transfer Membrane (MILLIPORE) was soaked in 8 mL of Immuno-Block (registered trademark, Laboratory Products division of Dainippon Sumitomo Pharma Co., Ltd.) and blocked at 4° C. for 18 hours, and 10 mL of an anti-human OPN mouse monoclonal antibody (anti-human osteopontin (10A16) mouse IgG MoAb, Cat 10011, IBL) diluted 2000 times with D-PBS (Wako) containing 0.05% Tween 20 (Polyoxyethylene (20) Sorbitan Monolaurate, Wako) was reacted with the proteins on the membrane for one hour at room temperature while shaking (ROTO-SHAKE GENIE, Scientific Industries). After removing the unbound antibodies, 10 mL of a peroxidase-labeled anti-mouse IgG antibody (goat anti-mouse IgG (H+L), Cat 115-036-062, Jackson) diluted 5000 times with D-PBS (Wako) containing 0.05% Tween 20 (Polyoxyethylene (20) Sorbitan Monolaurate, Wako) was added and this was reacted for one hour at room temperature while shaking (ROTO-SHAKE GENIE, Scientific Industries). After removing the unbound antibodies, 2 mL of Immobilon™ Western Chemiluminescent HRP Substrate (MILLIPORE) was added for chemiluminescence, and 30-second photographs were taken using Light-Capture ATTO Cooled CCD Camera System (ATTO) at its normal settings. The image obtained by Western blotting is shown in FIG. 27.

INDUSTRIAL APPLICABILITY

The present invention can provide expression vectors that enable high-level production of foreign gene-derived proteins using dihydrofolate reductase gene-deficient mammalian cells as host. Furthermore, they can produce proteins that have post-translational modifications inherent to mammals and high biological activity. Therefore, the production cost of useful protein substances such as biopharmaceuticals can be significantly reduced.

Furthermore, since the methods for protein production according to the present invention do not use viruses or microorganisms, highly safe protein production is possible.

The invention claimed is:

1. An expression vector for producing a foreign gene-derived protein in a mammalian host cell, which comprises:
   (a) a translation-impaired dihydrofolate reductase gene cassette (translation-impaired DHFR gene cassette) comprising a region with rare codons wherein the rare codons comprise GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and/or GUA for valine, wherein from the 5' end of the DHFR gene, each of at least the first 30% of the DHFR gene codons is replaced by the rare codon encoding the same amino acid as the DHFR gene codon, wherein the translation-impaired DHFR gene cassette uses a promoter whose enhancer portion has been removed; and
   (b) a gene cassette comprising a cloning site for integration of a foreign gene between a transcriptionally active promoter and a stable polyadenylation signal.

2. A method for producing a transformant that has ability to produce a high level of a foreign gene-derived protein, which comprises the steps of inserting a foreign gene into the expression vector of claim 1, and transforming a dihydrofolate reductase gene-deficient host cell with the expression vector.

3. A method for producing a foreign gene-derived protein, which comprises the steps of:
   (a) inserting a foreign gene into the expression vector of claim 1;
   (b) transforming a dihydrofolate reductase gene-deficient host cell with the expression vector;
   (c) culturing the transformant in a hypoxanthine-thymidine-free medium; and
   (d) collecting the foreign gene-derived protein from the cultured transformant.

4. The method of claim 3, wherein a chemically defined medium (CD medium) or a CD medium supplemented with a non-animal-based additive is used for culturing in step (c) of claim 3.

5. A method of screening for a transformant that has ability to produce a high level of a foreign gene-derived protein, which comprises the steps of:
   (a) inserting a foreign gene into the expression vector of claim 1;
   (b) transforming a dihydrofolate reductase gene-deficient host cell with the expression vector; and
   (c) culturing the transformant in a hypoxanthine-thymidine-free medium; and
   (d) determining an expression level of the foreign gene-derived protein and thereby determining the transformant.

* * * * *

SEQUENCE LISTING

<160> NUMBER OF SEQ ID NOS: 12

<210> SEQ ID NO 1
<211> LENGTH: 5848
<212> TYPE: DNA
<213> ORGANISM: Artificial
<220> FEATURE:
<223> OTHER INFORMATION: An artificially synthesized vector sequence

<400> SEQUENCE: 1

| | | | | | |
|---|---|---|---|---|---|
| cgatgtacgg | gccagatata | cgcgttgaca | ttgattattg | actagttatt | aatagtaatc | 60 |
| aattacgggg | tcattagttc | atagcccata | tatggagttc | cgcgttacat | aacttacggt | 120 |
| aaatggcccg | cctggctgac | cgcccaacga | cccccgccca | ttgacgtcaa | taatgacgta | 180 |
| tgttcccata | gtaacgccaa | tagggacttt | ccattgacgt | caatgggtgg | agtatttacg | 240 |
| gtaaactgcc | cacttggcag | tacatcaagt | gtatcatatg | ccaagtacgc | cccctattga | 300 |
| cgtcaatgac | ggtaaatggc | ccgcctggca | ttatgcccag | tacatgacct | tatgggactt | 360 |
| tcctacttgg | cagtacatct | acgtattagt | catcgctatt | accatggtga | tgcggttttg | 420 |
| gcagtacatc | aatgggcgtg | gatagcggtt | tgactcacgg | ggatttccaa | gtctccaccc | 480 |
| cattgacgtc | aatgggagtt | tgttttggca | ccaaaatcaa | cgggactttc | caaaatgtcg | 540 |
| taacaactcc | gccccattga | cgcaaatggg | cggtaggcgt | gtacggtggg | aggtctatat | 600 |
| aagcagagct | ctctggctaa | ctagagaacc | cactgttaac | tggcttatcg | aaattgtcga | 660 |
| ggagaacttc | agggtgagtt | tggggacccct | tgattgttct | ttcttttcg | ctattgtaaa | 720 |
| attcatgtta | tatggagggg | gcaaagtttt | cagggtgttg | tttagaatgg | gaagatgtcc | 780 |
| cttgtatcac | catggaccct | catgataatt | tgtttctttt | cactttctac | tctgttgaca | 840 |
| accattgtct | cctcttattt | tcttttcatt | ttctgtaact | ttttcgttaa | actttagctt | 900 |
| gcatttgtaa | cgaattttta | aattcacttt | tgtttatttg | tcagattgta | agtactttct | 960 |
| ctaatcactt | ttttttcaag | gcaatcaggg | tatattatat | tgtacttcag | cacagtttta | 1020 |
| gagaacaatt | gttataatta | aatgataagg | tagaatattt | ctgcatataa | attctggctg | 1080 |
| gcgtggaaat | attcttattg | gtagaaacaa | ctacatcctg | gtcatcatcc | tgcctttctc | 1140 |
| tttatggtta | caatgatata | cactgtttga | gatgaggata | aaatactctg | agtccaaacc | 1200 |
| gggcccctct | gctaaccatg | ttcatgcctt | cttcttttc | ctacagctcc | tgggcaacgt | 1260 |
| gctggcggcc | gccttctaga | gcctcgactg | tgccttctag | ttgccagcca | tctgttgttt | 1320 |
| gcccctcccc | cgtgccttcc | ttgaccctgg | aaggtgccac | tcccactgtc | ctttcctaat | 1380 |
| aaaatgagga | aattgcatcg | cattgtctga | gtaggtgtca | ttctattctg | ggggtgggg | 1440 |
| tggggcagga | cagcaagggg | gaggattggg | aagacaatag | caggcatgct | ggggaggatc | 1500 |
| tccgcggtgt | ggaatgtgtg | tcagttaggg | tgtggaaagt | ccccaggctc | cccagcaggc | 1560 |
| agaagtatgc | aaagcatgca | tctcaattag | tcagcaacca | tagtcccgcc | cctaactccg | 1620 |
| cccatcccgc | ccctaactcc | gcccagttcc | gcccattctc | cgccccatgg | ctgactaatt | 1680 |
| tttttattt | atgcagaggc | cgaggccgcc | tcggcctctg | agctattcca | gaagtagtga | 1740 |
| ggaggctttt | ttggaggcct | aggcttttgc | aaaaagctg | cagatggttc | gaccattgaa | 1800 |
| ctgcatcgtc | gccgtgtccc | aaaatatggg | gattggcaag | aacggagacc | taccctggcc | 1860 |
| tccgctcagg | aacgagttca | agtacttcca | agaatgacc | acaacctctt | cagtggaagg | 1920 |
| taaacagaat | ctggtgatta | tgggtaggaa | aacctggttc | tccattcctg | agaagaatcg | 1980 |
| acctttaaag | gacagaatta | atatagttct | cagtagagaa | ctcaaagaac | caccacgagg | 2040 |

```
agctcatttt cttgccaaaa gtttggatga tgccttaaga cttattgaac aaccggaatt    2100
ggcaagtaaa gtagacatgg tttggatagt cggaggcagt tctgtttacc aggaagccat    2160
gaatcaacca ggccacctca gactctttgt gacaaggatc atgcaggaat ttgaaagtga    2220 cacgttttc ccagaaattg atttggggaa atataaactt ctcccagaat acccaggcgt     2280
cctctctgag gtccaggagg aaaaaggcat caagtataag tttgaagtct acgagaagaa    2340
agactaaaga tccgtgacat aattggacaa actacctaca gagatttaaa gctctaaggt    2400
aaatataaaa ttttaagtg tataatgtgt taaactactg attctaattg tttgtgtatt     2460
ttagattcca acctatggaa ctgatgaatg ggagcagtgg tggaatgcct taatgagga     2520 aaacctgttt tgctcagaag aaatgccatc tagtgatgat gaggctactg ctgactctca    2580
acattctact cctccaaaaa agaagagaaa ggtagaagac cccaaggact ttccttcaga    2640
attgctaagt tttttgagtc atgctgtgtt tagtaataga actcttgctt gctttgctat    2700
ttacaccaca aaggaaaaag ctgcactgct atacaagaaa attatggaaa aatattctgt    2760
aacctttata agtaggcata acagttataa tcataacata ctgttttttc ttactccaca    2820
caggcataga gtgtctgcta ttaataacta tgctcaaaaa ttgtgtacct ttagcttttt    2880
aatttgtaaa ggggttaata aggaatattt gatgtatagt gccttgacta gagatcataa    2940
tcagccatac cacatttgta gaggttttac ttgctttaaa aaacctccca cacctccccc    3000
tgaacctgaa acataaaatg aatgcaattg ttgttgttaa cttgtttatt gcagcttata    3060
atggttacaa ataaagcaat agcatcacaa atttcacaaa taaagcattt ttttcactgc    3120
attctagttg tggtttgtcc aaactcatca atgtatctta tcatgtctgg gcccatcgat    3180
gaattcaacg tacgtagctt ggcactggcc gtcgttttac aacgtcgtga ctgggaaaac    3240
cctggcgtta cccaacttaa tcgccttgca gcacatcccc ctttcgccag ctggcgtaat    3300
agcgaagagg cccgcaccga tcgcccttcc caacagttgc gcagcctgaa tggcgaatgg    3360
cgcctgatgc ggtattttct ccttacgcat ctgtgcggta tttcacaccg catatggtgc    3420
actctcagta caatctgctc tgatgccgca tagttaagcc agccccgaca cccgccaaca    3480
cccgctgacg cgccctgacg ggcttgtctg ctcccggcat ccgcttacag acaagctgtg    3540
accgtctccg ggagctgcat gtgtcagagg ttttcaccgt catcaccgaa acgcgcgagg    3600 acgaagggc ctcgtgatac gcctattttt ataggttaat gtcatgataa taatggtttc     3660
ttagacgtca ggtggcactt ttcggggaaa tgtgcgcgga acccctattt gtttattttt    3720
ctaaatacat tcaaatatgt atccgctcat gagacaataa ccctgataaa tgcttcaata    3780
atattgaaaa aggaagagta tgagtattca acatttccgt gtcgccctta ttcccttttt    3840
tgcggcattt tgccttcctg tttttgctca cccagaaacg ctggtgaaag taaaagatgc    3900
tgaagatcag ttgggtgcac gagtgggtta catcgaactg gatctcaaca gcggtaagat    3960
ccttgagagt tttcgccccg aagaacgttt tccaatgatg agcacttta aagttctgct     4020 atgtggcgcg gtattatccc gtattgacgc cgggcaagag caactcggtc gccgcataca    4080
ctattctcag aatgacttgg ttgagtactc accagtcaca gaaaagcatc ttacggatgg    4140
catgacagta agagaattat gcagtgctgc cataaccatg agtgataaca ctgcggccaa    4200
cttacttctg acaacgatcg gaggaccgaa ggagctaacc gcttttttgc acaacatggg    4260
ggatcatgta actcgccttg atcgttggga accggagctg aatgaagcca taccaaacga    4320
cgagcgtgac accacgatgc ctgtagcaat ggcaacaacg ttgcgcaaac tattaactgg    4380
```

```
cgaactactt actctagctt cccggcaaca attaatagac tggatggagg cggataaagt    4440
tgcaggacca cttctgcgct cggcccttcc ggctggctgg tttattgctg ataaatctgg    4500
agccggtgag cgtgggtctc gcggtatcat tgcagcactg gggccagatg gtaagccctc    4560
ccgtatcgta gttatctaca cgacggggag tcaggcaact atggatgaac gaaatagaca    4620
gatcgctgag ataggtgcct cactgattaa gcattggtaa ctgtcagacc aagtttactc    4680
atatatactt tagattgatt taaaacttca ttttaattt aaaaggatct aggtgaagat     4740 ccttttttgat aatctcatga ccaaaatccc ttaacgtgag ttttcgttcc actgagcgtc    4800 agacccccgta gaaaagatca aaggatcttc ttgagatcct ttttttctgc gcgtaatctg   4860
ctgcttgcaa acaaaaaaac caccgctacc agcggtggtt tgtttgccgg atcaagagct    4920
accaactctt tttccgaagg taactggctt cagcagagcg cagataccaa atactgtcct    4980
tctagtgtag ccgtagttag gccaccactt caagaactct gtagcaccgc ctacatacct    5040
cgctctgcta atcctgttac cagtggctgc tgccagtggc gataagtcgt gtcttaccgg    5100
gttggactca agacgatagt taccggataa ggcgcagcgg tcgggctgaa cggggggttc    5160
gtgcacacag cccagcttgg agcgaacgac ctacaccgaa ctgagatacc tacagcgtga    5220
gcattgagaa agcgccacgc ttcccgaagg gagaaaggcg gacaggtatc cggtaagcgg    5280
cagggtcgga acaggagagc gcacgaggga gcttccaggg ggaaacgcct ggtatcttta    5340
tagtcctgtc gggtttcgcc acctctgact tgagcgtcga ttttgtgat gctcgtcagg     5400 ggggcggagc ctatggaaaa acgccagcaa cgcggccttt ttacggttcc tggccttttg    5460
ctggcctttt gctcacatgt tctttcctgc gttatcccct gattctgtgg ataaccgtat    5520
taccgccttt gagtgagctg ataccgctcg ccgcagccga acgaccgagc gcagcgagtc    5580
agtgagcgag gaagcggaag agcgcccaat acgcaaaccg cctctccccg cgcgttggcc    5640
gattcattaa tgcagctggc acgacaggtt tcccgactgg aaagcgggca gtgagcgcaa    5700
cgcaattaat gtgagttagc tcactcatta ggcaccccag gctttacact ttatgcttcc    5760
ggctcgtatg ttgtgtggaa ttgtgagcgg ataacaattt cacacaggaa acagctatga    5820
ccatgattac gaatttcgta cgaagctt                                       5848
```

<210> SEQ ID NO 2
<211> LENGTH: 564
<212> TYPE: DNA
<213> ORGANISM: Artificial
<220> FEATURE:
<223> OTHER INFORMATION: An artificially synthesized nucleotide sequence

<400> SEQUENCE: 2

```
atggtacgac cattaaattg tattgtagca gtatcacaaa atatgggtat tggtaaaaat      60
ggtgatttac catggccacc attacgaaat gaatttaaat attttcaacg aatgactact     120
acttcatcag tagaaggtaa acaaaattta gtaattatgg gtcgaaaaac ttggttttca     180
attccagaaa aaaatcgacc attaaaagat cgaattaata ttgtattatc acgagaatta     240
aaagaaccac cacgaggtgc acatttttta gcaaaatcat tagatgatgc attacgatta     300
attgaacaac cagaattatc atcaaaagta gatatggtat ggattgtagg tggttcatca     360
gtatatcaag aagcaatgaa tcaaccaggt catttacgat tatttgtaac tcgaattatg     420
caagaatttg aatcagatac tttttttcca gaaattgatt taggtaaata taaattatta     480
ccagaatatc caggtgtatt atcagaagta caagaagaaa aaggtattaa atataaattt     540
gaagtatatg aaaaaaaaga ttaa                                            564
```

<210> SEQ ID NO 3
<211> LENGTH: 564
<212> TYPE: DNA
<213> ORGANISM: Artificial
<220> FEATURE:
<223> OTHER INFORMATION: An artificially synthesized nucleotide sequence

<400> SEQUENCE: 3

| | | | | | |
|---|---|---|---|---|---|
| atggtacgac | cattaaattg | tattgtagca | gtatcacaaa | atatgggtat | tggtaaaaat | 60 |
| ggtgatttac | catggccacc | attacgaaat | gagttcaagt | acttccaaag | aatgaccaca | 120 |
| acctcttcag | tggaaggtaa | acagaatctg | gtgattatgg | gtaggaaaac | ctggttctcc | 180 |
| attcctgaga | agaatcgacc | tttaaaggac | agaattaata | tagttctcag | tagagaactc | 240 |
| aaagaaccac | cacgaggagc | tcattttctt | gccaaaagtt | tggatgatgc | cttaagactt | 300 |
| attgaacaac | cggaattggc | aagtaaagta | gacatggttt | ggatagtcgg | aggcagttct | 360 |
| gtttaccagg | aagccatgaa | tcaaccaggc | cacctcagac | tctttgtgac | aaggatcatg | 420 |
| caggaatttg | aaagtgacac | gttttcccca | gaaattgatt | tggggaaata | taaacttctc | 480 |
| ccagaatacc | caggcgtcct | ctctgaggtc | caggaggaaa | aaggcatcaa | gtataagttt | 540 |
| gaagtctacg | agaagaaaga | ctaa | | | 564 |

<210> SEQ ID NO 4
<211> LENGTH: 564
<212> TYPE: DNA
<213> ORGANISM: Artificial
<220> FEATURE:
<223> OTHER INFORMATION: An artificially synthesized nucleotide sequence

<400> SEQUENCE: 4

| | | | | | |
|---|---|---|---|---|---|
| atggtacgac | cattaaattg | tattgtagca | gtatcacaaa | atatgggtat | tggtaaaaat | 60 |
| ggtgatttac | catggccacc | attacgaaat | gaatttaaat | attttcaacg | aatgactact | 120 |
| acttcatcag | tagaaggtaa | acaaaattta | gtaattatgg | gtcgaaaaac | ttggttttca | 180 |
| attcctgaga | agaatcgacc | tttaaaggac | agaattaata | tagttctcag | tagagaactc | 240 |
| aaagaaccac | cacgaggagc | tcattttctt | gccaaaagtt | tggatgatgc | cttaagactt | 300 |
| attgaacaac | cggaattggc | aagtaaagta | gacatggttt | ggatagtcgg | aggcagttct | 360 |
| gtttaccagg | aagccatgaa | tcaaccaggc | cacctcagac | tctttgtgac | aaggatcatg | 420 |
| caggaatttg | aaagtgacac | gttttcccca | gaaattgatt | tggggaaata | taaacttctc | 480 |
| ccagaatacc | caggcgtcct | ctctgaggtc | caggaggaaa | aaggcatcaa | gtataagttt | 540 |
| gaagtctacg | agaagaaaga | ctaa | | | 564 |

<210> SEQ ID NO 5
<211> LENGTH: 564
<212> TYPE: DNA
<213> ORGANISM: Artificial
<220> FEATURE:
<223> OTHER INFORMATION: An artificially synthesized nucleotide sequence

<400> SEQUENCE: 5

| | | | | | |
|---|---|---|---|---|---|
| atggtacgac | cattaaattg | tattgtagca | gtatcacaaa | atatgggtat | tggtaaaaat | 60 |
| ggtgatttac | catggccacc | attacgaaat | gaatttaaat | attttcaacg | aatgactact | 120 |
| acttcatcag | tagaaggtaa | acaaaattta | gtaattatgg | gtcgaaaaac | ttggttttca | 180 |
| attccagaaa | aaaatcgacc | attaaaagat | cgaattaata | ttgtattatc | acgagaatta | 240 |

```
aaagaaccac cacgaggtgc acatttttta gccaaaagtt tggatgatgc cttaagactt    300
attgaacaac cggaattggc aagtaaagta gacatggttt ggatagtcgg aggcagttct    360
gtttaccagg aagccatgaa tcaaccaggc cacctcagac tctttgtgac aaggatcatg    420
caggaatttg aaagtgacac gttttttccca gaaattgatt tggggaaata taaacttctc    480
ccagaatacc caggcgtcct ctctgaggtc caggaggaaa aaggcatcaa gtataagttt    540
gaagtctacg agaagaaaga ctaa                                           564

<210> SEQ ID NO 6
<211> LENGTH: 759
<212> TYPE: DNA
<213> ORGANISM: Homo sapiens

<400> SEQUENCE: 6
ggccgccacc atgagcctgt tccccagcct gccctgctg ctgctgagca tggtggccgc     60
cagctacagc gagaccgtga cctgcgagga cgcccagaag acctgccccg ccgtgattgc    120
ctgcagcagc cccggcatca acggcttccc cggcaaggac ggccgcgacg caccaaggg    180 cgagaagggc gagcccggcc agggcctgcg cggcctgcag ggccccccg gcaagctggg    240 ccccccggc aaccccggcc ccagcggcag ccccggcccc aagggccaga agggcgaccc    300
cggcaagagc cccgacggcg acagcagcct ggccgccagc gagcgcaagg ccctgcagac    360
cgagatggcc cgcatcaaga gtggctgac cttcagcctg gcaagcagg tgggcaacaa    420 gttcttcctg accaacggcg agataatgac cttcgagaag gtgaaggccc tgtgcgtgaa    480
gttccaggcc agcgtggcca ccccccgcaa cgccgccgag aacggcgcca ttcagaacct    540
gatcaaggag gaggccttcc tgggcatcac cgacgagaag accgagggcc agttcgtgga    600
cctgaccgga aaccgcctga cctacaccaa ctggaacgag ggcgagccca caacgccgg    660 cagcgacgag gactgcgtgc tgctgctgaa gaacggccag tggaacgacg tgcctgcag    720 caccagccac ctggccgtgt gcgagttccc catctgaat                           759

<210> SEQ ID NO 7
<211> LENGTH: 594
<212> TYPE: DNA
<213> ORGANISM: Homo sapiens

<400> SEQUENCE: 7
ggccgccacc atgggtgttc atgaatgtcc agcttggtta tggttattat tatctttatt     60
atctttacca ttaggtttac cagttttagg tgccccccc cgcctgatct gcgacagccg    120
cgtgctggag cgctacctgc tggaggccaa ggaggccgag aacatcacca ccggctgcgc    180
cgagcactgc agcctgaacg agaacatcac cgtgcccgac accaaggtga acttctacgc    240
ctggaagcgc atggaggtgg ccagcaggc cgtggaggtg tggcagggcc tggccctgct    300
gagcgaggcc gtgctgcgcg ccaggccct gctggtgaac agcagccagc ctgggagcc    360 cctgcagctg cacgtggaca aggccgtgag cggcctgcgc agcctgacca ccctgctgcg    420
cgccctgggc gcccagaagg aggccatcag ccccccgac gccgccagcg ccgcccccct    480
gcgcaccatc accgccgaca ccttccgcaa gctgttccgc gtgtacagca acttcctgcg    540
cggcaagctg aagctgtaca ccggcgaggc ctgccgcacc ggcgaccgct gaat          594

<210> SEQ ID NO 8
<211> LENGTH: 594
<212> TYPE: DNA
<213> ORGANISM: Homo sapiens
```

<400> SEQUENCE: 8

```
ggccgccacc atgggtgttc atgaatgtcc agcttggtta tggttattat tatctttatt      60
atctttacca ttaggtttac cagttttagg tgccccccc cgcctgatct gcgacagccg     120
cgtgctggag cgctacctgc tggaggccaa ggaggccgag aacatcacca ccggctgcaa     180
cgagacctgc agcctgaacg agaacatcac cgtgcccgac accaaggtga acttctacgc     240
ctggaagcgc atggaggtgg ccagcaggc cgtggaggtg tggcagggcc tggccctgct     300
gagcgaggcc gtgctgcgcg ccaggccct gctggtgaac agcagccagg tgaacgagac     360
cctgcagctg cacgtggaca aggccgtgag cggcctgcgc agcctgacca ccctgctgcg     420
cgccctgggc gcccagaagg aggccatcag cccccccgac gccgccagcg ccgccccct     480
gcgcaccatc accgccgaca ccttccgcaa gctgttccgc gtgtacagca acttcctgcg     540
cggcaagctg aagctgtaca ccggcgaggc ctgccgcacc ggcgaccgct gaat           594
```

<210> SEQ ID NO 9
<211> LENGTH: 626
<212> TYPE: DNA
<213> ORGANISM: Homo sapiens

<400> SEQUENCE: 9

```
ggccgccacc atggctggtc cagctactca atctccaatg aaattaatgg ctttacaatt      60
attattatgg cattctgctt tatggactgt tcaagaagct actccctgg gccccgccag     120
cagcctgccc cagagcttcc tgctgaagtg cctggagcag gtgcgcaaga tccagggcga     180
cggcgccgcc ctgcaggaga agctgtgcgc cacctacaag ctgtgccacc ggaggagct     240
ggtgctgctg ggccacagcc tgggcatccc ctgggccccc tgagcagct gccccagcca     300
ggccctgcag ctggccggct gcctgagcca gctgcacagc ggcctgttcc tgtaccaggg     360
cctgctgcag gccctcgagg gcatcagccc cgagctgggc cccacctgg acccctgca     420
gctggacgtg gccgacttcg ccaccaccat ctggcagcag atggaggagc tgggcatggc     480
ccccgccctg cagcccaccc agggcgccat gcccgccttc gccagcgcct tccagcgccg     540
cgccggcggc gtgctggtgg ccagccacct gcagagcttc ctggaggtga gctaccgcgt     600
gctgcgccac ctggcccagc cctagt                                          626
```

<210> SEQ ID NO 10
<211> LENGTH: 446
<212> TYPE: DNA
<213> ORGANISM: Homo sapiens

<400> SEQUENCE: 10

```
ggccgccacc atgtggttac aatctttatt attattaggt actgttgctt gttctatctc      60
tgccccgcc cgcagcccca gcccagcac ccagccctgg gagcacgtga acgccatcca     120
ggaggccgc gcctgctga acctgagccg cgacaccgcc gccgagatga cgagaccgt     180
ggaggtgatc agcgagatgt tcgacctgca ggagcccacc tgcctgcaga cccgcctgga     240
gctgtacaag cagggcctgc gcggcagcct gaccaagctg aagggccccc tgaccatgat     300
ggccagccac tacaagcagc actgcccccc caccccgag accagctgcg ccacccagac     360
catcaccttc gagagcttca aggagaacct gaaggacttc ctgctggtga tccccttcga     420
ctgctgggag cccgtgcagg agtagt                                          446
```

<210> SEQ ID NO 11

```
<211> LENGTH: 578
<212> TYPE: DNA
<213> ORGANISM: Homo sapiens

<400> SEQUENCE: 11
ggccgccacc atggctttaa cttttgcttt attagttgct ttattagttt tatcttgtaa      60
atcttcttgt tctgttggtt gcgacctgcc ccagacccac agcctgggca gccgccgcac     120
cctgatgctg ctggcccaga tgcgccgcat cagcctgttc agctgcctga aggaccgcca     180
cgacttcggc ttcccccagg aggagttcgg caaccagttc cagaaggccg agaccatccc     240
cgtgctgcac gagatgatcc agcagatctt caacctgttc agcaccaagg acagcagcgc     300
cgcctgggac gagaccctgc tggacaagtt ctacaccgag ctgtaccagc agctgaacga     360
cctggaggcc tgcgtgatcc agggcgtggg cgtgaccgag acccccctga tgaaggagga     420
cagcatcctg gccgtgcgca agtacttcca gcgcatcacc ctgtacctga aggagaagaa     480
gtacagcccc tgcgcctggg aggtggtgcg cgccgagatc atgcgcagct tcagcctgag     540
caccaacctg caggagagcc tgcgcagcaa ggagtagt                             578

<210> SEQ ID NO 12
<211> LENGTH: 952
<212> TYPE: DNA
<213> ORGANISM: Homo sapiens

<400> SEQUENCE: 12
ggccgccacc atgagaatcg ctgttatctg tttttgttta ttaggtatca cttgtgctat      60
ccccgtgaag caggccgaca gcggcagcag cgaggagaag cagctgtaca acaagtaccc     120
cgacgccgtg gccacctggc tgaaccccga ccccagccag aagcagaacc tgctggcccc     180
ccagaacgcc gtgagcagcg aggagaccaa cgacttcaag caggagaccc tgcccagcaa     240
gagcaacgag agccacgacc acatggacga catggacgac gaggacgacg acgaccacgt     300
ggacagccag gacagcatcg acagcaacga cagcgacgac gtggacgaca ccgacgacag     360
ccaccagagc gacgagagcc accacagcga cgagagcgac gagctggtga ccgacttccc     420
caccgacctg cccgccaccg aggtgttcac ccccgtggtg cccaccgtgg acacctacga     480
cggccgcggc gacagcgtgg tgtacggcct gcgcagcaag agcaagaagt tccgccgccc     540
cgacatccag tacccccgacg ccaccgacga ggacatcacc agccacatgg agagcgagga     600
gctgaacggc gcctacaagg ccatccccgt ggcccaggac ctgaacgccc cagcgactg     660 ggacagccgc ggcaaggaca gctacgagac cagccagctg gacgaccaga gcgccgagac     720
ccacagccac aagcagagcc gcctgtacaa gcgcaaggcc aacgacgaga gcaacgagca     780
cagcgacgtg atcgacagcc aggagctgag caaggtgagc cgcgagttcc acagccacga     840
gttccacagc cacgaggaca tgctggtggt ggaccccaag agcaaggagg aggacaagca     900
cctgaagttc cgcatcagcc acgagctgga cagcgccagc agcgaggtga ac             952
```